United States Patent
Kong

(10) Patent No.: US 11,519,007 B2
(45) Date of Patent: Dec. 6, 2022

(54) TUMOR-NAVIGATING, SELF-ERADICATING, TRAIL-ARMED SALMONELLA FOR PRECISION CANCER THERAPY

(71) Applicant: ARIZONA BOARD OF REGENTS ON BEHALF OF ARIZONA STATE UNIVERSITY, Scottsdale, AZ (US)

(72) Inventor: Wei Kong, Phoenix, AZ (US)

(73) Assignee: ARIZONA BOARD OF REGENTS ON BEHALF OF ARIZONA STATE UNIVERSITY, Scottsdale, AZ (US)

(*) Notice: Subject to any disclaimer, the term of this patent is extended or adjusted under 35 U.S.C. 154(b) by 0 days.

(21) Appl. No.: 17/433,222

(22) PCT Filed: Feb. 20, 2020

(86) PCT No.: PCT/US2020/019111
§ 371 (c)(1),
(2) Date: Aug. 23, 2021

(87) PCT Pub. No.: WO2020/172462
PCT Pub. Date: Aug. 27, 2020

(65) Prior Publication Data
US 2022/0042046 A1 Feb. 10, 2022

Related U.S. Application Data

(60) Provisional application No. 62/809,222, filed on Feb. 22, 2019.

(51) Int. Cl.
*C12N 15/87* (2006.01)
*A61P 35/00* (2006.01)
*A61K 35/74* (2015.01)
*C12R 1/42* (2006.01)

(52) U.S. Cl.
CPC .............. *C12N 15/87* (2013.01); *A61K 35/74* (2013.01); *A61P 35/00* (2018.01); *C12R 2001/42* (2021.05)

(58) Field of Classification Search
None
See application file for complete search history.

(56) References Cited

U.S. PATENT DOCUMENTS

| | | |
|---|---|---|
| 5,763,223 A | 6/1998 | Wiley et al. |
| 2005/0244374 A1 | 11/2005 | Goebel et al. |
| 2009/0169517 A1 | 7/2009 | Bermudes et al. |
| 2011/0287052 A1* | 11/2011 | Curtiss, III ............. A61P 31/04 424/200.1 |
| 2013/0209405 A1* | 8/2013 | Curtiss, III ............. C12N 1/36 424/93.2 |
| 2017/0306338 A1 | 10/2017 | Curtiss, III et al. |
| 2017/0333493 A1 | 11/2017 | Ahmer et al. |

FOREIGN PATENT DOCUMENTS

WO 2017/123675 A8 8/2017

* cited by examiner

*Primary Examiner* — Christopher M Babic
*Assistant Examiner* — Kimberly A Aron
(74) *Attorney, Agent, or Firm* — Quarles & Brady, LLP

(57) ABSTRACT

The present disclosure relates to genetically modified strains of *Salmonella*, engineered to be tumor navigating, self-eradicating, and armed with TRAIL to trigger tumor cell apoptosis. Also provided herein are methods of producing and methods of using such genetically modified *Salmonella* strains to treat cancer.

20 Claims, 37 Drawing Sheets
(12 of 37 Drawing Sheet(s) Filed in Color)
Specification includes a Sequence Listing.

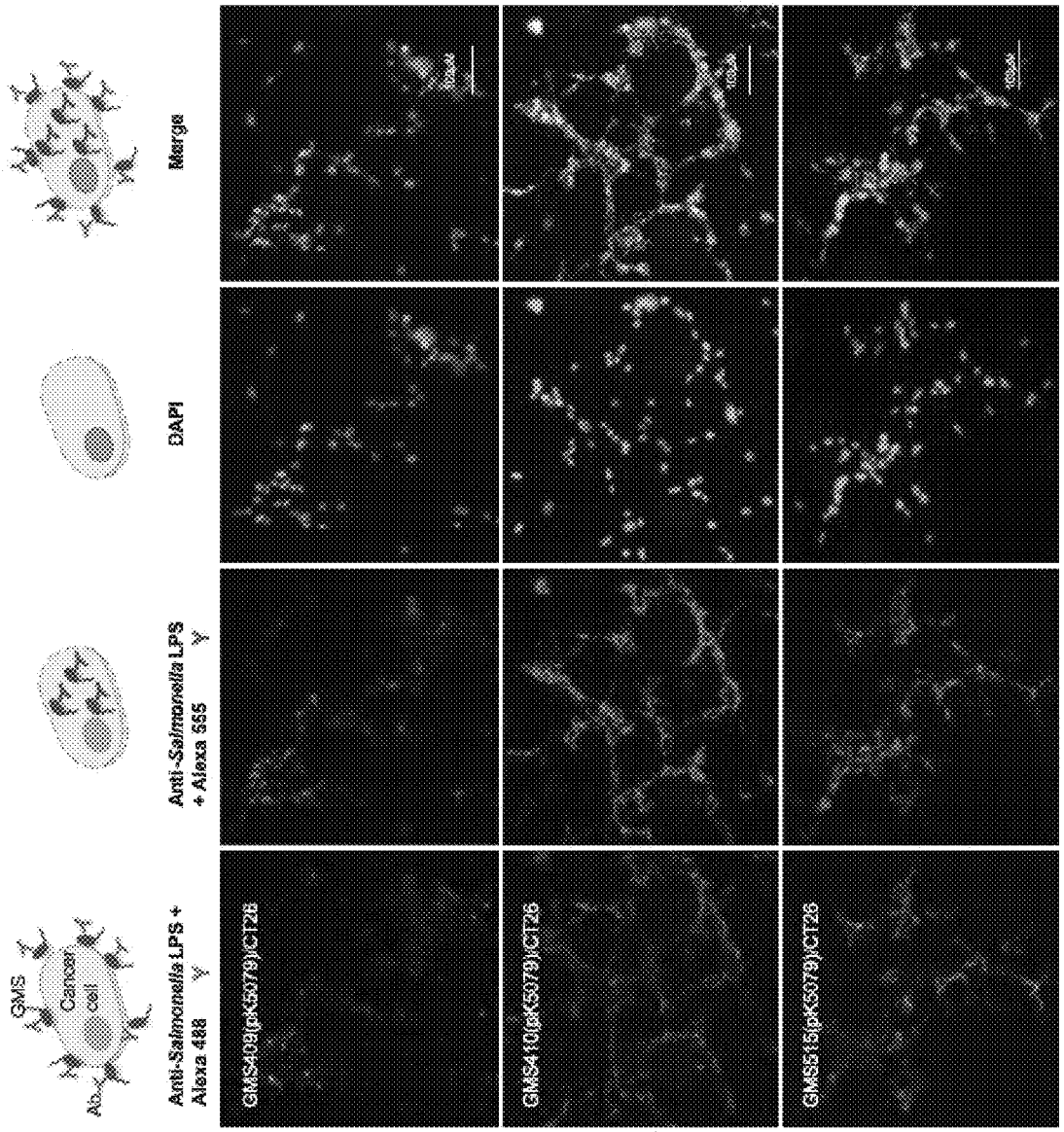

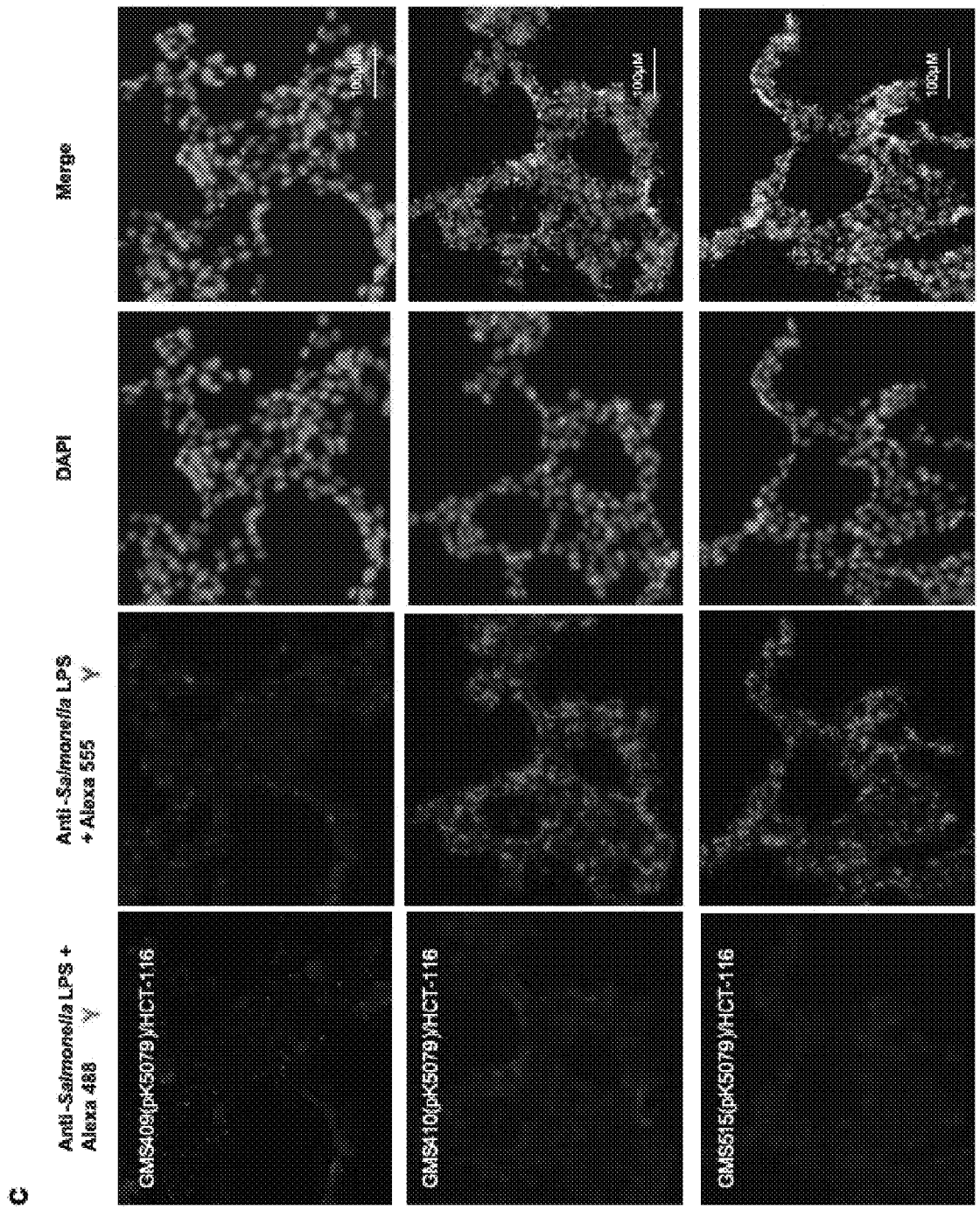

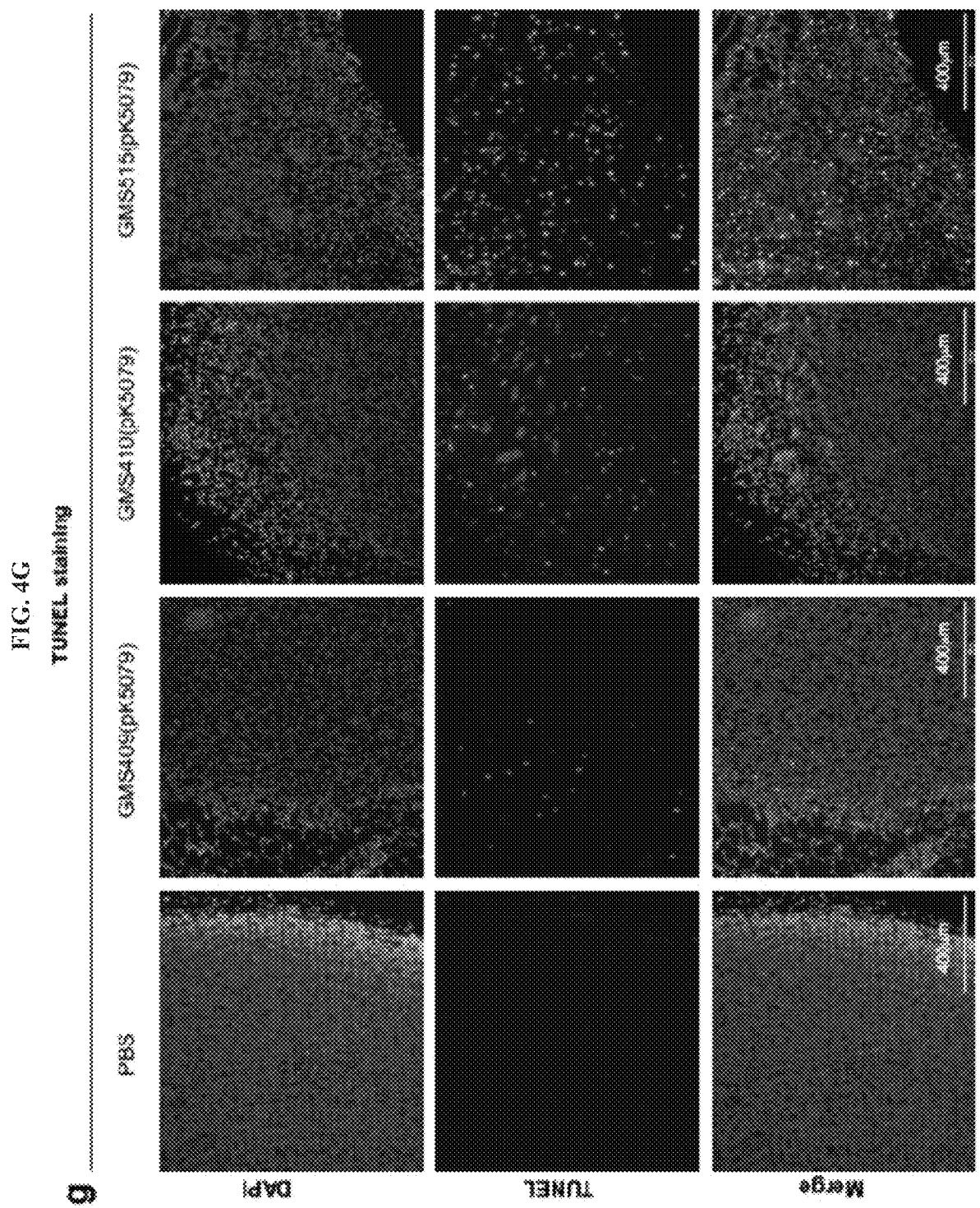
FIG. 4G TUNEL staining

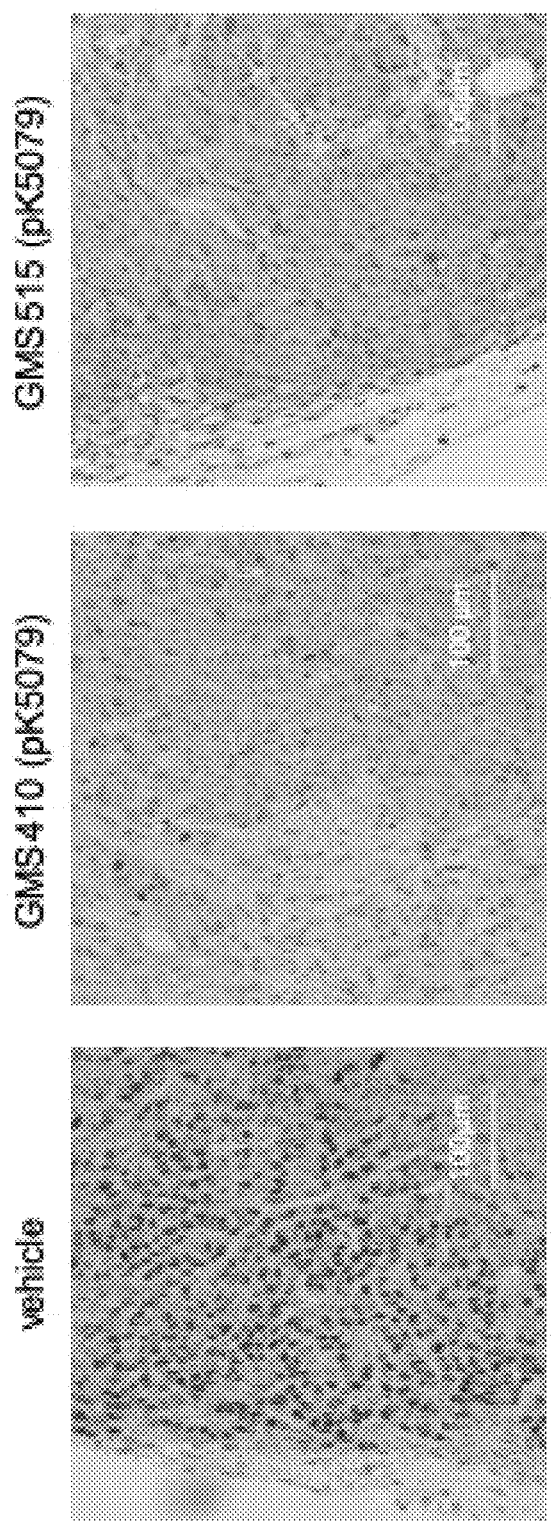

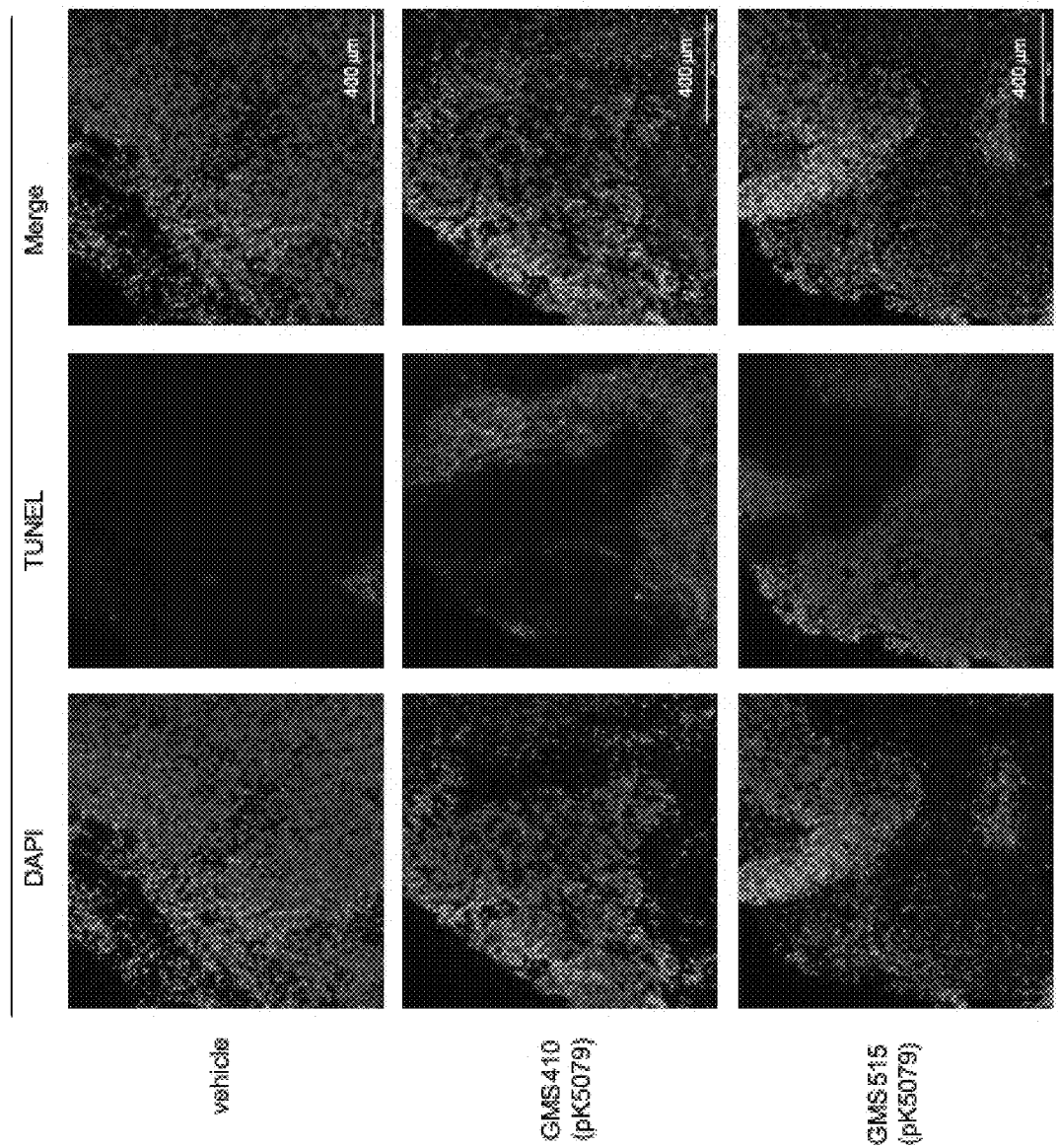

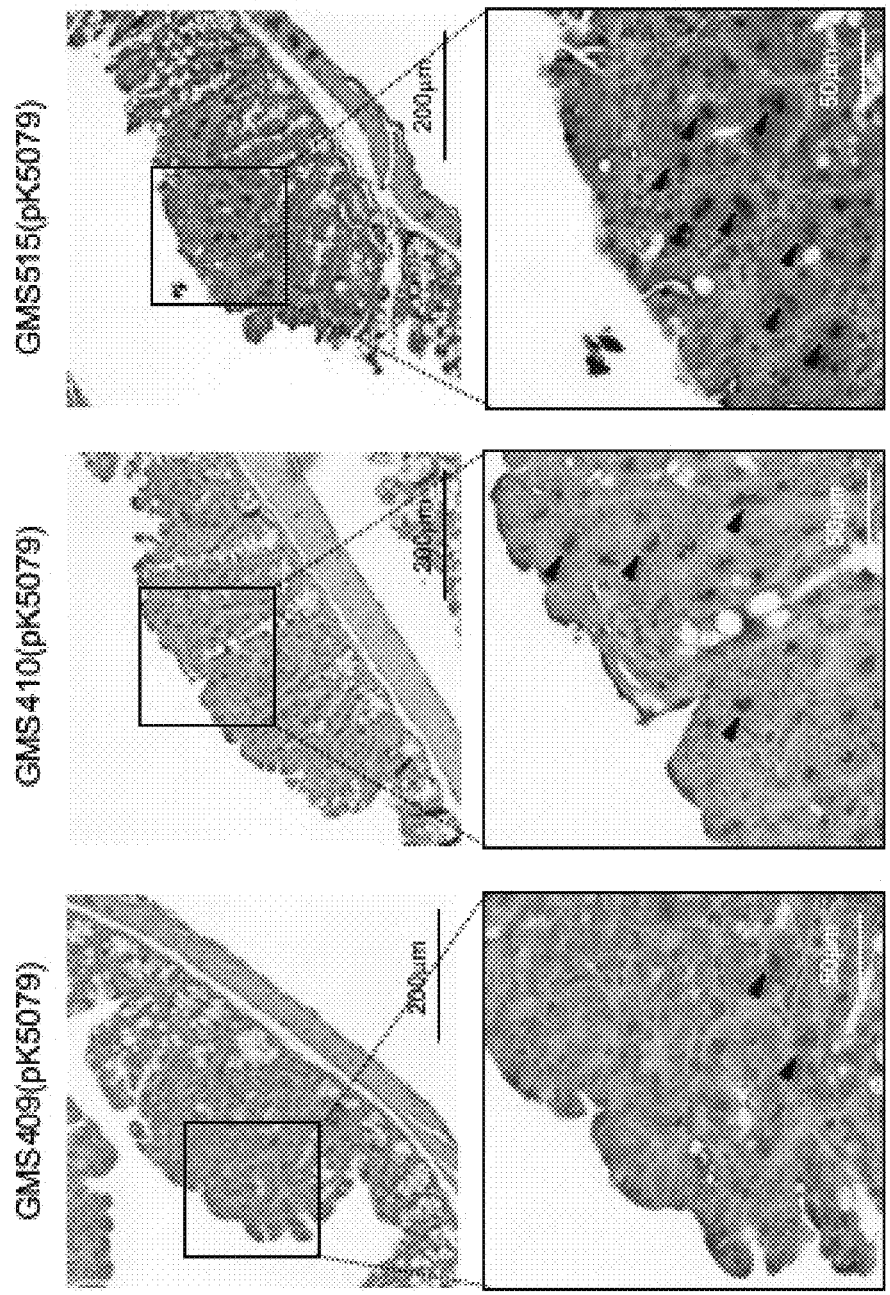

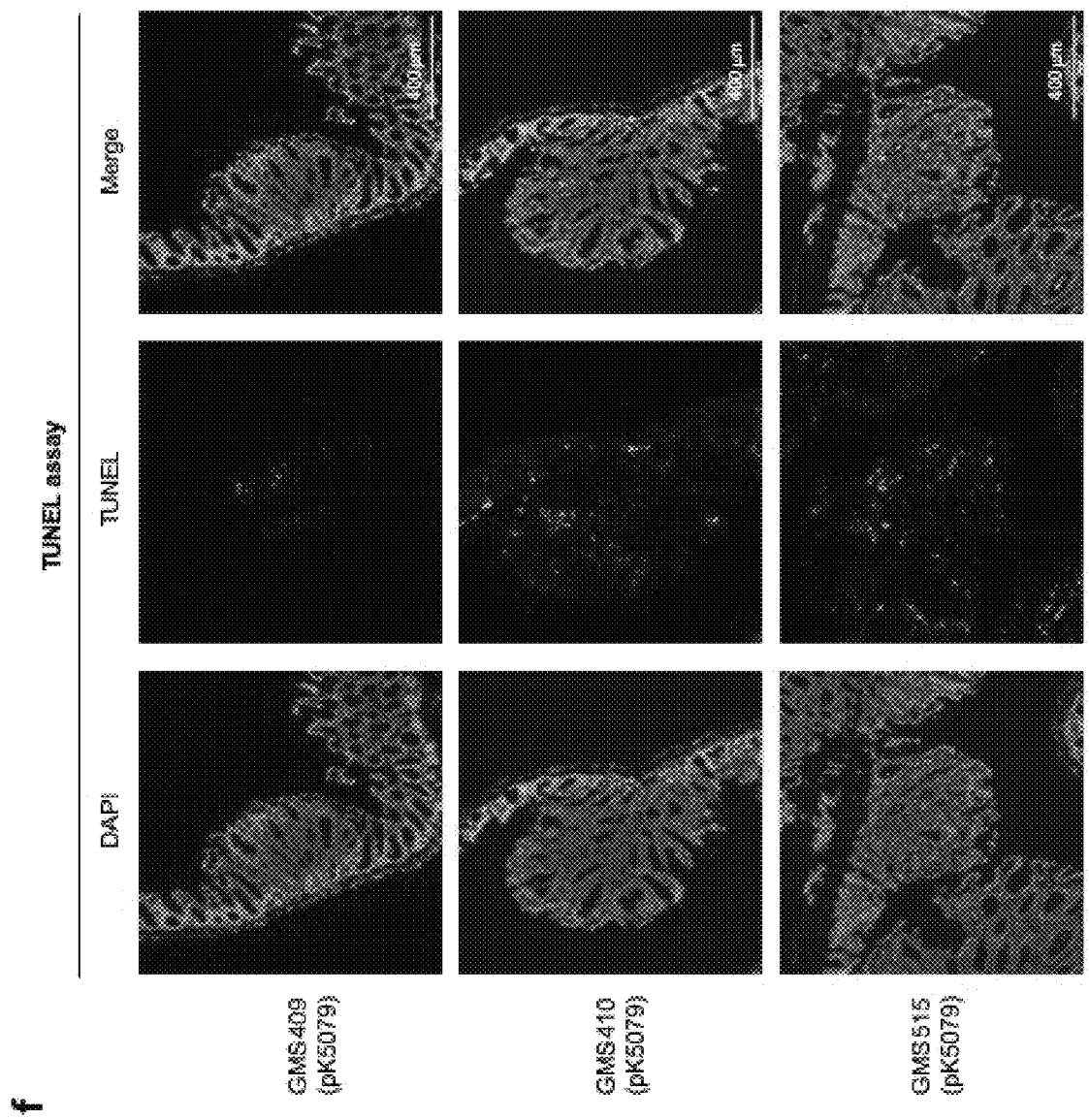

FIGS. 9A-9B
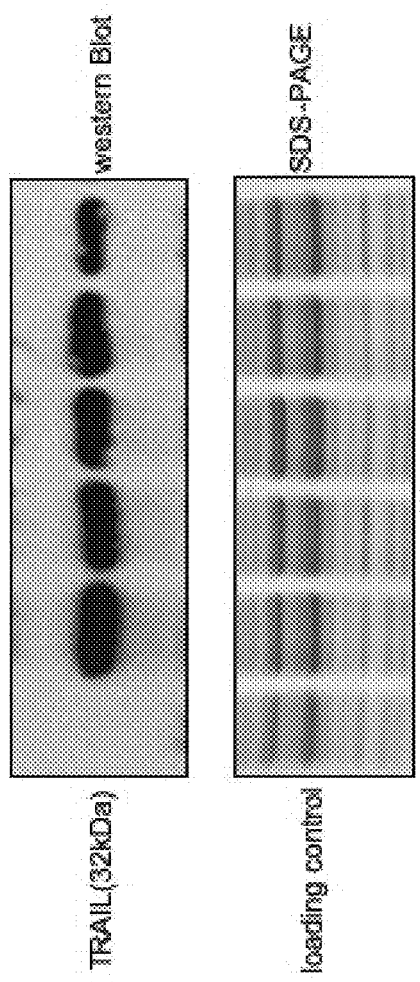
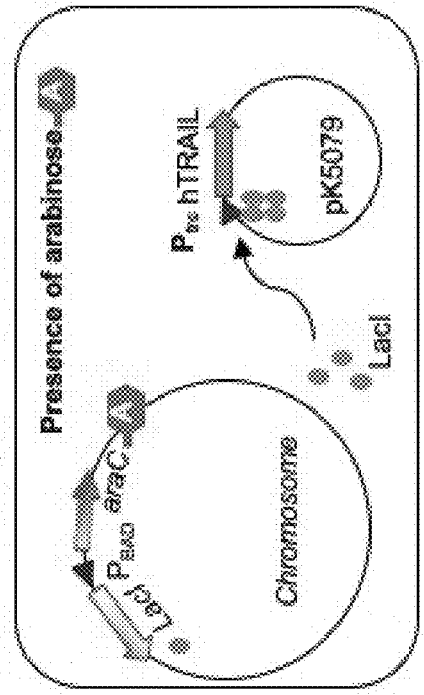
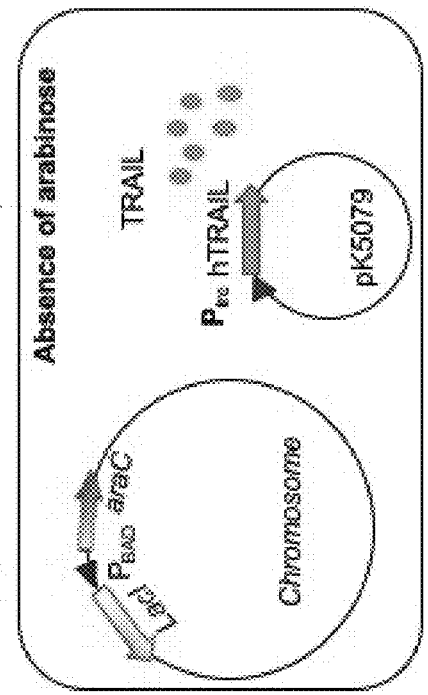

TUMOR-NAVIGATING, SELF-ERADICATING, TRAIL-ARMED SALMONELLA FOR PRECISION CANCER THERAPY

REFERENCE TO THE SEQUENCE LISTING

This application is being filed electronically via EFS-Web and includes an electronically submitted Sequence Listing in .txt format. The .txt file contains a sequence listing entitled "2020-02-20_112624-01160 ST25.txt" created on Jan. 24, 2020 and is 75,448 bytes in size. The Sequence Listing contained in this .txt file is part of the specification and is hereby incorporated by reference herein in its entirety.

CROSS-REFERENCE TO RELATED APPLICATIONS

This application is a national stage application filed under 35 U.S.C. §371 of International Application No. PCT/US2020/019111, filed Feb. 20, 2020, which claims the benefit of U.S. Provisional Application Ser. No. 62/809,222, filed Feb. 22, 2019, both of which are incorporated by reference herein as if set forth in their entirety.

STATEMENT REGARDING FEDERALLY FUNDED RESEARCH OR DEVELOPMENT

This invention was made with government support under R21 CA152456 awarded by the National Institutes of Health. The government has certain rights in the invention.

BACKGROUND

Despite many advances in conventional methods such as chemo- and radiation-therapy, cancer treatment is still far from optimal. Current cancer therapies frequently encounter challenges including nonspecific systemic distribution of antitumor agents, inadequate drug concentrations reaching the tumor site, intolerable cytotoxicity and development of multiple drug resistance. Oncolytic bacterial therapy has been extensively studied in recent years to fill the critical unmet needs of cancer patients, where the current treatment options have been exhausted. The self-propelling feature of facultative anaerobe bacteria enables them to establish and maintain a high density in the tumor tissue. *Salmonella Typhimurium* showed a pronounced potential for cancer treatment since they preferably accumulate in large established tumors leading to active suppression of tumor growth. In addition, *S. Typhimurium* exhibits the properties to invade and affect metastases. However, the mechanism of oncolytic *Salmonella*-based therapy in vivo, especially the toxicity caused by *Salmonella* infection and tumor lysis, is not yet clearly understood. Although the current therapeutic *Salmonella* strains were most often modified to reduce virulence factors and endotoxins, the accomplishment of tumor-navigating and self-eradicating of *Salmonella* remains the critical challenge for *Salmonella*-based cancer treatment.

Currently, there is a need for improvements to existing oncolytic bacteria-based cancer treatments and, in particular, there is a need to develop new therapeutic methods that achieve precision tumor-navigating and self-eradication of oncolytic *Salmonella*.

SUMMARY OF THE DISCLOSURE

The present disclosure addresses the aforementioned drawbacks of conventional methods for treating cancer. In a first aspect, provided herein is a genetically modified *Salmonella* bacterium, where the bacterium comprises a recombinant gene encoding human TRAIL. Also provided herein is a genetically modified *Salmonella* bacterium, where the bacterium comprises a recombinant gene encoding for increased expression of a methyl-accepting chemotaxis protein (MCP). Also provided herein is a genetically modified *Salmonella* bacterium, where the bacterium comprises a recombinant gene encoding for reduced toxicity of the bacterium in a plurality of non-tumor cells. The bacterium can comprise a recombinant gene encoding human TNF-related Apoptosis-inducing Ligand (TRAIL); the following mutations $\Delta P_{murA}$::TT araC $P_{BAD}$ murA $\Delta$asd:: TT araC $P_{BAD}$ c2 $\Delta$(araC $P_{BAD}$)::P22 $P_R$ araBAD $\Delta$(wza-wcaM) $\Delta$pmi $\Delta$relA::araC $P_{BAD}$ lacI TT $\Delta$pagP::$P_{lpp}$pxE $\Delta$endA; and one or more of the following mutations: $\Delta P_{murA}$:: $P_{trc\ \Delta lacO}$tar, $\Delta$Ptsr::$P_{trc\ \Delta lacO}$ tsr, and $\Delta$trg. In some cases, the genetically modified *Salmonella* bacterium further comprises a recombinant gene encoding for reduced toxicity of the bacterium in a plurality of non-tumor cells and for toxicity of the bacterium in tumor cells, whereby the modified bacterium is capable of self-eradication in non-tumor cells. The genetically modified *Salmonella* (GMS) bacterium can comprise mutations $\Delta P_{tar}$::$P_{trc\ \Delta lacO}$tar, $\Delta P_{tsr}$: $P_{trc\ \Delta lacO}$ tsr, and $\Delta$trg. The bacterium can comprise pK5079 (SEQ ID NO:7). The genetically modified *Salmonella* bacterium can be strain GMS410(pK5079). The genetically modified *Salmonella* bacterium can be bacterium is strain GMS515(pK5079). The bacterium can be *S. Typhimurium*.

In another aspect provided herein is a method of treating cancer in a subject in need thereof. The method can comprise or consist essentially of administering a genetically modified *Salmonella* bacterium of this disclosure to the subject, whereby the genetically modified *Salmonella* bacterium treats cancer in the subject. Administering can comprise oral administration or intra-tumoral injection of the genetically modified *Salmonella* bacterium.

In a further aspect, provided herein is a method for stimulating tumoricidal activity in a subject. The method can comprise or consist essentially of administering a genetically modified *Salmonella* bacterium of this disclosure to the subject, whereby the genetically modified *Salmonella* bacterium induces tumoricidal activity in the subject. Administering can comprise oral administration or intra-tumoral injection of the genetically modified *Salmonella* bacterium. The subject can have cancer.

These and other advantages and features of the present disclosure will become more apparent from the following detailed description of the preferred embodiments of the present disclosure when viewed in conjunction with the accompanying drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 2a-2c demonstrate improved tumor-navigating, attaching, and invading ability in self-eradicating TRAIL-delivering GMS strain. a. Transwell assay (illustrated in the left) to determine the colony-forming units (CFU) of *Salmonella* swimming across the swimming agar toward mouse colon cancer cell CT-26 (middle, **p<0.01) and human colon cancer cell HCT-116 (right, *p<0.05, ****p<0.0001). The data presented are representatives of three independent experiments. b. *Salmonella* attachment and invasion assay through anti-*Salmonella* antibody immunofluorescence staining. Green, red, and blue fluorescence indicate *Salmonella* attached to CT-26 cell surface, *Salmonella* internalized into CT-26 cell, and nucleus of CT-26 cell, respectively. c. Immunofluorescence staining. Green, red, and blue fluorescence indicate *Salmonella* attached to HCT-116 cell surface, *Salmonella* internalized into HCT-116 cell, nucleus of HCT-116 cells, respectively.

FIGS. 4a-4h demonstrate that reprogrammed GMS strains favored tumor accumulation in CT-26 SQ tumor model and suppressed tumor growth in vivo. a. Schematic illustration of the events of tumor regression of reprogrammed GMS in CT-26 SQ tumor model. b. Schematic route and timeline of GMS-based therapy. c. Reprogrammed GMS strains favored tumor accumulation versus spleen (n=3, *p<0.05, ***p <0.001). d. The growth curve of SQ CT-26 tumor in BALB/c mice following IT injection of PBS or GMS strains, as described in 4b. The error bar indicates ±SEM. (n=11, p<0.05). e. Survival fraction curves for the mice described in 4b. Death was recorded post-treatments. In addition, the mice were euthanized when tumor size had reached a volume of more than 2 cm³ followed the guideline, and then considered as death (n =11, ρ<0.01). f. The representative immunostaining of Ki67 (dark brown in nucleus) in CT-26 tumor section of BALB/c mice described in 4b. g. TUNEL staining (green) in CT-26 tumor section of BALB/c mice described in 4b. Nucleus staining is blue color. h. Frequencies of isolated intra-tumoral CD107a⁺CD8⁺T cells (upper, left panel, p=0.018), IFNγ⁺CD8⁺T cells (upper, right panel, p=0.033), Ki67 positive cell in NK cells (lower, left panel, p=0.045), and IFNγ⁺ positive cell in NK cells (lower, right panel, p=0.038) from mice bearing tumors treated with PBS (n=4 tumors) and GMS (n=4 tumors).

FIGS. 5a-5e demonstrate reprogrammed GMS strains suppressed tumor growth in HCT-116 SQ tumor model in vivo. a. Schematic route and timeline of GMS-based therapy. b. A set of representative live imaging of NSG™ mice with SQ injected HCT-116 cells captured before and after GMS strain IT injections, as described in 5a. c. Luciferase activities of tumor cells from NSG™ mice before and after GMS strain IT injections were analyzed. The error bar indicates SEM. (n=6, *p<0.05). Experiments were repeated independently for three times. d. The representative immunostaining of Ki67 staining of the tumor sections of NSG™ mice described in 5a. e. TUNEL staining of the tumor sections of NSG™ mice described in 5a.

FIGS. 6a-6g demonstrate reprogrammed GMS strains suppressed tumor progression by promoting cancer cell-killing in a transgenic colon tumor mouse model. a. Schematic route and timeline of GMS-based therapy. b. The representative image of colon from Apc$^{flox/flox}$/CDX2-CRE mice orally inoculated with PBS or GMS strains, as described in 6a. c. Numbers of polyps from colons of Apc$^{flox/flox}$/CDX2-CRE mice described in 6a. The error bar indicates SEM. (n=8, **ρ<0.0001). d. Survival fraction curves of Apc$^{flox/flox}$/CDX2-CRE mice orally treated with PBS or GMS strains 3 times at 10 days interval (n=7, **p<0.0001). e. The representative *Salmonella* staining (dark brown) in polyps from colons and rectums of Apc$^{flox/flox}$/CDX2-CRE mice described in 6a. f. TUNEL staining (green) in polyps from colons and rectums of Apc$^{flox/flox}$/CDX2-CRE mice described in 6a. g. Polyps were isolated from Apc$^{flox/flox}$/CDX2-CRE mice on day ten post-treatment, and then weighed, minced, and digested. Tumor-infiltrating lymphocytes were isolated for flow cytometry analysis: NK cells (left panel) and CD8⁺ T cells (right panel). The error bar indicates SEM. (n=5, ***p<0.001).

FIGS. 9a-9c are schematic illustrations of regulatory interactions on TRAIL expression and delivery. a. A schematic diagram of regulatory interactions for delayed TRAIL synthesis in the pK5079 harboring GMS strains. LacI, expressed from a chromosomal arabinose-regulated repressor gene, regulates the TRAIL expression from Ptrc promoter in pK5079. In the presence of arabinose (top), LacI is produced, which block TRAIL synthesis. In vivo, an arabinose-poor environment (bottom), the concentration of LacI decreases with each bacterial cell division, allowing increased TRAIL synthesis. b. Western blotting assay showing TRAIL expressions in strains GMS409(pK5079), GMS410(pK5079), GMS515(pK5079), and their precursor strains using an antibody against human TRAIL. Strain χ11021 (pYA3681) is an empty plasmid control. c. A schematic diagram of regulatory interactions for TRAIL delivery. In the presence of arabinose, asdA, murA, and c2 are transcribed, allowing for bacterial growth and repression of the P22 PR promoter by C2. In the absence of arabinose, the $P_{BAD}$ promoters cease to be active, with no further synthesis of Asd and MurA or C2. The concentrations of Asd, MurA, and C2 decrease due to cell division, leading to reduced synthesis of DAP, muramic acid, and imbalanced synthesis of the rigid layer of the cell wall. As the C2 concentration drops, P22 $P_R$ is de-repressed, resulting in $P_R$-directed synthesis of antisense mRNA, which blocks translation of residual asdA and murA mRNA. These concerted activities lead to cell lysis and release of TRAIL.

DETAILED DESCRIPTION

Figure 1A:
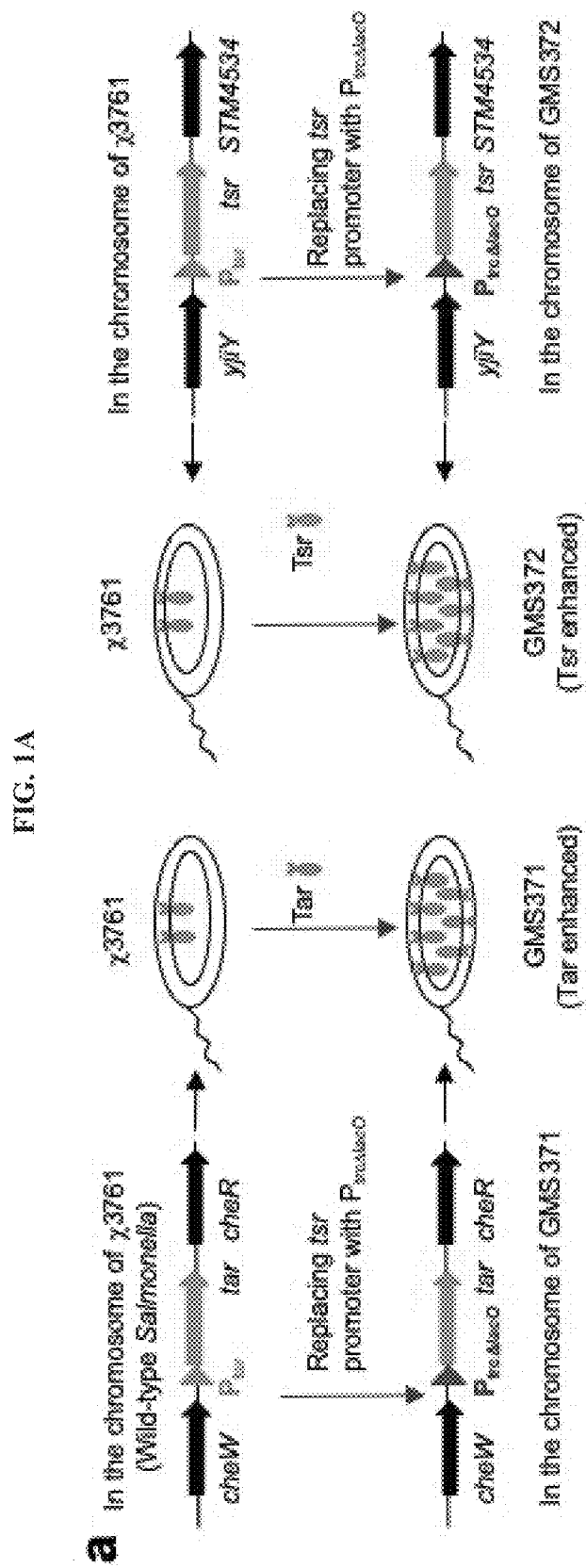
FIGS. 1a-1e demonstrate that genetic manipulation of *Salmonella* chemoreceptor synthesis enhanced beneficial chemotaxis for tumor-navigation. a. Schematic illustration of experimental design to confer high level constitutive chemoreceptor synthesis. b. Growth curves of *Salmonella* chemoreceptor-enhanced strains GMS371, GMS372, and their wild-type parent χ3761. Data are presented as the means, and the error bar represents the standard deviation (SD) from three independent experiments. c. Swimming rate of strains GMS371, GMS372, and x3761. Shown are the means of distance *Salmonella* traveled on swimming agar plates and SD from three independent experiments. d. Chemotaxis assay of strains GMS371 and χ3761 with aspartate as a chemoattractant. The representative images (left) of χ3761 (top) and GMS371 (bottom) were captured after 12 h of incubation. Histogram (right) of swim ring size represents three independent experiments, each in triplicate. Error bars represent SD (n=3, *p=0.03). e. Chemotaxis assay of strains GMS372 and χ3761 with serine as a chemoattractant. The picture (left) presented is a representative image of χ3761 (top) and GMS372 (bottom). Histogram data (right) are presented as the means of swimming distance, and the SD is from three independent experiments (n=4, **p =0.002).
Figures 1B, 1C:
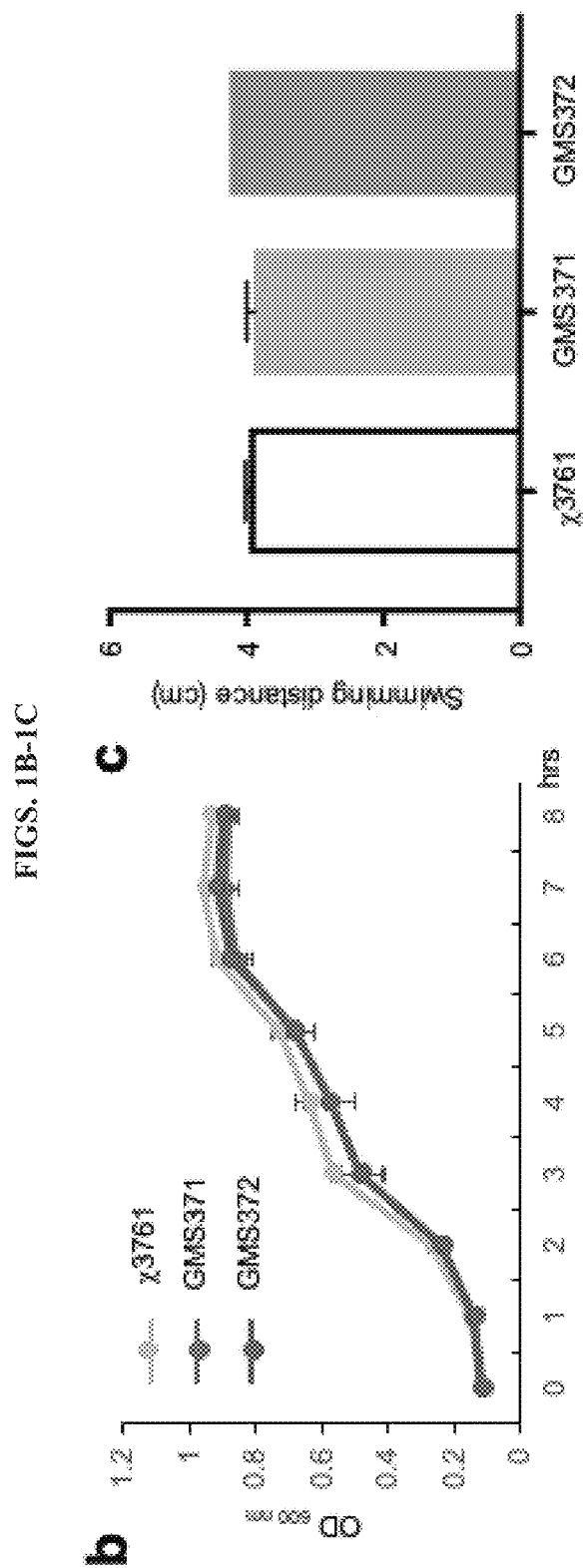
Figures 1D, 1E:
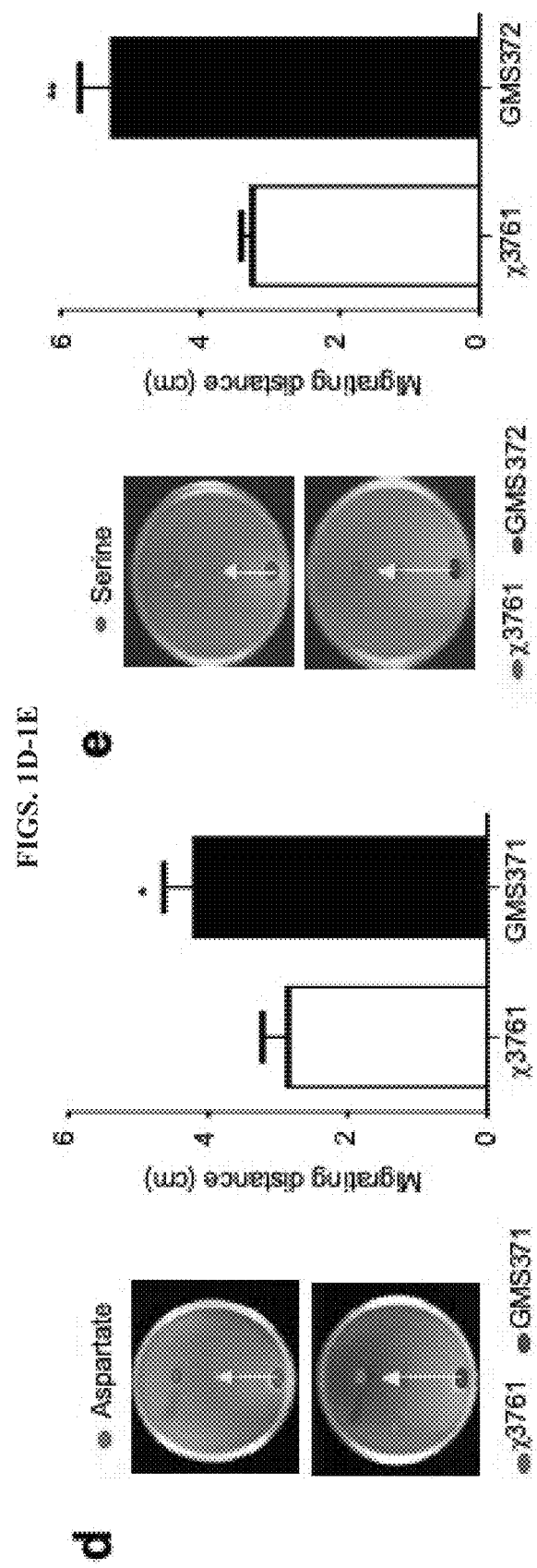

The present disclosure addresses the aforementioned drawbacks of conventional methods for treating cancer, including current uses of oncolytic bacteria in cancer treatments. In particular, the methods and compositions described herein are based at least in part on the inventor's development of genetically modified *Salmonella* (GMS) capable of precise navigation to tumors and self-eradication. The GMS described herein armed with TRAIL to trigger cancer cell apoptosis. As demonstrated in the Examples, genetically modified *Salmonella* of this disclosure navigate to cancer cells, self-lyse, release TRAIL, and induce cancer cell apoptosis in vitro. Moreover, intratumorally injected GMS effectively suppress subcutaneous tumor growth, and orally administrated GMS reduce the number of polyps and prolong lifespan in an in vivo model of colon cancer.

Accordingly, in a first aspect, provided herein is a genetically modified *Salmonella* bacterium, where the bacterium comprises a recombinant gene encoding human TRAIL. Also provided herein is a genetically modified *Salmonella* bacterium, where the bacterium comprises a recombinant gene encoding for increased expression of a methyl-accepting chemotaxis protein (MCP). Also provided herein is a genetically modified *Salmonella* bacterium, where the bacterium comprises a recombinant gene encoding for reduced toxicity of the bacterium in a plurality of non-tumor cells.

In some cases, the genetically modified *Salmonella* bacterium comprises a first recombinant gene encoding human TRAIL, a second recombinant gene encoding for increased expression of a methyl-accepting chemotaxis protein (MCP), and a third recombinant gene encoding for reduced toxicity of the bacterium in a plurality of non-tumor cells. Such genetically modified *Salmonella* bacteria are capable of self-eradication in vivo. Such GMS also exhibit increased chemotaxis to tumor cells and increased tumoricidal activity relative to a *Salmonella* bacterium not comprising the first recombinant gene. As demonstrated in the Examples, lysis of the genetically modified *Salmonella* of this disclosure releases TRAIL, thus inducing apoptosis of cancer cells targeted by the modified bacteria. In some cases, other members of the tumor necrosis factor family, such as Tumor Necrosis Factor α (TNFα) and Fas Ligand (FasL), may be used in place of TRAIL. In such cases, TNFα or FasL is released by lysis of the genetically modified *Salmonella* to induce apoptosis of cancer cells targeted by the modified bacteria.

As used herein, the terms "genetically modified" and "genetically engineered" are used interchangeably and refer to a prokaryotic cell that includes an exogenous polynucleotide, regardless of the method used for insertion. In some cases, the cell has been modified to comprise a non-naturally occurring nucleic acid molecule that has been created or modified by the hand of man (e.g., using recombinant DNA technology) or is derived from such a molecule (e.g., by transcription, translation, etc.). A cell that contains an exogenous, recombinant, synthetic, and/or otherwise modified polynucleotide is considered to be an engineered cell. The term "altered," as used herein, refers to any change in the nucleic acid sequence that results in the nucleic acid sequence not being expressed. In an exemplary embodiment, the alteration results in the nucleic acid sequence not being expressed in a host. In one embodiment, the alteration is a deletion. In another embodiment, the alteration places an exogenous nucleic acid under the control of a regulatable promoter, such that the nucleic acid is not expressed in a host.

Some embodiments of the instant disclosure comprise a species or subspecies of the *Salmonella* genera. For instance, the recombinant bacterium may be a *Salmonella Enterica* serovar. In an exemplary embodiment, a bacterium of the disclosure may be derived from (i.e., an isolate of) *S. Enterica* serovar Typhimurium, referred to herein as *Salmonella Typhimurium*, and also from *S. Typhi, S. Paratyphi, S. Enteritidis, S. Choleraesius, S. Arizona*, or *S. Dublin*. In an exemplary embodiment, the recombinant bacterium is derived from *S. Typhimurium*. As used herein, "*Salmonella Typhimurium*" refers to an isolate of *Salmonella Typhimurium*. Likewise, the terms "*S. Typhi,*" "*S. Paratyphi,*" "*S. Enteritidis,*" "*S. Choleraesius,*" "*S. Arizona*," and "*S. Dublin*" as used herein refer to isolates of *Salmonella Typhi, S. Paratyphi, S. Enteritidis, S. Choleraesius, S. Arizona*, and *S. Dublin*, respectively. As used herein the terms "strain" and "isolate" are used interchangeably.

As described and demonstrated herein, *Salmonella* are genetically modified to increase navigation of the bacteria to cancer cells (tumor cells) by modulating the expression of MCP, which are transmembrane chemoreceptors important for taxis (bacterial movement) toward or away from particular substrates. *Salmonella* MCPs include Tar (taxis towards aspartate and maltose, away from nickel and cobalt; aka cheM), Tsr (taxis towards serine, away from leucine, indole and weak acids), Trg (taxis towards sugars, galactose and ribose), Tap (taxis towards dipeptides), McpC (repellent response towards L-cystine), Tip, McpA, and McpB. The coding sequence of Tsr (Methyl-accepting chemotaxis protein) of *Salmonella Typhimurium* is accession number A0A0H3NL96. The coding sequence of Tar (Methyl-accepting chemotaxis protein II) of *S. Typhimurium* is accession number P02941.

Figure 10:
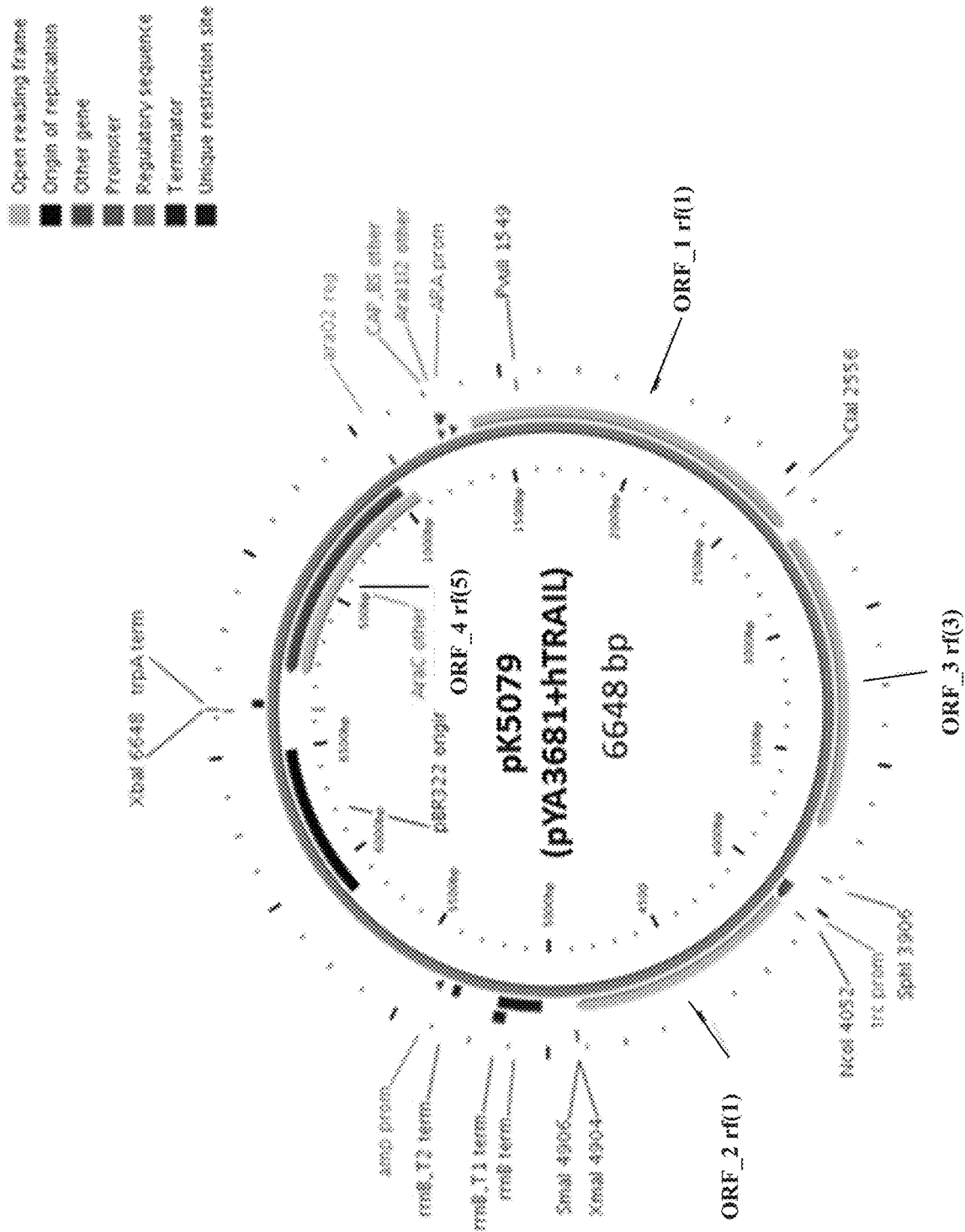
FIG. 10 is an illustration of a plasmid map for pK5079.

In some cases, a recombinant bacterium of this disclosure is engineered for increased chemotaxis toward tumor cells by increasing expression of Tar and/or increasing expression or Tsr. In some cases, the genetic modification further comprise reducing expression of Trg. For example, a bacterium can be genetically altered to produce modified *Salmonella* having constitutive over-expression of one or more chemoreceptors such as Tar and Tsr. In some cases, a genetically modified *Salmonella* bacterium comprises mutation $\Delta P_{tar}::P_{trc\ \Delta lacO}$ tar. In other cases, the genetically modified *Salmonella* bacterium comprises mutations $\Delta P_{tar}::P_{trc\ \Delta lacO}$ tar, tsr: $\Delta P_{tsr}::P_{trc\ \Delta lacO}$tsr, and $\Delta$trg. In some cases, the genetically modified *Salmonella bacterium* is from strain GMS410(pK5079) or GMS515(pK5079). A plasmid map for pK5079 is provided in FIG. 10. Such strains include self-eradication vectors, TRAIL, and MCP mutations described herein for increased chemotaxis to tumor cells.

In certain embodiments, a recombinant bacterium of the disclosure may also be attenuated. As used herein, the term "attenuated" refers to the state of the bacterium wherein the bacterium has been weakened from its wild-type fitness by some form of recombinant or physical manipulation such that the bacterium's virulence is reduced relative to a control (a non-recombinant/non-manipulated bacterium). This includes altering the genotype of the bacterium to reduce its ability to cause disease. However, the bacterium's ability to colonize the tumor is, preferably, not substantially compromised. For instance, in one embodiment, regulated attenuation allows the recombinant bacterium to express one or more nucleic acids encoding products important for the bacterium to withstand stresses encountered in the host after immunization. This allows efficient invasion and colonization of tumor tissues before the recombinant bacterium is regulated to display the attenuated phenotype. As used herein in this context, the term "reduce/reduced" means a reduction of at least 10%, preferably 25%, even more preferably 50%, still more preferably 60%, even more preferably 70%, still more preferably 80%, even more preferably 90% and most preferably of 100% as compared to the appropriate control.

For genetically modified *Salmonella*, non-limiting examples of nucleic acid sequences which may be used for attenuation include: a pab nucleic acid sequence, a pur nucleic acid sequence, an aro nucleic acid sequence, an asdA nucleic acid sequence, murA, nadA, pncB, galE, pmi, fur, rpsL, ompR, htrA, hemA, cdt, cya, crp, dam, phoP, phoQ, rfc, poxA, galU, mviA, sodC, recA, ssrA, sirA, inv, hilA, rpoE, figM, tonB, slyA, and any combination thereof. Generally, the nucleic acids provided above as non-limiting examples encode "attenuation proteins," meaning any protein the absence of which attenuates a bacterium. The "$\Delta$" as used herein, refers to gene deletion. The "::" as used herein, refers to gene insertion. The "asd" refers to a gene encoding aspartate-semialdehyde dehydrogenase. The asd mutants ("$\Delta$asd") of Gram-negative bacteria have an obligate requirement for diaminopimelic acid (DAP), which is an essential constituent of the peptidoglycan layer of the cell wall of these organisms. The "murA" refers to a gene required for the synthesis of the peptidoglycan layer of the bacterial cell wall. Like asdA mutants, murA mutants ("$\Delta$murA") are deficient in bacterial cell wall synthesis.

In some cases, the genetically modified bacterium is further modified such that the recombinant bacterium is capable of regulated attenuation. Generally speaking, the bacterium comprises a chromosomally integrated regulatable promoter. The promoter replaces the native promoter of, and is operably linked to, at least one nucleic acid sequence encoding an attenuation protein, such that the absence of the function of the protein renders the bacterium attenuated. In some embodiments, the promoter is modified to optimize the regulated attenuation.

In some cases, the genetically modified bacterium is further modified such that the recombinant bacterium exhibits a reduced expression of immunosuppressive membrane proteins, which are typically overexpressed during *Salmonella* infection. Generally speaking, the bacterium comprises chromosomal gene mutations, largely originates from the *Salmonella* pathogenicity island 2 (SPI2), which encodes proteins associated with induction of programmed death ligand 1 (PD-L1) expression. PD-L1 is an immunosuppressive membrane protein that binds to T cells via the PD-1 receptor and thereby halts their activation. PD-L1 expression plays an essential role in the immunological tolerance of self-antigens but is also exploited for immune evasion by pathogen-infected cells and cancer cells. It has been demonstrated that *Salmonella* infection of intestinal epithelial cells combined with gamma interferon (IFN$\gamma$) causes the synergistic induction of PD-L1. The increased expression of PD-L1 through *Salmonella* infection was seen in both human and rat intestinal epithelial cell lines. It was determined that cellular invasion by the bacteria is necessary for PD-L1 induction, potentially indicating that *Salmonella* strains are delivering mediators from inside the host cell that triggers the increased PD-L1 expression. In addition, *Salmonella* plus IFN$\gamma$ induction of PD-L1 decreased the cytokine production of activated T cells. Knockout mutants, including but not limited $\Delta$sseL, $\Delta$spvD or $\Delta$ssrAB, cause the absence of the function of specific proteins to prevent the induction of PD-L1 expression. In some embodiments, the mutations are combined to maximize the effect of selected mutations. In some cases, a genetically modified *Salmonella* bacterium comprises one or more mutations selected from $\Delta$sseL, $\Delta$spvD, and/or $\Delta$ssrAB. The term "sseL" refers to a gene encoding sulfatase/phosphatase/protease, which acts as a deubiquitinase in infected host cells. The term "spvD" refers to a gene encoding cysteine hydrolase, which negatively regulates the NF-κB signaling pathway and promotes virulence of *S. Typhimurium* in mice. The term "ssrAB" refers to chromosomal loci located within SPI-2, which encodes two-component regulatory system SsrAB, which regulates the expression of several operons in SPI-2 and, in addition, a large number of genes for non-SPI2-encoded effector proteins.

In another aspect, provided herein are methods for producing genetically modified *Salmonella* bacteria having increased tumoricidal activity. In exemplary embodiments, the method comprises: transforming a first recombinant gene into a regulated attenuation strain of *Salmonella* forming a strain B, the first recombinant gene encoding for chemotaxis of the strain B toward a plurality of tumor cells; transforming a second recombinant gene into the strain B forming a strain C, the second recombinant gene encoding for (i) reduced toxicity of strain C in a plurality of non-tumor cells; and (ii) toxicity of strain C in the plurality of tumor cells; and transforming a third recombinant gene into the strain C forming a strain D, the third recombinant gene encoding for activation of tumoricidal activity. In some cases, the first recombinant gene encodes for synthesis of Tar or synthesis of Tsr. Preferably, the third recombinant gene can encode human TRAIL. In some cases, strain D comprises mutation $\Delta P_{tar}::P_{trc\ \Delta lacO}$ tar, or comprises mutations $\Delta P_{tar}::P_{trc\ \Delta lacO}$ tar, $\Delta P_{tsr}::P_{trc\ \Delta lacO}$tsr, and $\Delta$trg. In some cases, strain D is GMS410(pK5079). In other cases, strain D is GMS515 (pK5079).

The genetically modified *Salmonella* described herein can be used in any of a variety of applications. For example, the genetically modified *Salmonella* can be used in therapeutic methods to treat cancer or a cancer-associated condition. In some cases, a method of treating cancer in a subject in need thereof will comprise administering an effective amount of a modified *Salmonella* bacterium having the genetic modifications described herein and, thus, being tumor navigating, self-eradicating, and armed with TRAIL to trigger tumor cell apoptosis, to the subject, whereby the genetically modified *Salmonella* bacterium treats cancer in the subject. As used herein, the term "effective amount" means, in the context of a composition, an amount of an immunogenic composition capable of inducing an immune response that reduces the incidence of or lessens the severity of infection or incident of disease in an animal. Alternatively, in the context of a therapy, the term "effective amount" refers to the amount of a therapy which is sufficient to reduce or ameliorate the severity or duration of a disease or disorder (e.g., cancer), or one or more symptoms thereof, prevent the advancement of a disease or disorder, cause the regression of a disease or disorder, prevent the recurrence, development, onset, or progression of one or more symptoms associated with a disease or disorder, or enhance or improve the prophylaxis or treatment of another therapy or therapeutic agent. The effective amount to be administered will depend upon the host receiving the modified bacteria as well as factors such as the size, weight, and age of the host.

As used herein, "subject" refers to an animal or a patient for whom the described treatment is intended. In exemplary embodiments, subjects treated according to the methods provided herein are human. In other cases, subjects treated according to the methods provided herein are non-human mammals, including by way of example and not limitation, members of rodentia (e.g., mouse, rat, guinea pig), lagomorpha (e.g., rabbits, hares), perissodactyla (e.g., horses, donkeys, etc.), artodactyla (e.g., pigs, cows, sheep), carnivora (e.g., cats, canines), and primates (e.g., apes, monkeys, baboons, and humans).

As used herein, the terms "treat" and "treating" refer to both therapeutic treatment and prophylactic or preventative measures, wherein the object is to treat, rescue, ameliorate, or otherwise lessen an undesired symptom or condition associated with cancer or any condition associated with aberrant cell proliferation. In some cases, the term "treated" refers to any beneficial effect on progression of a disease or condition. Beneficial effects can include reversing, alleviating, inhibiting the progress of, preventing, or reducing the likelihood of the disease or condition to which the term applies or one or more symptoms or manifestations of such a disease or condition. Where the disease or condition is a cancer or cancer-associated condition, treating can refer to the management and care of a patient for the purpose of combating cancer, and can include reversing, alleviating, inhibiting the progress of, preventing, or reducing the likelihood of, or lessening the severity of any aspect of the cancer or cancer-associated condition (e.g., metastasis, tumor growth). As used herein, the terms "preventing" and "prevent" refer not only to a complete prevention of a certain disease or condition, but also to partially or substantially attenuating, reducing the risk of, or delaying the development or recurrence of the disease or condition to which the term applies.

In some cases, the methods provided herein are directed to treating or preventing a cancer in a subject by administering a composition provided herein. In other cases, the present disclosure provides a method of inhibiting, retarding, or preventing growth of a tumor or tumor cells in a subject. In exemplary embodiments, colon cancer (colorectal cancer) is treated using the methods provided herein. Examples of other cancers appropriate for methods of treating or preventing as provided herein include, without limitation, lung cancer, pancreatic cancer, prostate cancer, skin cancer, bladder cancer, kidney cancer, ovarian cancer, colorectal cancer, breast cancer, cervical cancer, brain cancer, esophageal cancer, and stomach cancer. Other diseases or conditions appropriate for methods of treating or preventing as provided herein include, without limitation, lymphoma and chronic and acute leukemia.

Any appropriate route or mode of administration to the subject can be employed according to a method provided herein. In some cases, administering comprises oral administration of the genetically modified *Salmonella* bacterium. In other cases, administering comprises intra-tumoral injection of the genetically modified *Salmonella* bacterium. The mode of administration can be determined based on the physical location, type, or number of tumors in the subject's body.

Clinicians, physicians, and other health care professionals can administer genetically modified *Salmonella* bacteria to a subject in need thereof according to a method provided herein. In some cases, a single administration of the composition may be sufficient. In other cases, more than one administration of the composition is performed at various intervals (e.g., once per week, twice per week, daily, monthly) or according to any other appropriate treatment regimen. The duration of treatment can be a single dose or periodic multiple doses for as long as administration of a composition provided herein is tolerated by the subject.

Any appropriate method can be practiced to determine, detect, or monitor a subject's response to treatment according to a method provided herein. As used herein, "determining a subject's response to treatment" refers to the assessment of the results of a therapy in a subject in response to administration of a composition provided herein or to treatment according to a method provided herein. For example, a subject's condition can be monitored continuously or evaluated at appropriate time intervals (e.g., at regular or irregular time points) to detect and/or monitor any changes in disease progression (e.g., change in tumor size) as an indicator of the subject's response to a composition comprising genetically modified *Salmonella* bacteria as described herein. In some cases, tumors can be measured to detect or monitor any change in, for example, tumor size or tumor growth rate (e.g., tumor expansion or shrinkage, inhibited or accelerated tumor growth rate). For example, detection methods such as computed tomography (CT), magnetic resonance imaging (MRI) scanning, and x-ray (e.g., chest x-ray) can be used. In some cases, ultrasound examinations can be used to detect and measure tumor regression or to detect progression of lesions. In other cases, evaluation of a tumor can involve cytology or histology of, for example, biopsy samples. For solid tumors, evaluation of a subject's response to treatment as provided herein can include assessing RECIST ("Response Evaluation Criteria in Solid Tumors"). RECIST criteria can be used to evaluate a subject's response to the therapy used to treat their disease or condition. See, for review, Therasse et al., *J. Natl. Cancer Inst.* 92:205-16, 2000.

The term "promoter", as used herein, may mean a synthetic or naturally-derived molecule which is capable of conferring, activating or enhancing expression of a nucleic acid in a cell. A promoter may comprise one or more specific transcriptional regulatory sequences to further enhance expression and/or to alter the spatial expression and/or temporal expression of same.

The terms "nucleic acid" and "nucleic acid molecule," as used herein, refer to a compound comprising a nucleobase and an acidic moiety, e.g., a nucleoside, a nucleotide, or a polymer of nucleotides. Nucleic acids generally refer to polymers comprising nucleotides or nucleotide analogs joined together through backbone linkages such as but not limited to phosphodiester bonds. Nucleic acids include deoxyribonucleic acids (DNA) and ribonucleic acids (RNA) such as messenger RNA (mRNA), transfer RNA (tRNA), etc. Typically, polymeric nucleic acids, e.g., nucleic acid molecules comprising three or more nucleotides are linear molecules, in which adjacent nucleotides are linked to each other via a phosphodiester linkage. In some embodiments, "nucleic acid" refers to individual nucleic acid residues (e.g. nucleotides and/or nucleosides). In some embodiments, "nucleic acid" refers to an oligonucleotide chain comprising three or more individual nucleotide residues. As used herein, the terms "oligonucleotide" and "polynucleotide" can be used interchangeably to refer to a polymer of nucleotides (e.g., a string of at least three nucleotides). In some embodiments, "nucleic acid" encompasses RNA as well as single and/or double-stranded DNA. Nucleic acids may be naturally occurring, for example, in the context of a genome, a transcript, an mRNA, tRNA, rRNA, small interfering RNA (siRNA), small nuclear RNA (snRNA), a plasmid, cosmid, chromosome, chromatid, or other naturally occurring nucleic acid molecule. On the other hand, a nucleic acid molecule may be a non-naturally occurring molecule, e.g., a recombinant DNA or RNA, an artificial chromosome, an engineered genome, or fragment thereof, or a synthetic DNA, RNA, DNA/RNA hybrid, or include non-naturally occurring nucleotides or nucleosides. Furthermore, the terms "nucleic acid," "DNA," "RNA," and/or similar terms include nucleic acid analogs, i.e. analogs having other than a phosphodiester backbone. Nucleic acids can be purified from natural sources, produced using recombinant expression systems and optionally purified, chemically synthesized, etc. Where appropriate, e.g., in the case of chemically synthesized molecules, nucleic acids can comprise nucleoside analogs such as analogs having chemically modified bases or sugars, and backbone modifications. A nucleic acid sequence is presented in the 5' to 3' direction unless otherwise indicated. In some embodiments, a nucleic acid is or comprises natural nucleosides (e.g. adenosine, thymidine, guanosine, cytidine, uridine, deoxyadenosine, deoxythymidine, deoxyguanosine, and deoxycytidine); nucleoside analogs (e.g., 2-aminoadenosine, 2-thiothymidine, inosine, pyrrolo-pyrimidine, 3-methyl adenosine, 5-methylcytidine, 2-aminoadenosine, C5-bromouridine, C5-fluorouridine, C5-iodouridine, C5-propynyl-uridine, C5-propynyl-cytidine, C5-methylcytidine, 2-aminoadeno sine, 7-deazaadenosine, 7-deazaguanosine, 8-oxoadenosine, 8-oxoguanosine, O(6)-methylguanine, and 2-thiocytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages).

Nucleic acids and/or other constructs of the disclosure may be isolated. As used herein, "isolated" means to separate from at least some of the components with which it is usually associated whether it is derived from a naturally occurring source or made synthetically, in whole or in part.

The terms "protein," "peptide," and "polypeptide" are used interchangeably herein and refer to a polymer of amino acid residues linked together by peptide (amide) bonds. The terms refer to a protein, peptide, or polypeptide of any size, structure, or function. Typically, a protein, peptide, or polypeptide will be at least three amino acids long. A protein, peptide, or polypeptide may refer to an individual protein or a collection of proteins. One or more of the amino acids in a protein, peptide, or polypeptide may be modified, for example, by the addition of a chemical entity such as a carbohydrate group, a hydroxyl group, a phosphate group, a farnesyl group, an isofarnesyl group, a fatty acid group, a linker for conjugation, functionalization, or other modification, etc. A protein, peptide, or polypeptide may also be a single molecule or may be a multi-molecular complex. A protein, peptide, or polypeptide may be just a fragment of a naturally occurring protein or peptide. A protein, peptide, or polypeptide may be naturally occurring, recombinant, or synthetic, or any combination thereof. A protein may comprise different domains, for example, a nucleic acid binding domain and a nucleic acid cleavage domain. In some embodiments, a protein comprises a proteinaceous part, e.g., an amino acid sequence constituting a nucleic acid binding domain.

Nucleic acids, proteins, and/or other moieties of the disclosure may be purified. As used herein, purified means separate from the majority of other compounds or entities. A compound or moiety may be partially purified or substantially purified. Purity may be denoted by weight measure and may be determined using a variety of analytical techniques such as but not limited to mass spectrometry, HPLC, etc.

In interpreting this disclosure, all terms should be interpreted in the broadest possible manner consistent with the context. It is understood that certain adaptations of the disclosure described in this disclosure are a matter of routine optimization for those skilled in the art, and can be implemented without departing from the spirit of the disclosure, or the scope of the appended claims.

So that the compositions and methods provided herein may more readily be understood, certain terms are defined:

As used in this specification and the appended claims, the singular forms "a," "an," and "the" include plural references unless the context clearly dictates otherwise. Any reference to "or" herein is intended to encompass "and/or" unless otherwise stated.

The terms "comprising", "comprises" and "comprised of" as used herein are synonymous with "including", "includes" or "containing", "contains", and are inclusive or open-ended and do not exclude additional, non-recited members, elements, or method steps. The phraseology and terminology used herein is for the purpose of description and should not be regarded as limiting. The use of "including," "comprising," "having," "containing," "involving," and variations thereof, is meant to encompass the items listed thereafter and additional items. Embodiments referenced as "comprising" certain elements are also contemplated as "consisting essentially of" and "consisting of" those elements. Use of ordinal terms such as "first," "second," "third," etc., in the claims to modify a claim element does not by itself connote any priority, precedence, or order of one claim element over another or the temporal order in which acts of a method are performed. Ordinal terms are used merely as labels to distinguish one claim element having a certain name from another element having a same name (but for use of the ordinal term), to distinguish the claim elements.

The terms "about" and "approximately" shall generally mean an acceptable degree of error for the quantity measured given the nature or precision of the measurements. Typical, exemplary degrees of error are within 10%, and preferably within 5% of a given value or range of values. Alternatively, and particularly in biological systems, the terms "about" and "approximately" may mean values that are within an order of magnitude, preferably within 5-fold and more preferably within 2-fold of a given value. Numerical quantities given herein are approximate unless stated otherwise, meaning that the term "about" or "approximately" can be inferred when not expressly stated.

Unless otherwise defined, all technical terms used herein have the same meaning as commonly understood by one of ordinary skill in the art to which this disclosure belongs. As used herein and in the claims, the singular forms "a," "an," and "the" include the singular and the plural reference unless the context clearly indicates otherwise. Thus, for example, a reference to "an agent" includes a single agent and a plurality of such agents. Any reference to "or" herein is intended to encompass "and/or" unless otherwise stated.

Various exemplary embodiments of compositions and methods according to this disclosure in addition to those shown and described herein will become apparent to those skilled in the art from the foregoing description and the following examples and fall within the scope of the appended claims. Those skilled in the art will recognize, or be able to ascertain using no more than routine experimentation, many equivalents to the specific embodiments of the disclosure described herein. Such equivalents are intended to be encompassed by the following claims.

EXAMPLES

The following examples will enable one of skill in the art to more readily understand the principles thereof. The following examples are presented by way of illustration and are not meant to be limiting in any way.

The inventor previously developed a self-destructing *Salmonella* lysis system in which the bacteria are attenuated, yet capable of synthesizing a selected protein or harboring a DNA vaccine, to serve as vaccine delivery platforms against various infectious diseases. The *Salmonella* lysis system contained two components: a lysis *Salmonella* strain and a lysis vector. The *Salmonella* lysis strains harbor a deletion of asdA and the arabinose-regulated expression of murA, two genes required for the synthesis of the peptidoglycan layer of the bacterial cell wall. They also contain additional mutations intended to enhance bacterial cell lysis and antigen or DNA vaccine delivery. The lysis vector cooperatively works with its host *Salmonella* lysis strain to facilitate the arabinose-dependent bacterial cell wall synthesis needed for bacterial reproduction. Upon invasion of host tissues, which is an arabinose-free environment, synthesis of the bacterial cell wall eventually ceases. This leads to bacterial cell lysis to release cell contents after bacteria accumulate in host tissues and accomplish *Salmonella* self-eradicating. Experiments were undertaken to genetically engineer the lysis strains into a versatile set of tumor navigating anti-cancer material delivering vehicles.

Five to six percent of individuals will develop colorectal cancer (CRC) over their lifetime in the United States. The heavy burden that CRC imposes on our society emphasizes the need to develop effective strategies to prevent and treat this disease. It has been reported that mutations of the adenomatous polyposis coli (APC) gene predispose individuals to familial adenomatous polyposis (FAP), characterized by multiple tumors in the large intestine. Mice carrying a CDX2P-NLS-Cre recombinase transgene and a loxP-targeted Apc allele develop mainly colorectal tumors after tamoxifen induction. A transgenic $Apc^{flox/flox}$/CDX2-CRE colon tumor mouse models greatly mimic human FAP-associated colorectal cancer and sporadic colorectal cancer. Moreover, direct orthotopic cell microinjection, between the mucosa and the muscularis externa layers of the cecal wall of immunocompromised NOD. Cg-Prkdcscid II2rgtm1Wjl/SzJ (NSG™) mice, induces tumor foci in the most relevant metastatic sites observed in humans. The application of this procedure to the human colorectal cancer cell lines HCT-116 yielded high tumor takes and dissemination rates, replicating the metastatic spread to lymph nodes, liver, lung, and peritoneum observed in advanced human colorectal cancer. To faithfully recapitulate human CRC, in addition to allograft and xenograft subcutaneous tumor models, the transgenic and orthotopic colon tumor mouse models were used to evaluate our re-engineered GMS therapeutic strains on inhibition of tumor growth and cancer metastasis.

The *Salmonella* chemotaxis system was engineered to develop tumor navigating, self-eradicating, and TRAIL-armed genetically engineered *Salmonella*. These GMS hold tumor-navigating features and are able to release TRAIL into tumor bed via *Salmonella* cell lysis leading to the induction of tumor cell apoptosis. These GMS were comprehensively evaluated to assure the safety and demonstrate their efficacy on the suppression of cancer growth and metastasis in subcutaneous, orthotopic, and transgenic colon cancer mouse models. These GMS dramatically induced a variety of types of cancer cell death in vitro. Intra-tumor (IT) injected GMS significantly reduced tumor growth in both allograft and xenograft subcutaneous colon cancer mouse models. Moreover, oral administrated (OR), a convenient and less toxic route than parenteral administration, GMS reduced significant tumor growth in the transgenic CRC mouse model and inhibited metastasis in the xenograft orthotopic colon cancer mouse model.

Materials and Methods

Attachment and invasion assay of GMS strain in cancer cells

This assay was performed following the protocol previously described by S. Stender et al., with minor modifications. Briefly, $0.1 \times 10^6$ HCT-116 or CT-26 cells were seeded into a 4-well Nunc® Lab-Tek® Chamber Slide (154526, Thermo Fisher Scientific) for 24 hours in a tissue culture medium containing 10% FBS. GMS strains were grown overnight in LA broth and then diluted 1:20 into a fresh LA medium, grown until $OD_{600}$ nm reached 0.9. To start the assay, bacteria were spun down and re-suspended with 500 μl of tissue culture medium without FBS. HCT-116 or CT-26 cells were incubated with the bacteria suspension at a multiplicity of infection (MOI; the number of bacteria per cell) of 200:1 at 37° C., 5% $CO_2$ for 90 minutes. Then the cells were washed three times with phosphate-buffered saline (PBS) and fixed in PBS containing 3.7% paraformaldehyde. Extracellular bacteria were stained with a mouse monoclonal anti-*Salmonella* antibody (NB110-16952, Novus Biological, 1:200) and a secondary anti-mouse-Alexa Fluor 488 conjugate (A11001, Thermo Fisher Scientific, 1:200). After permeabilization of the cell membrane (3 minutes in PBS, 0.1% Triton X-100), intracellular bacteria were stained with the anti-*Salmonella* antibody (NB110-16952, Novus Biological, 1:200) and a secondary anti-mouse-Alexa Fluor 555 conjugate (A21422, Thermo Fisher Scientific, 1:200). The nuclei of cancer cells were stained with 4,6-diamidino-2-phenylindole (DAPI). Samples were mounted and analyzed using an EVOS™ FL Auto Imaging System (Thermo Fisher Scientific).

Apoptosis Cell Detection by Flow Cytometry Analysis

Cancer cells were harvested after being treated with the control vehicle or desired GMS stains at a MOI of 20:1 for 16 hours. Cell death was detected using the Annexin V-FITC kit (4830-01-K, Trevigen) or FITC Annexin V Apoptosis Detection Kit (640914, Biolegend) following the manufactory protocols. Samples were then analyzed by flow cytometry (Beckman counter). The percentage of dead cells from each sample was analyzed using Kaluza Analysis Software (Beckman counter).

Transwell Chemotaxis Assays $0.5 \times 10^6$/well of HCT-116 or CT-26 cells were cultured in a 6-well plate with a medium containing 10% FBS for 24 hours before the assay, and then the cells were cultured in the 1.5 mL tissue medium without FBS during the assay. GMS strains were grown overnight in LA broth, and then diluted 1:20 into fresh LA medium grown until OD600 nm reached 0.9. Next, 200 µl bacteria solutions from each GMS strain were span down and re-suspended into 200 µl tissue culture media, then added to the top of the insert wells (3 µm pore) (353092, BD Falcon) and covered with an 800 µl soft swimming agar layer (0.25% agar, 1% tryptone). The insert wells with GMS strains were put into the 6-well plates with HCT-116 or CT-26 cells to incubate at 37° C. for 6 hours. 100 µl culture media from the bottom section were 182 sub-cultured on a LA agar plate at 37° C. for 16 hours. Colonies from each plate were counted.

Animal Models

All animal experiments conform to our animal protocols approved by the Institutional Animal Care and Use Committee. We aimed for at least three animals per group (range 3-12 mice) to allow basic statistical inference while using a justifiable number of mutant mice. Mice of similar ages were randomly allocated into different groups.

Subcutaneous CT-26 tumors in BALB/c mice: BALB/c mice were purchased from Charles River Laboratories (Worcester, MA). $1 \times 10^5$ CT-26 cells were injected into the flanks of the BALB/c mice at 6-8 weeks old. For the colonization assay, $1 \times 10^8$ CFU of each GMS strain in 20 µl of PBS was intra-tumor injected when the tumor size reached 0.3 mm³ (3 mice/group). Mice were euthanized at day 9 post-inoculation, and their spleens and tumors were collected aseptically. Tissues were homogenized and plated on LB agar with 0.2% arabinose to evaluate colonization and persistence, and onto LB agar plates without arabinose to confirm arabinose dependency. For the safety and anticancer efficacy assays, mice were treated with $1 \times 10^8$ CFU GMS strain in 20 µl of PBS by intra-tumor injection when the tumor size reached 0.3 mm³.

Subcutaneous HCT-116 tumors in NSG™ mice: NSG™ mice were obtained from Jackson Laboratory. About $1 \times 10^6$ HCT-116 cells were injected into the flanks of NSG™ mice at 6-8 weeks old. These mice were treated with GMS strains (20 µl, $1 \times 10^9$ CFU in PBS) by intra-tumor injection when the tumor size reached 0.3 mm³.

Transgenic $APC^{flox/flox}$ and CDX2-CRE tumor models: $APC^{flox/flox}$ and CDX2-CRE mice (Jackson Laboratory) were crossed to generate C57BL/6J ($Apc^{flox/flox}$/CDX2-CRE) mice. At 8 weeks old, $Apc^{flox/flox}$/CDX2-CRE mice were injected with Tamoxifen (T5648-19, Sigma-Aldrich) (IP, 25 mg/kg body weight) in sunflower seed oil (S1929, Spectrum) to induce polypus formation in the large intestine. These mice were orally treated with GMS strains (30 µl, $1 \times 10^9$ CFU) 10 days post Tamoxifen induction. Mice were euthanized 10 days after inoculation, and the colorectal polypi were analyzed. For survival assay, mice were treated orally with GMS every 10 days for three treatments, beginning 10 days post-Tamoxifen injection.

Liver metastasis in NSG™ orthotopic mouse models: about $5 \times 10^4$ HCT-116 cells were injected into the cecal wall of NSG™ mice at 8 weeks old. Mice were orally treated with GMS strains (30 µl, $1 \times 10^9$ CFU) 7 days after surgery. Mice were euthanized 35 days after inoculation, and the tumor numbers in livers were recorded.

Immunohistochemical Staining

Paraffin-embedded tissue sections (5 µm thick) were stained with an anti-Ki67 rabbit antibody (12202, 1:400, cell signaling technology) or an anti-*Salmonella* rabbit antibody (NB600-1087, 1:200, Novus Biologicals) overnight at 4° C. The immunohistochemical staining was completed by using a VECTASTAIN Elite ABC HRP Kit (PK-6100, Vector laboratory) and a DAB Peroxidase (HRP) Substrate Kit (SK-4100, Vector laboratory) following the manufacturer's protocols. Samples were mounted and analyzed using an EVOS™ 227 FL Auto Imaging System (Thermo Fisher Scientific).

Isolation of Immunocytes from Tumor and Flow Cytometry Analysis

CT-26 cells (approximately $1 \times 10^5$) were implanted in the hind flanks of BALB/c mice. When tumors reached 150 mm³ in volume (day 0), mice were treated with PBS or GMS515(pK5097). Tumor tissues were carefully separated on day seven post-treatment. For transgenic $Apc^{flox/flox}$CDX2-CRE mice, polyps were isolated under the dicing microscope were weighted and minced. Then tumor tissues were minced and digested using digestion buffer (RPMI medium containing 5% FBS, 200 units/ml of collagenase, and 25 U/ml DNase I) (Gibco) for 1 hour at 37° C. under slow rotation. Discontinuous (44% and 67%) percoll (GE) separation method was used to enrich immunocytes. Immunocyte cells isolated from tumor were incubated for 30 min on ice with the appropriate combination of the following antibodies (Biolegend) in staining buffer (PBS with 0.1% BSA) at the following dilution: CD45-PB (1:200), or CD45-FITC (1:200), CD3-PB (1:100), CD8a-PE-Cy7 (1:100), CD107a-FITC (1:50), IFN-γ-FITC (1:50), CD335-PE (1:100). For analysis of IFNγ positive T cells and NK cells, isolated colonic immune cells (approximately $5 \times 10^6$ cells/well) were incubated with CT-26 tumor cells (approximately $1 \times 10^6$ cells/well) in a 6-well plate with brefeldin A, 5 µg/ml (Biolegend) in RPMI supplemented medium with 10% FBS. Cells were incubated at 37° C. for 4 hours, then were washed and stained with cell surface markers. Cells were fixed and permeabilized using a Cytofix/Cytoperm kit (BD biosciences) followed by intracellular cytokine detection with anti-IFNγ-FITC (1:50) in a permeabilization buffer at 4° C. for 30 minutes. After the cells were washed twice with 1 ml of the labeling buffer, they were analyzed on a Gallios flow cytometer (Beckman Coulter).

Bacterial Strains and Plasmids

Bacterial strains, plasmids, and primers used in this study are provided herein. *S. Typhimurium* strains with asdA gene deletions were grown at 37° C. in LB broth or on LB agar supplemented with 50 µg/ml DAP. Transformants containing araC PBAD asdA murA plasmids were selected on LB agar plates containing 0.2% arabinose (LA). LB agar, containing 5% sucrose and no sodium chloride, was used for sacB gene-based counter-selection in allelic exchange experiments. When required, 25 µg/ml chloramphenicol was added to the culture media. For mouse inoculation, *Salmonella* strains were grown with aeration in LA broth to an optical density at 600 nm (OD600) of 0.9 from a non-aerated static overnight culture. *Salmonella* cells were resuspended in PBS at appropriate CFU. The exact CFU of each inoculum were determined by titer tests after inoculation.

General DNA Procedures

DNA manipulations were carried out as described by Sambrook et al. Oligonucleotides were synthesized by Integrated DNA Technologies (IDT). *Escherichia coli* and *Salmonella* were transformed by electroporation. Suicide vector technology was used to generate precise deletion/deletion-insertion mutations. Conjugational transfer of suicide vectors was performed using the suicide vector donor strain χ7213. PCR amplification was used to obtain DNA fragments for cloning and verification of chromosomal deletion mutations. All plasmid constructs and chromosomal deletion mutations were further verified by nucleotide sequencing.

Construction of tumor-navigating strains GMS410 and GMS515

Suicide vectors pK4946 ($\Delta P_{tar}$::$P_{trc\ \Delta lacO}$ tar) and pK4947 ($\Delta P_{tsr}$::$P_{trc\ \Delta lacO}$ tsr) were constructed using primers listed in Table 1. Briefly, DNA cassettes (the upstream DNA flanking sequence- promoter $P_{trc\ \Delta lacO}$—downstream flanking sequence) were inserted into the suicide vector pRE112 (Table 1). Suicide vector pK4948 (for mutation $\Delta$trg) was constructed by inserting the flanking sequence of gene trg into suicide vector pRE112. To test the tumor-navigating feature of mutations $\Delta P_{tar}$::$P_{trc\ \Delta lacO}$ tar, $\Delta P_{tsr}$::$P_{trc\ \Delta lacO}$ tsr, and $\Delta$trg, each single mutation was created in *Salmonella* by conjugating wild-type strain χ3761 with *E. coli* strain χ7213 carrying suicide vector pK4946, pK4947, or pK4948. The resulting strains were named GMS371, GMS372, and GMS525 (Table 1). Then, single mutation $\Delta P_{tar}$::$P_{trc\ \Delta lacO}$ tar or triple mutations $\Delta P_{tar}$::$P_{trc\ \Delta lacO}$ tar, $\Delta P_{tsr}$::$P_{trc\ \Delta lacO}$tsr, and $\Delta$trg, were introduced into strain GMS409 by conjugation to achieve the tumor-navigating strains GMS410 and GMS515, respectively.

The promoter sequence for $P_{trc\ \Delta lacO}$ DNA cassette is set forth in the accompanying sequence listing as SEQ ID NO:1:

```
                                              (SEQ ID NO: 1)
5'-ATTCTGAAATGAGCTGTTGACAATTAATCATCCGGCTCGTATAAT
                    -35                         -10

GTGTAGATGCGTAGGCACCTGTTACGACGAACCACACAGGAAACAGA
     random sequence                      SD

CC-3'
```

Nucleic acid sequences for plasmids pK4946, pK4947, and pK4948 are provided as SEQ ID NO:3, SEQ ID NO:5, and SEQ ID NO:6, respectively.

Construction of TRAIL Expressing Lysis Vector pK5079

The cDNA fragment of human TRAIL gene (GenBank: ABM84955.1) was derived from plasmid pDNR-Dual_with_human_insert (Clone ID: HsCD00001122, DNASU). The amplified TRAIL sequence was inserted into lysis vector pYA3681 to achieve TRAIL expressing lysis vector pK5079 (see FIG. 10). Nucleic acid sequence for plasmid pK5079 is provided as SEQ ID NO:7. Then, pK5079 was transformed into strains GMS409, GMS410, and GMS515. The final tumor-navigating GMS strains evaluated in this study were GMS410(pK5079) and GMS515(pK5079), with GMS409(pK5079) serving as a negative control of chemoreceptor modification. The expression of the TRAIL protein in the isopropyl β-D-1-thiogalactopyranoside (IPTG)-induced GMS cells was verified by SDS/PAGE and western blot analysis.

Construction of Suicide Vectors to Create GMS Strains Preventing *Salmonella*-Induced PD-L1 Overexpression.

Suicide vectors pK4951 ($\Delta$sseL), pK4952 ($\Delta$spvD), and pK4953 ($\Delta$ssrAB) were constructed using primers listed in Table 1. Briefly, DNA cassettes (the upstream DNA flanking sequence- downstream flanking sequence) were inserted into the suicide vector pRE112 (Table 1). Suicide vectors pK4951 (for mutation SseL), pK4952 (for mutation SpvD), and pK4953 (for mutation SsrAB) were constructed by inserting the flanking sequence of genes sseL, spvD, and ssrAB into suicide vector pRE112, respectively. To test the effect of these mutations on *Salmonella*-induced PD-L1 overexpression, $\Delta$sseL, $\Delta$spvD, and $\Delta$ssrAB, each single mutation will be created in *Salmonella* by conjugating wild-type strain χ3761 with *E. coli* strain χ7213 carrying suicide vector pK4951, pK4952, or pK4953. Then, single mutation $\Delta$sseL, $\Delta$spvD, and $\Delta$ssrAB will be introduced into strain GMS515 by conjugation, respectively.

Nucleic acid sequences for plasmids pK4951, pK4952, and pK4953 are provided as SEQ ID NO:41, SEQ ID NO:42, and SEQ ID NO:43, respectively.

Strain Characterization

The GMS strains were compared with vector controls for the stability of plasmid maintenance over 50 generations, arabinose-dependent growth, and protein synthesis. Molecular genetic attributes were confirmed by PCR and sequencing with appropriate primers. Lipopolysaccharide profiles of GMS strains were examined. For detection of constitutive over-expression of chemoreceptors Tar and Tsr in GMS strains, 12 µl and 2 µl of bacterial cultures at an $OD_{600}$ of 0.9 were subjected to an SDS/PAGE and immunoblot analysis, respectively.

Growth Curve of GMS Strains

Cells were grown in LB-broth at 37° C. until reaching the early stationary phase. A 1:100 dilution of a saturated culture in LB was incubated at 185 rpm. The $OD_{600}$ was measured at different time points over 8 hours. The data are presented as the means and SD from three independent experiments.

TABLE 1

Bacterial strains, plasmids, and primers used in this study

| Strain or Plasmid | Description | Source |
|---|---|---|
| *Escherichia coli* | | |
| χ6212 | $\Delta$asd-DH5α derivative | Kang HY, Srinivasan J, Curtiss R, 3rd. Immune responses to recombinant pneumococcal PspA antigen delivered by live attenuated *Salmonella enterica* serovar typhimurium vaccine. Infect Immun 2002; 70:1739-49. |

TABLE 1-continued

Bacterial strains, plasmids, and primers used in this study

| Strain or Plasmid | Description | Source |
| --- | --- | --- |
| χ7213 | F-supE42 λt3rthi-1 thr-1 leuB6 supE44 tonA21 fhuA21 lacY1 recA1 RP4 2-Tc::Mu (λpir) ΔasdA4 Δ(zhf-2::Tn10) | Roland K, Curtiss R, 3rd, Sizemore D. Construction and evaluation of a delta cya delta crp *Salmonella typhimurium* strain expressing avian pathogenic *Escherichia coli* O78 LPS as a vaccine to prevent airsacculitis in chickens. *Avian Dis* 1999; 43:429-41. |
| *Salmonella enterica serovar Typhimurium* | | |
| χ3761 | Wild-type | Kong W, Wanda SY, Zhang X, et al. Regulated programmed lysis of recombinant *Salmonella* in host tissues to release protective antigens and confer biological containment. *Proc Natl Acad Sci USA* 2008; 105:9361-6. |
| GMS371 | $\Delta P_{tar}::P_{trc\ \Delta lacO}$ tar | This study (previously referred to as χ11371) |
| GMS372 | $\Delta P_{tsr}::P_{trc\ \Delta lacO}$ tsr | This study (previously referred to as χ11372) |
| GMS525 | Δtrg | This study (previously referred to as χ11525) |
| GMS526 | tar-Flag-tag in χ3761 | This study (previously referred to as χ3761 tar-tag) |
| GMS527 | tsr-c-Myc-tag in χ3761 | This study (previously referred to as χ3761 tsr-tag) |
| GMS528 | $\Delta P_{tar}::P_{trc\ \Delta lacO}$ tar-Flag-tag in GMS371 | This study (previously referred to as χ11371 tar-tag) |
| GMS529 | $\Delta Ptsr:\ :P_{trc\ \Delta lacO}$ tsr c-Myc-tag in GMS372 | This study (previously referred to as χ11372 tsr-tag) |
| χ11021 | $\Delta P_{murA}$::TT araC $P_{BAD}$ murA ΔasdA::TT araC $P_{BAD}$ c2 ΔaraBAD Δ(gmd-fcl) Δpmi χrelA::TT araC $P_{BAD}$ lacI | Juarez-Rodriguez MD, Yang J, Kader R, et al. Live attenuated *Salmonella* vaccines displaying regulated delayed lysis and delayed antigen synthesis to confer protection against *Mycobacterium tuberculosis*. *Infect Immun* 2012; 80:815-31. |
| GMS409 | $\Delta P_{murA}$::TT araC $P_{BAD}$ murA Δasd::TT araC $P_{BAD}$ c2 Δ(araC $P_{BAD}$)::P22 $P_R$ araBAD Δ(wza-wcaM) Δpmi ΔrelA::araC $P_{BAD}$ lacI TT ΔpagP::$P_{lpp}$ lpxE ΔendA | This study (previously referred to as χ11409) |
| GMS410 | $\Delta P_{murA}$::TT araC $P_{BAD}$ murA Δasd::TT araC $P_{BAD}$ c2 Δ(araC $P_{BAD}$)::P22 $P_R$ araBAD Δ(wza-wcaM) Δpmi ΔrelA::araC $P_{BAD}$ lacI TT ΔpagP::$P_{lpp}$ lpxE ΔendA $\Delta P_{tar}::P_{trc\ \Delta lacO}$ tar | This study (previously referred to as χ11410) |

TABLE 1-continued

Bacterial strains, plasmids, and primers used in this study

| Strain or Plasmid | Description | Source |
|---|---|---|
| GMS515 | $\Delta P_{murA}$::TT araC $P_{BAD}$ murA $\Delta$asd::TT araC $P_{BAD}$ c2 $\Delta$(araC $P_{BAD}$)::P22 $P_R$ araBAD $\Delta$(wza-wcaM) $\Delta$pmi $\Delta$relA::araC $P_{BAD}$ lacI TT $\Delta$pagP::$P_{lpp}$ lpxE $\Delta$endA $\Delta P_{tar}$::$P_{trc\ \Delta lacO}$ tar $\Delta$Ptsr::$P_{trc\ \Delta lacO}$ tsr $\Delta$trg | This study (previously referred to as χ11515) |
| *S. Typhimurium* GMS strains | | |
| GMS409 (pK5079) | GMS409 carrying TRAIL-expressing plasmid pK5079 | This study |
| GMS410 (pK5079) | GMS410 carrying TRAIL-expressing plasmid pK5079 | This study |
| GMS515 (pK5079) | GMS515 carrying TRAIL-expressing plasmid pK5079 | This study |
| Plasmids Asd⁺/MurA⁺ expression lysis vectors | | |
| pYA3681 | Asd⁺/MurA⁺ expression lysis vector containing pBR ori araC $P_{BAD}$ SD-GTG asdA SD-GTG murA P22$P_R$ anti-sense mRNA prokaryotic expression cassette | Kong W, Wanda SY, Zhang X, et al. Regulated programmed lysis of recombinant *Salmonella* in host tissues to release protective antigens and confer biological containment. *Proc Natl Acad Sci USA* 2008; 105:9361-6. |
| pK5079 | Asd⁺/MurA⁺ expression lysis vector containing pBR ori araC $P_{BAD}$ SD-GTG asdA SD-GTG murA P22$P_R$ anti-sense mRNA prokaryotic expression cassette of human TRAIL | This study (previously referred to as pYA5079) |
| Suicide vectors | | |
| pK4946 | To create genome mutation $\Delta P_{tar}$::$P_{trc\ \Delta lacO}$ tar | This study (previously referred to as pYA4946) |
| pK4947 | To create genome mutation $\Delta$Ptsr::$P_{trc\ \Delta lacO}$ tsr | This study (previously referred to as pYA4947) |
| pK4948 | To create genome mutation $\Delta$trg | This study (previously referred to as pYADtrg or PYA5077) |
| pK4949 | To create genome Tar-Flag-tag | This study |
| PK4950 | To create genome Tsr-c-Myc-tag | This study |
| pK4951 | To create genome mutation $\Delta$sseL | This study |
| pK4952 | To create genome mutation $\Delta$spvD | This study |
| pK4953 | To create genome mutation $\Delta$ssrAB | This study |

TABLE 1-continued

Bacterial strains, plasmids, and primers used in this study

| Strain or Plasmid | Description | Source |
|---|---|---|

Primers

| Name | Sequence |
|---|---|

A. Construction of plasmid pK5079

| | |
|---|---|
| C-Nco I TRAIL 3681 5' | 5'GACGTCCCATGGCTATGATGGAGGTCCAGGGG (SEQ ID NO: 8) |
| C-Xma I TRAIL 3681 3' | 5'CTGCAGCCCGGGCTAGCCAACTAAAAAGGCCCC (SEQ ID NO: 9) |

B. Construction of suicide vectors pK4946

| | |
|---|---|
| tar/cheM Primer 1 | 5'CATCGCCAATACACCGGCCTTTATAAA (SEQ ID NO: 10) |
| tar/cheM Primer 2 | 5'CTACACATTATACGAGCCGGATGATTAATTGTCAACAG CTCATTTCAGAATCGCGGGCGATGAAGAGGCACTCTC (SEQ ID NO: 11) |
| tar/cheM Primer 3 | 5'GGCTCGTATAATGTGTAGATGCGTAGGCACCTGTTACG ACGAACCACACAGGAAACAGACCATGTTTAACCGTATCC GCGTTGTCAC (SEQ ID NO: 12) |
| tar/cheM Primer 4 | 5'GAAGTAGGCATCCATATTGCCATTGTC (SEQ ID NO: 13) |

PK4947

| | |
|---|---|
| tsr Primer 1 | 5'GTCGTTATTGATAACCGCCGGCGTCGC (SEQ ID NO: 14) |
| tsr Primer 2 | 5'CTACACATTATACGAGCCGGATGATTAATTGTCAACAG CTCATTTCAGAATATCACATAAAATAGCCCACGCCCTCC (SEQ ID NO: 15) |
| tsr Primer 3 | 5'GGCTCGTATAATGTGTAGATGCGTAGGCACCTGTTACG ACGAACCACACAGGAAACAGACCATGTTAAAGCGAATTAA AATTGTTACC (SEQ ID NO: 16) | pK4952

| | |
|---|---|
| spvD Primer 1 | 5'-CCCAAGCTTCTCAGGGCAAATTTGCCGGTGACA (SEQ ID NO: 33) |
| spvD Primer 2 | 5'-TAAAATGAATATTTAAAAAAGTTAAGTTACACTACCTCA ATAAAATGC (SEQ ID NO: 34) |
| spvD Primer 3 | 5'-GCATTTTATTGAGGTAGTGTAACTTAACTTTTTTAAATAT TCATTTTA (SEQ ID NO: 35) |
| spvD Primer 4 | 5'-CCCAAGCTTGCTGTACACAAAACGGACTGCACC (SEQ ID NO: 36) | pK4953

| | |
|---|---|
| ssrAB Primer 1 | 5'-CGGGAATTCGCTACTACTTGTGGTATAATAACC (SEQ ID NO: 37) |
| ssrAB Primer 2 | 5'-CTTAATACCATCGGACGCCCCTGGAATGCTTCCC TCCAGTTGCCTGTT SEQ ID NO: 38) |
| ssrAB Primer 3 | 5'-AACAGGCAACTGGAGGGAAGCATTCCAGGGGCGTC CGATGGTATTAAG (SEQ ID NO:39) |
| ssrAB Primer 4 | 5'-CGGGAATTCTGATCCGAGAGATTCCATCCGCTA (SEQ ID NO: 40) |

Results

Reprogramming *Salmonella* Chemotaxis System for Tumor-Navigating

We have improved our self-eradicating *Salmonella* strains to better serve the delivery purpose. Lysis strain GMS409 was engineered to not only harbor the genetic attributes for self-eradicating feature, but also to display genetic characteristics for regulated delayed attenuation, delayed antigen synthesis, and reduced endotoxic activity. However, such GMS strain could not target either cancer cells or tumors. To transform a vaccine delivery strain GMS409 into a universal tumor-navigating delivery vehicle for cancer therapy, our approach was to reprogram the *Salmonella* chemotaxis system to enhance its chemotaxis toward particular tumor secreting amino acids. Such strategy will allow maximized GMS tumor-eradicating and release of an anti-cancer agent inside of the tumor during the self-eradicating process to trigger bacteria-based oncolysis.

Figure 8A:
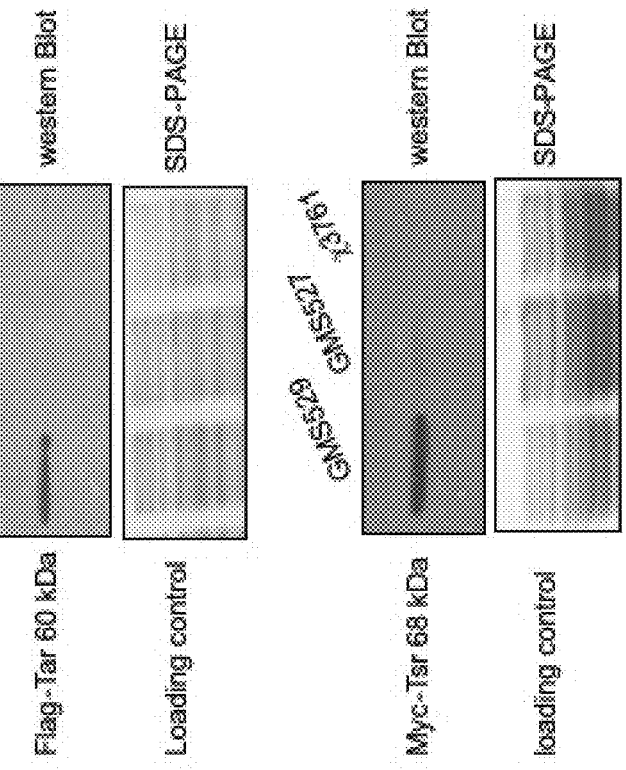
FIGS. 8a-8d illustrate genetic engineering and characterization of GMS strains to enhance beneficial chemotaxis. a. Schematic illustration of experimental design to tag chromosomal chemoreceptor genes and quantify chemoreceptor synthesis. b. Western blot assay (using antibodies against Flag-tag and c-Myc-tag) on the constitutive over-expression of Tar or Tsr chemoreceptor in strains GMS371 and GMS372, compared to their wild-type parent strain χ3'761. c. Schematic illustration of experimental design to delete ribose/galactose chemoreceptor trg gene. d. Chemotaxis assay of strains GMS524 and χ3761 with galactose as a chemoattractant. The representative images (left) of χ3761 (top) and GMS524 (bottom) were captured after 12 hours of incubation. Histogram of swim ring size (right) represents three independent experiments, each in triplicate. Error bars represent SD (n=3, ρ=0.0008).
Figure 8B:
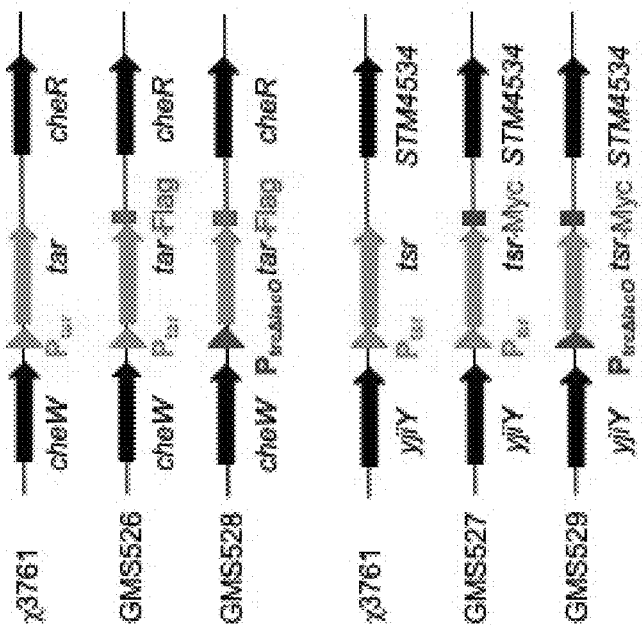
Figures 8C, 8D:
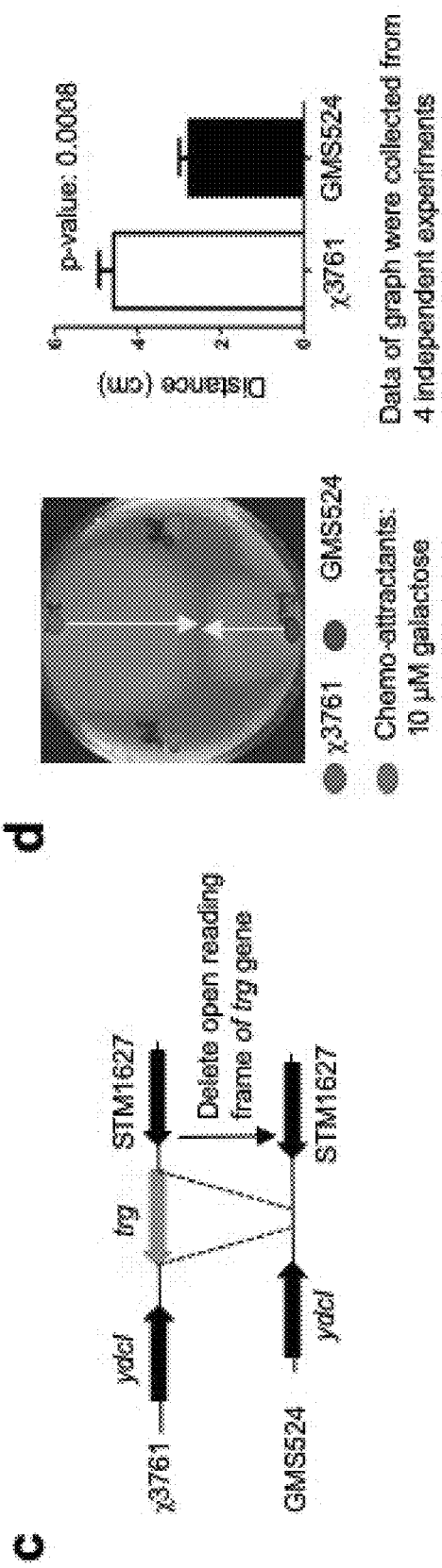

In order to achieve this goal, we first replaced the promoters of the genes encoding chemoreceptors Tar (tar) and Tsr (tsr), respectively, with the Ptrc promoter for constitutive chemoreceptor synthesis. *Salmonella* strains GMS371 carrying single deletion-insertion mutation $\Delta P_{tar}::P_{trc\ \Delta lacO}$ tar and GMS372 harboring single deletion-insertion mutation $\Delta P_{tsr}::P_{trc\ \Delta lacO}$ tsr were created using *Salmonella* wild-type strain χ3761 (Table 1). The constitutive overexpression of chemoreceptors Tar and Tsr in GMS371 and GMS372, respectively, was confirmed by SDS electrophoresis and western blot assay. In addition, strains GMS371 and GMS372 showed similar growth and swimming speed comparing to their wild-type *Salmonella* parent strain χ3761. Chemotaxis assay was performed to demonstrate the ideal enhancement of chemotaxis caused by each deletion-insertion mutation. We found that GMS371 and GMS372 are significantly more attracted to aspartate and serine, respectively, than the wild-type strain χ3761. To further enhance the *Salmonella* accumulation in the layer of tumor quiescent cells, other than the necrotic core, the ribose/galactose receptor trg gene was deleted (FIG. 8C). The strain with Δtrg deletion is much less attracted to galactose than wild-type strain as desired (FIG. 8D). To finally create tumor-navigating, self-eradicating GMS strains, which hopefully will be able to efficiently navigate tumor and release cancer-killing material in the tumor bed, the single mutation $\Delta P_{tar}::P_{trc\ \Delta lacO}$ tar or triple mutations $\Delta P_{tar}::P_{trc\ \Delta lacO}$ tar, $\Delta P_{tsr}::P_{trc\ \Delta lacO}$ tsr, and Δtrg were introduced into GMS409 to achieve strains GMS410 and GMS515 (Table 1).

Building Up Tumor-Targeting Self-Eradicating TRAIL Delivery Vehicles

Figure 9C:
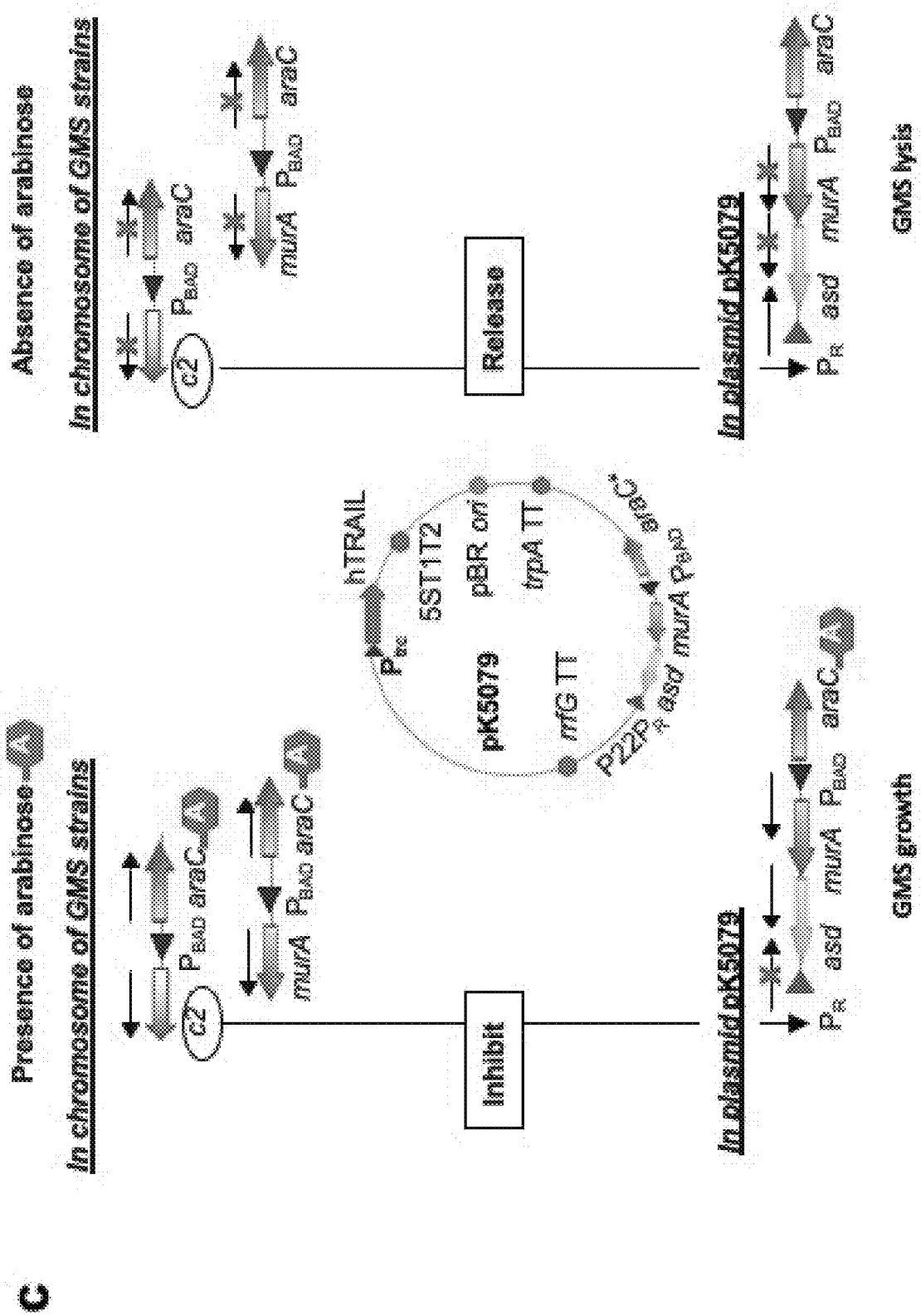

A human TRAIL-expressing lysis vector pK5079 was constructed by inserting the TRAIL coding sequence into lysis vector pYA3681 to assemble a self-eradicating *Salmonella* lysis system for cancer therapy. The repressor LacI, expressed from the built-in chromosomal lacI gene under arabinose-regulated araC $P_{BAD}$ promoter, will turn off TRAIL synthesis in vitro to avoid the reduced growth rates and a compromised ability to colonization caused by high-level production of foreign protein. The diagram of the model illustrating the regulatory of TRAIL synthesis in the GMS strain is shown in FIG. 9a. Then the tumor-navigating strains GMS410 and GMS515 were armed with TRAIL by carrying plasmid pK5079 for enhanced cancer cell-killing. The strain GMS409(pK5079) was built, without tumor-navigating feature, to serve as a negative control. The expression of TRAIL by pK5079 in GMS strains was confirmed through western blotting analysis.

Figure 2A:
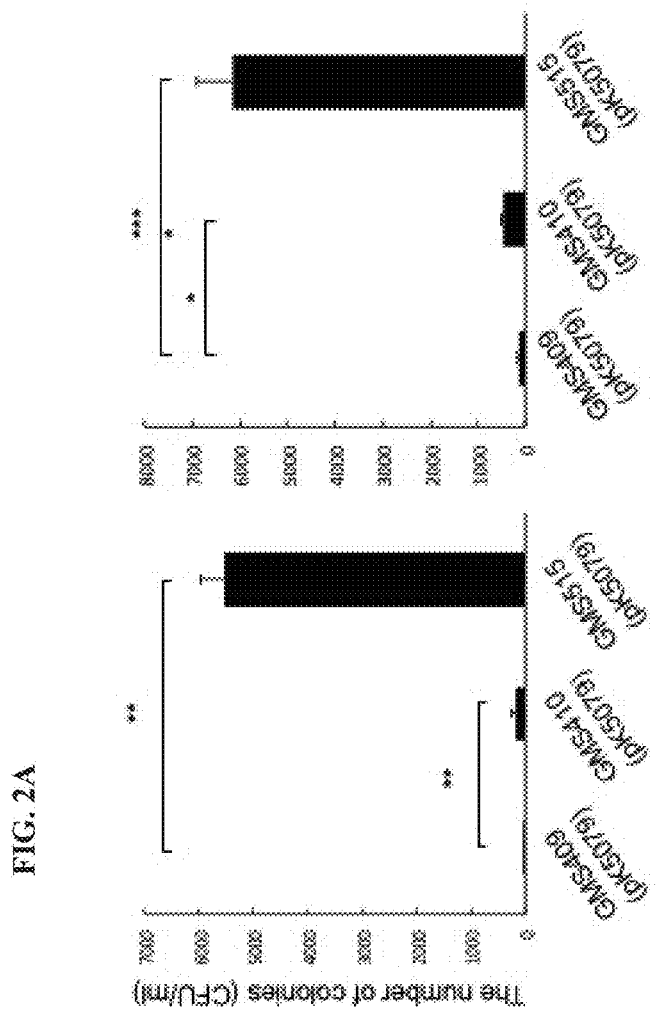
Figure 2A:
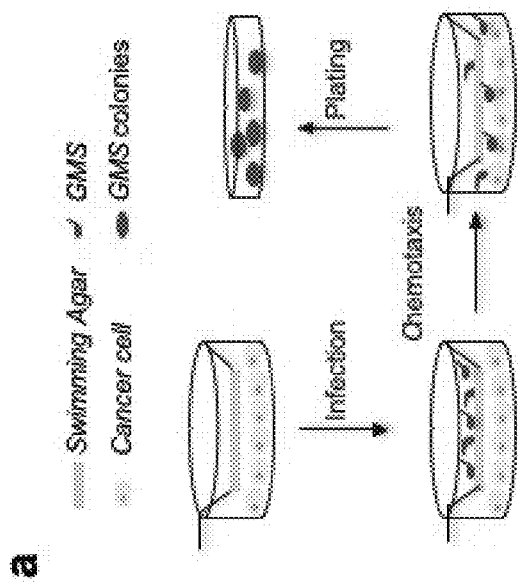

Reprogrammed Chemotaxis System Endues GMS Strains Superior Ability of Cancer Cell Seeking, Attaching and Invading To validate whether the GMS with chemoreceptor modifications could obtain cancer cell-navigating feature, a transwell culture system was used. A swimming agar layer was used as a barrier between GMS strains and colon cancer cells GMS strains were cultured in the upper compartment of the transwell culture system, while mouse colon cancer CT-26 or human colon cancer HCT-116 cells were grown in the lower compartment. The swimming agar layer and micropores in the insert membrane allow GMS strains to cross freely (FIG. 2A, left panel). It was observed that significantly higher numbers of GMS410(pK5079) and GMS515 (pK5079) swam across the swimming agar layer toward CT-26 or HCT-116 cells, whereas very little numbers of GMS409(pK5079) did, indicating that reprogrammed chemotaxis system in GMS410(pK5079) and GMS515 (pK5079) endue them the cancer cell-navigating ability to seek cancer cells (FIG. 2A, right panel). The capability of GMS strains attaching to and invading cancer cells were also examined. The GMS strains were incubated with CT-26 and HCT-116 cells, respectively. We found that more GMS410 (pK5079) and GMS515(pK5079) attached to and invaded into CT-26 cells (FIG. 2B) or HCT-116 cells (FIG. 2C) comparing to the control strain GMS409(pK5079). These data suggest that chemotaxis system reprogramming in GMS410(pK5079) and GMS515(pK5079) strains enable them to be better attracted to cancer cells leading to efficient attachment and invasion compared with their parent strain GMS409(pK5079) without genetically engineered chemotaxis system. Overall, the GMS strains with reprogrammed chemotaxis system possess superior ability to navigate, attach, and invade colon cancer cells.

Reprogrammed GMS Strains Efficiently Induced Colon Cancer Cell Death In Vitro

Figure 3A:
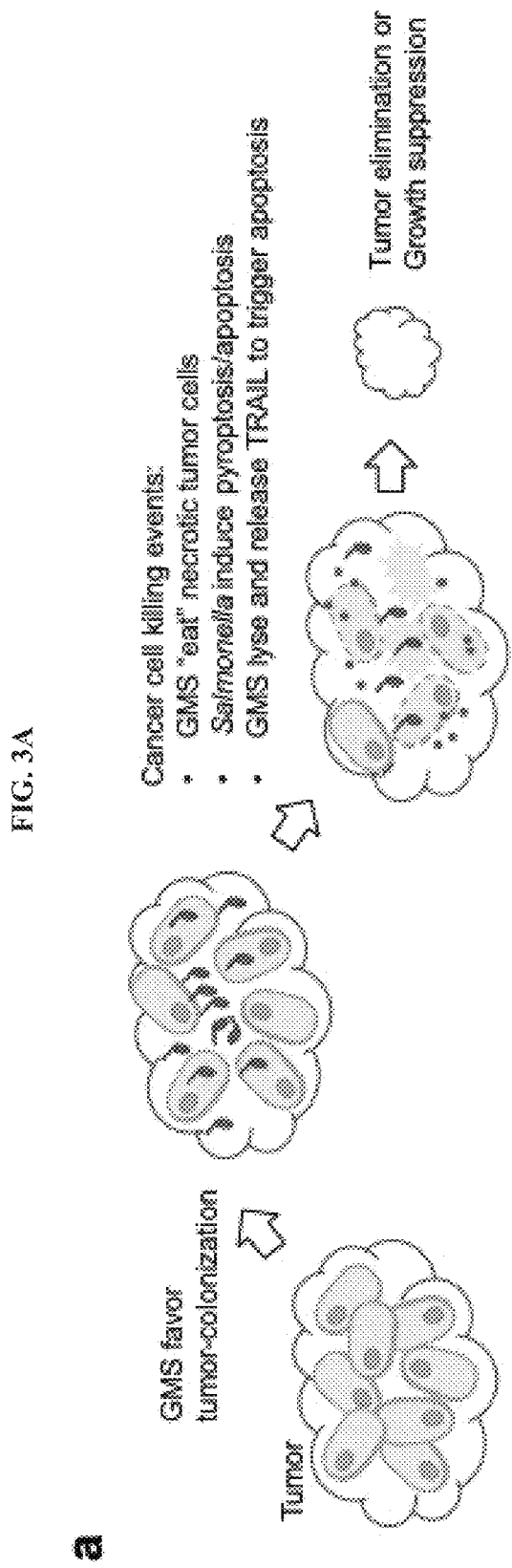
FIGS. 3a-3f demonstrate that reprogrammed GMS strains efficiently triggered caspase-3 activation and colon cancer cell death in vitro. a. Schematic model of apoptosis assays to detect cancer cell killing. b. Representative image of western blotting (left) and quantification (right) to determine the active caspase 3 levels of CT-26 and HCT-116 treated with different GMS strains. Actin was used as a loading control. Normalized active caspase-3 levels were expressed as means, and the error bar represents SD from three different replicates (*p<0.05). c. Representative patterns of Annexin V/PI apoptosis assays following CT-26 cells treated with GMS for 16 hours. d. Percentage of apoptotic cells after treatment. Annexin V-FITC positive CT-26 cells were expressed as means, and the error bar represents SD from three different replicates (*p<0.001). e. Representative patterns of apoptosis assays following HCT-116 cells treated with GMS for 16 hours. f. Percentage of apoptotic cells after treatment. Annexin V-FITC positive HCT-116 cells were expressed as means, and the error bar represents SD from three different replicates (**p<0.0001).
Figure 3B:
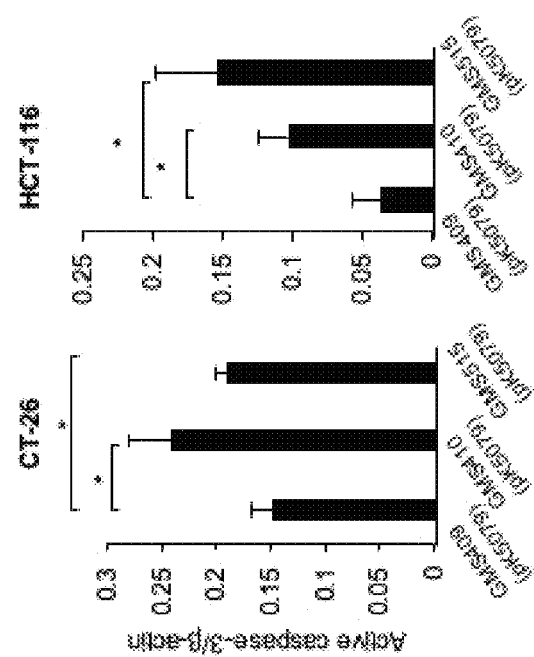
Figure 3B:
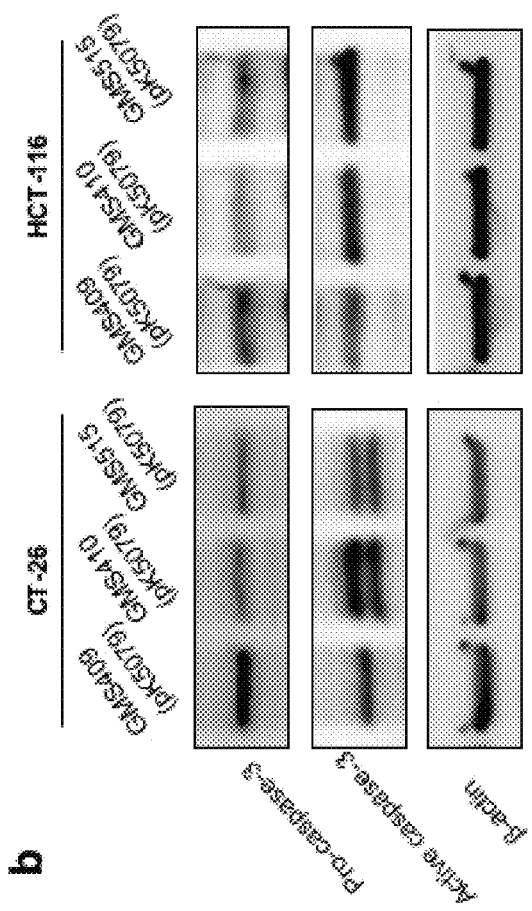
Figures 3C, 3D:
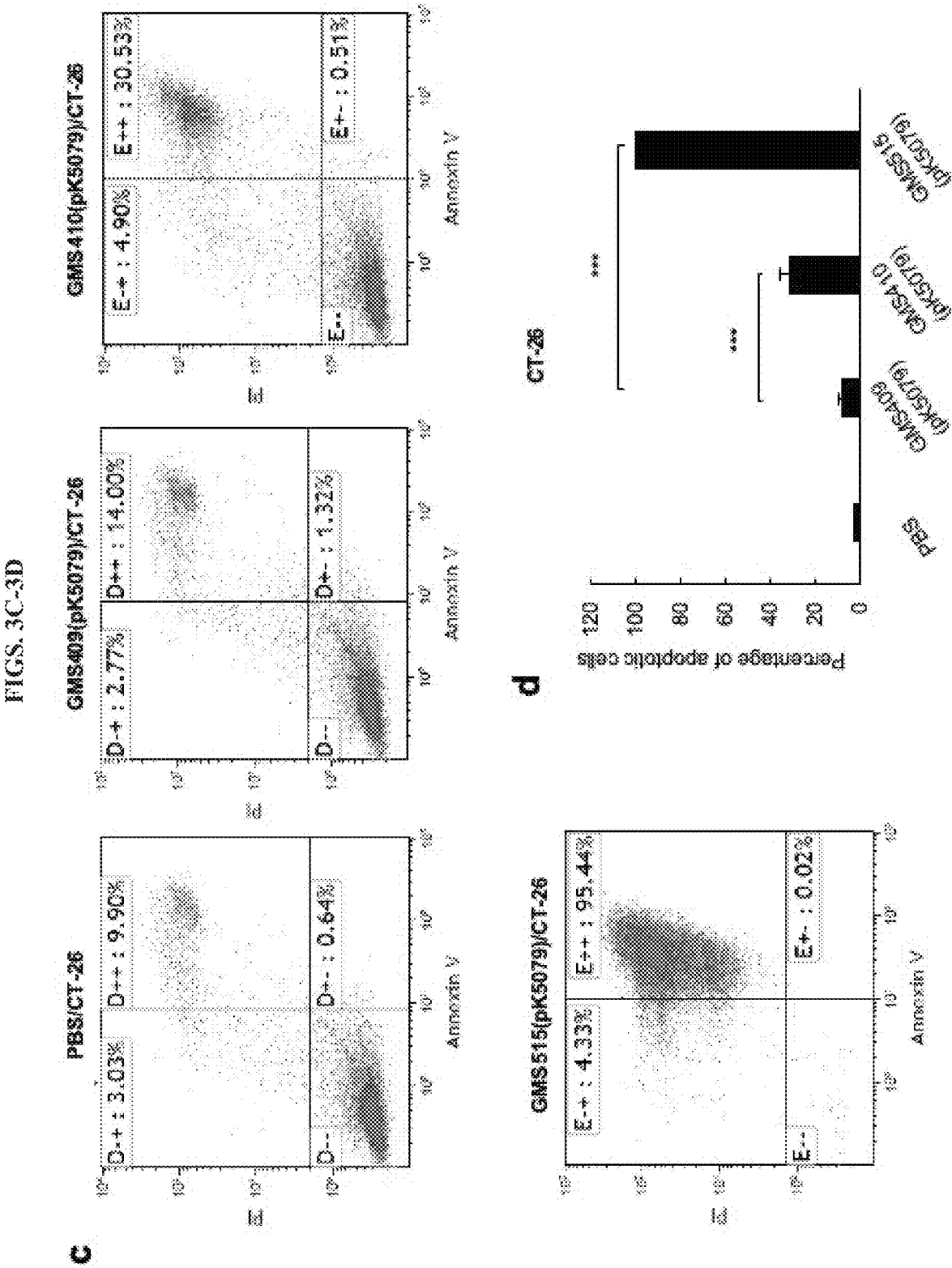
Figures 3E, 3F:
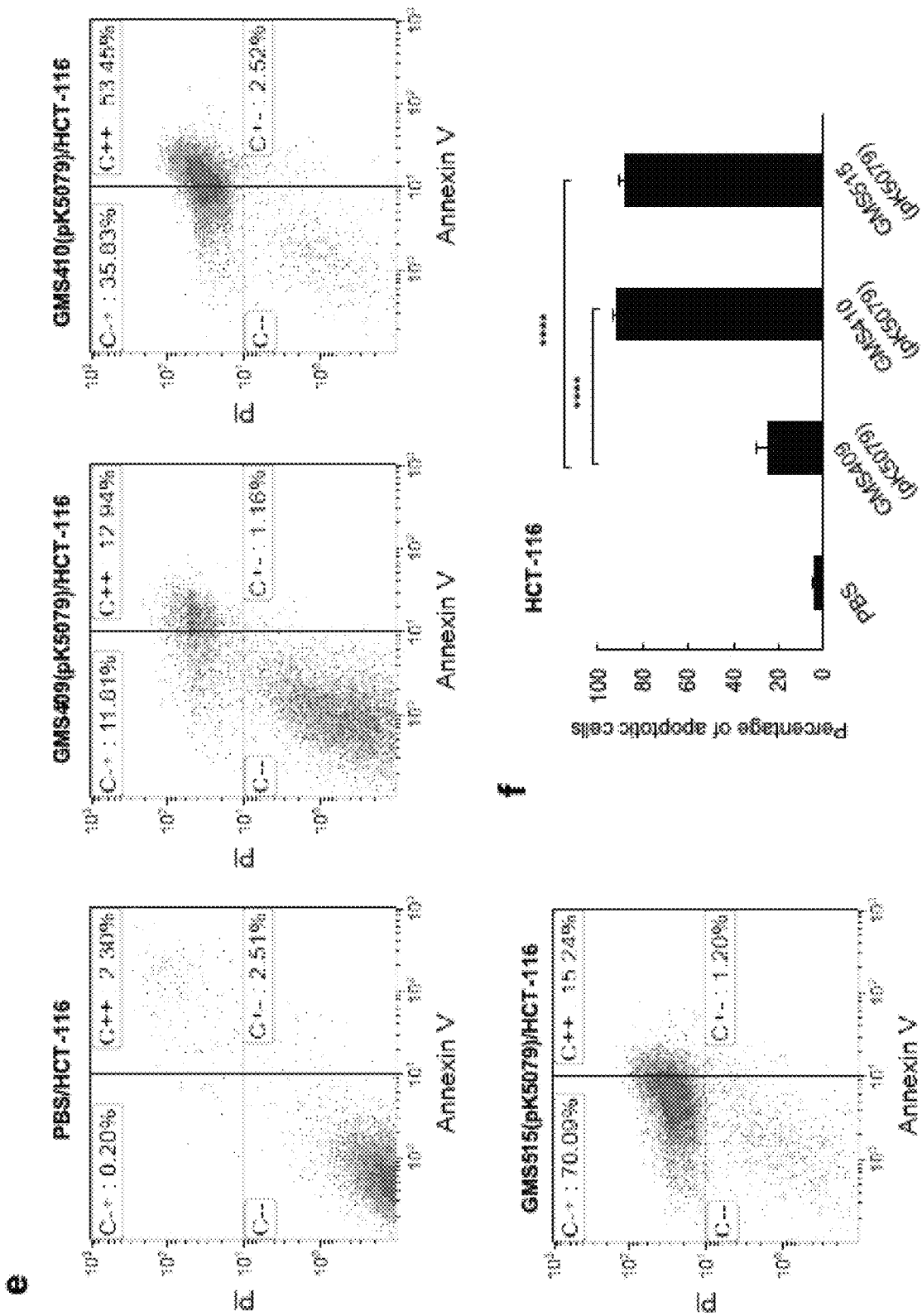

To examine whether the reprogrammed GMS strains have the potential for cancer treatment, the multiple cytotoxic features against cancer cells built into the reprogrammed GMS strains were evaluated in vitro. We first validated the level of activated caspase-3, which is the key "executioner" caspase in the apoptotic cascade, after incubating CT-26 and HCT-116 cells with GMS strains, respectively. It was observed that both cancer cells co-incubated with GMS410 (pK5079) or GMS515(pK5079) had higher levels of active caspase-3 protein and lower levels of pro-caspase-3, comparing to the cells co-incubated with GMS409(pK5079). Our results indicate that the self-eradicating TRAIL delivering GMS strains, with reprogrammed chemotaxis system, are able to promote the apoptotic cascade through caspase-3 activation (FIG. 3B). To further validate the cancer cell-killing features in reprogrammed GMS strains, the apoptosis assays were performed using same colon cancer cell lines. After co-incubating CT-26 cells with GMS515(pK5079) and GMS410(pK5079), it was found that over 99% and 35% of cells were undergoing apoptosis, respectively, which is significantly higher than the sample co-incubated with the control strain GMS409(pK5079) (FIGS. 3C-3D). Furthermore, a significantly higher percentage of cell death was observed in the HCT-116 samples co-incubated with GMS515(pK5079) and GMS410(pK5079) than the control strain GMS409(pK5079) (FIGS. 3E-3F). Collectively, the data suggest that the self-eradicating TRAIL-delivering GMS strains with reprogrammed chemotaxis systems hold remarkable cancer cell-killing ability.

Reprogrammed GMS Suppress Tumor Growth In Vivo

Figure 4A:
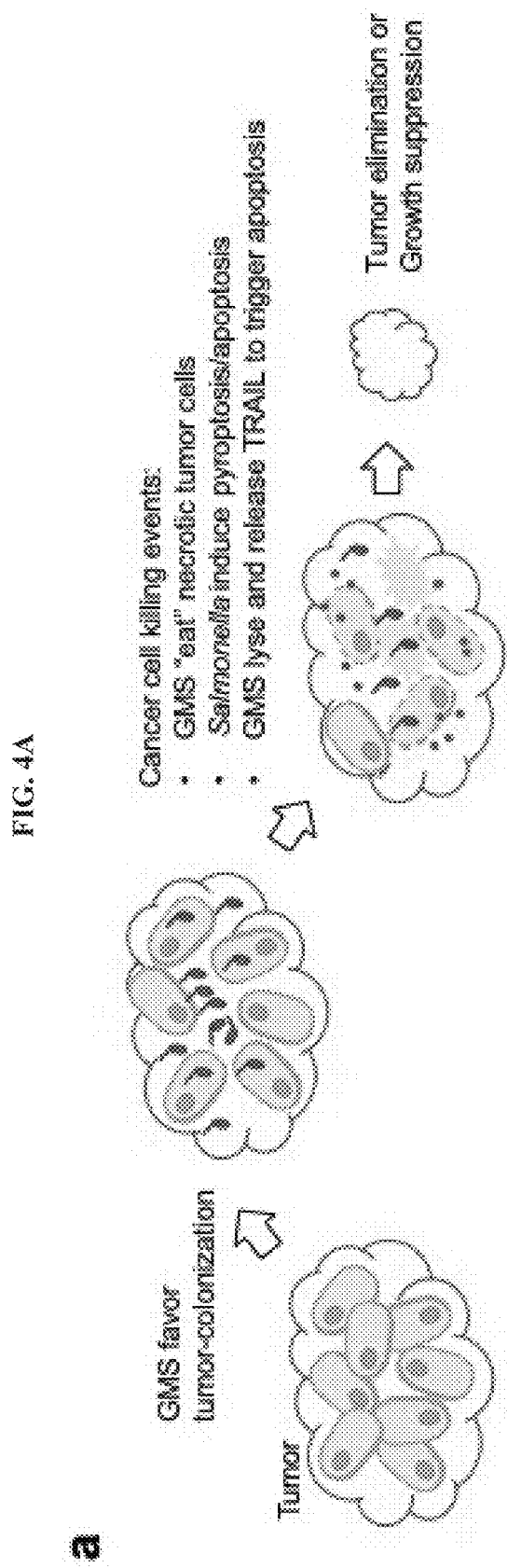
Figure 4B:
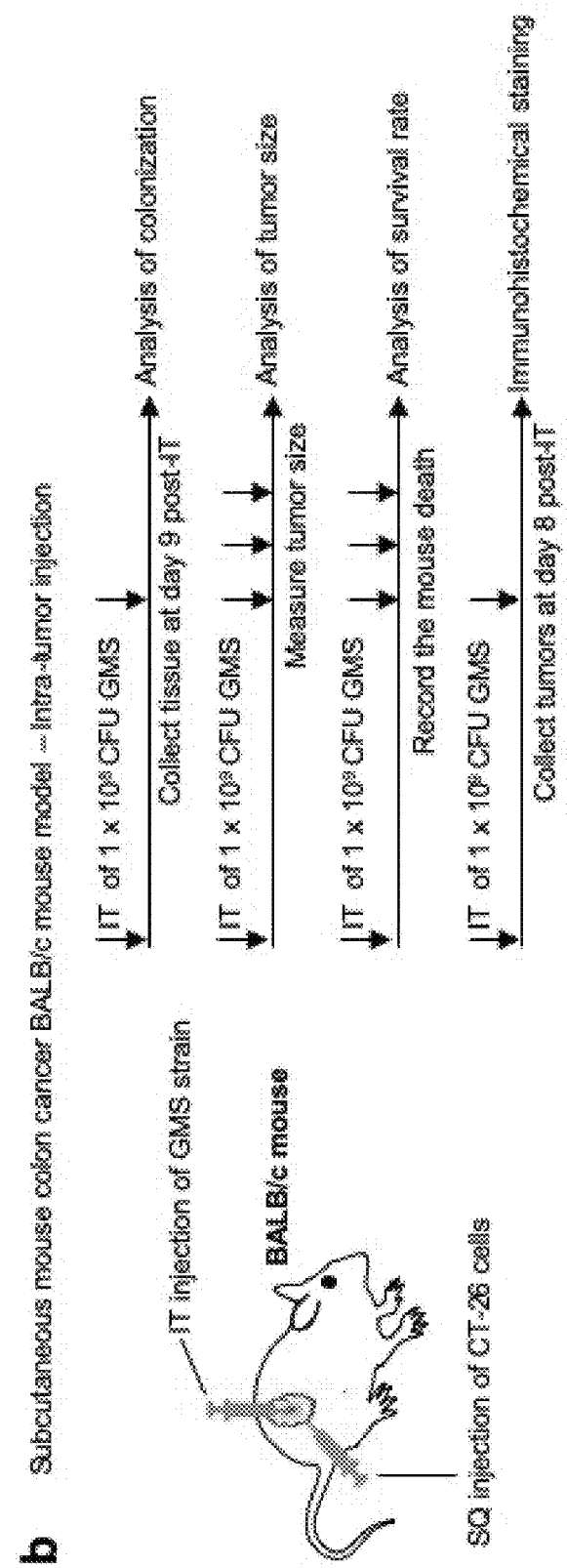
Figure 4C:
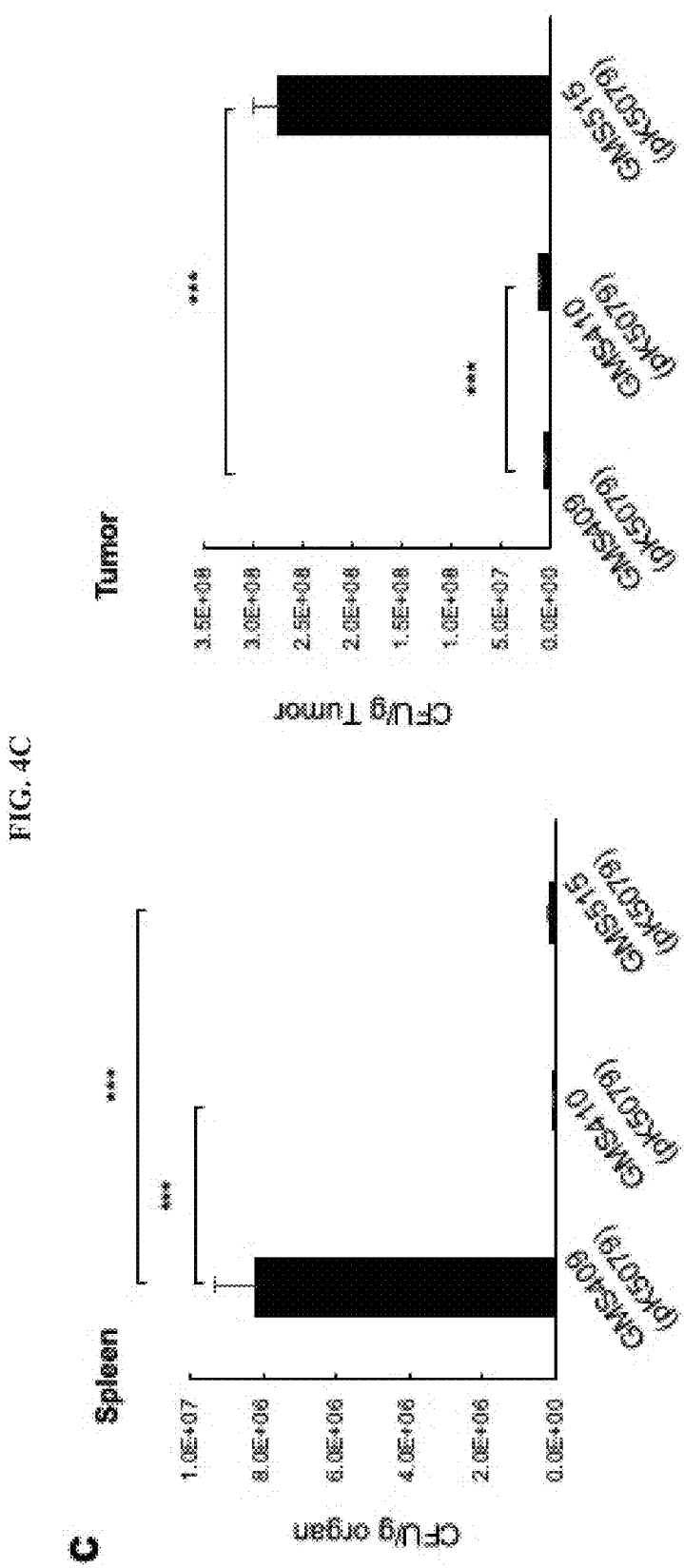
Figure 4D:
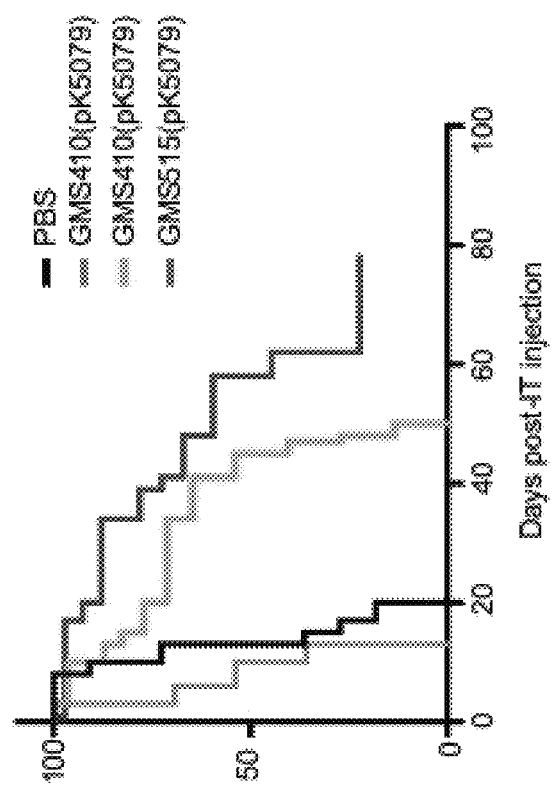
Figure 4E:
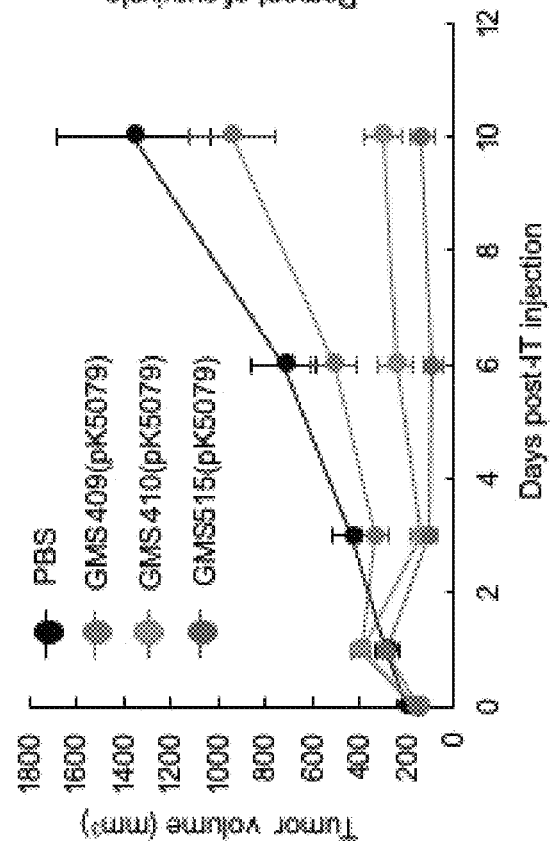
Figure 4F:
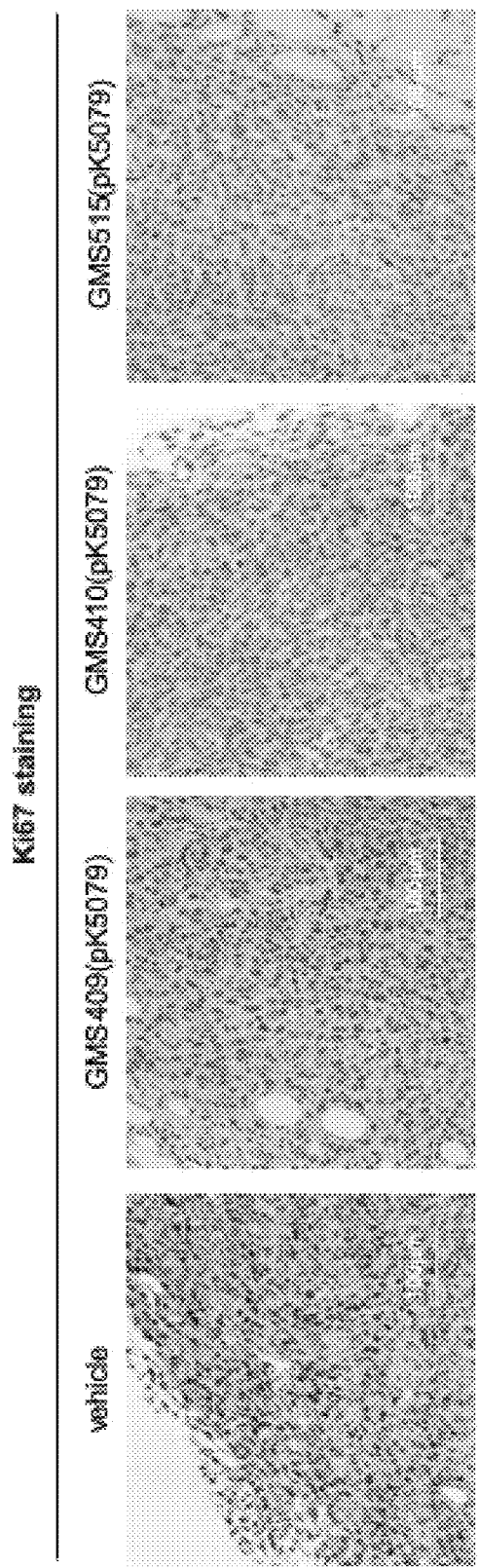
Figure 4H:
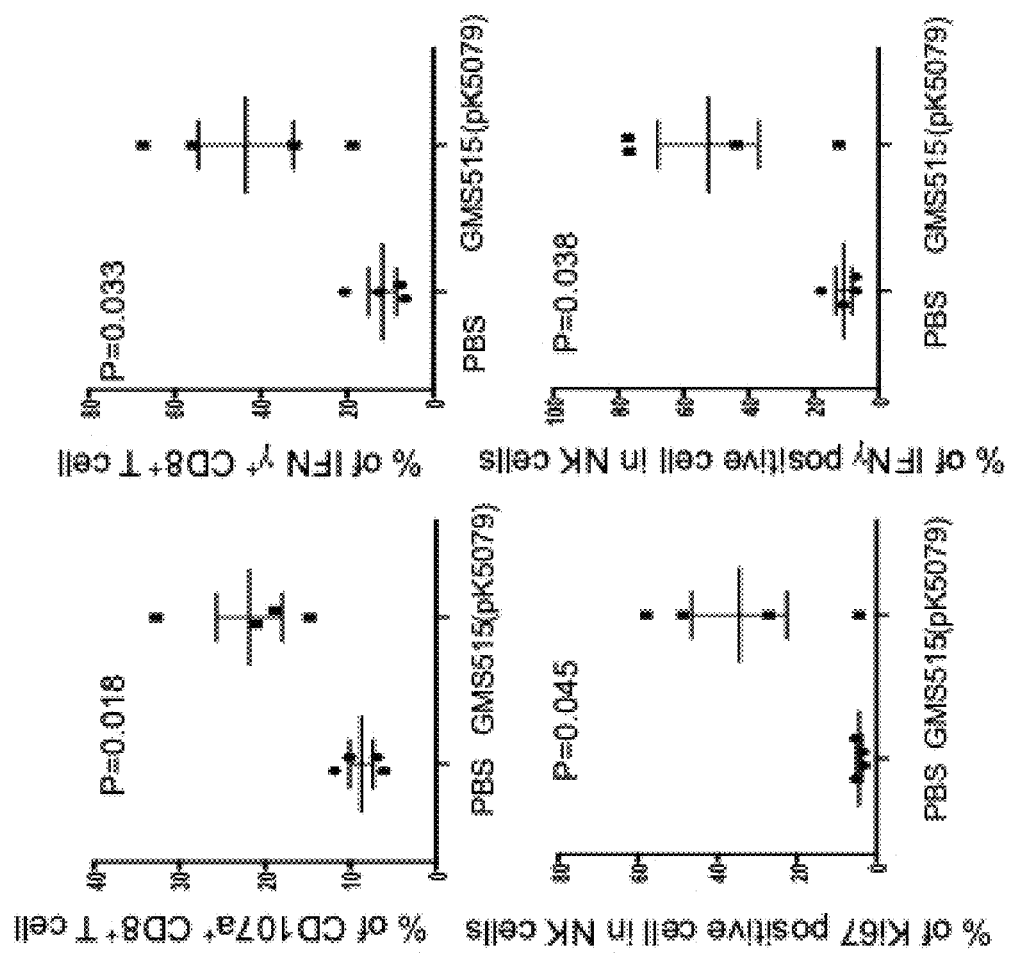

The engineered TRAIL-delivering GMS strains with reprogrammed chemotaxis system, displaying multiple cancer-killing features, have the potential to function as cancer therapeutics (FIG. 4A). Therefore, the impact of reprogrammed GMS-based therapy on tumor growth, following intra-tumor injection, was evaluated in an allograft colon cancer mouse model (FIG. 4B). The CT-26 cells were subcutaneously (SQ) injected into the flank area of BALB/c mice. First, the colonization of GMS strains in tumor versus spleen was determined nine days post-intratumoral injection (IT) of $10^8$ CFU bacteria. We found that the reprogrammed GMS410(pK5079) and GMS515(pK5079) strains preferably accumulated in the tumors, after injection of bacteria into the tumors on the mice, growing the bacterial density up to 5,000 -13,000 times higher comparing to the density of bacteria found in the spleen (FIG. 4C). In contrast, strain GMS409(pK5079) without chemoreceptor modification selectively accumulated in Salmonella preferred colonization organ, spleen. These data suggested that reprogrammed chemotaxis system in GMS410(pK5079) and GMS515 (pK5079) increased their capacity of tumor specific accumulation that is a key safety feature required for efficient Salmonella-based cancer therapy. We then tested whether the GMS strains specifically accumulated in tumor would suppress tumor growth. Phosphate-buffered saline (PBS), GMS409(pK5079), GMS410(pK5079), and GMS515 (pK5079) were administrated by IT injection. The tumor sizes were measured every three days post-IT injection of bacteria. As shown in FIG. 4D, the tumor size of mice treated with GMS410(pK5079) or GMS515(pK5079) was significantly smaller than that treated with PBS or control strain GMS409(pK5079) after three days following IT injection. Moreover, both GMS410(pK5079) and GMS515 (pK5079) treatments prolonged the lifespan of tumor-bearing mice (FIG. 4E). The lifespan of tumor-bearing mice was significantly prolonged, which was correlated with suppression of tumor growth, was ascribed to tumor-navigating GMS-mediated oncolysis. To test the hypothesis, immunochemistry staining of Ki67 (an indicator of cancer cell proliferation) and TUNEL (terminal deoxynucleotidyl transferase dUTP nick end-labeling to detect DNA fragmentation as a hallmark of apoptosis) assays were carried out. It was found that much more Ki67 positive cancer cells were present in the PBS and GMS409(pK5079)-treated tumor samples comparing to the tumor samples from the groups treated with GMS410(pK5079) or GMS515(pK5079) (FIG. 4F). Meanwhile, more apoptotic cells were observed in the tumor sections treated with GMS410(pK5079) or GMS515 (pK5079) than in the PBS- or control strain-treated tumors (FIG. 4G). Recent studies have highlighted the importance of Salmonella-induced systemic anti-tumor immunity. Systemic administration of Salmonella triggers immune cell infiltration and induction of proinflammatory cytokine expressions. The enhanced expressions of IFN-inducible chemokines may play a crucial role in the recruitment of activated $CD8^+$ T cells and an increase in intra-tumoral activated NK cells. Therefore, flow cytometry analysis was performed for lymphocytes isolated from treated tumors of mice injected with GMS515(pK5079), compared to phosphate buffered saline (PBS) control. It showed significantly increased frequencies of activated $CD107a^+CD8^+$ T cells (FIG. 4H, upper-left panel) as well as a trend towards an increased rate of $IFN\gamma^+CD8^+$ T cells (FIG. 4H, upper-right panel). Additionally, we observed a significantly higher percentage of proliferating Ki67 positive NK cells (FIG. 4H, lower-left panel) and $IFN\gamma^+$ positive NK cells (FIG. 4H, lower-right panel). Overall, these results indicate that GMS515(pK5079) could safely promote local tumor regression while also induced systemic tumor-specific antitumor immunity. The tumor-specific T cells will likely mediate the prevention of metastasis (FIG. 4H).

Figure 5A:
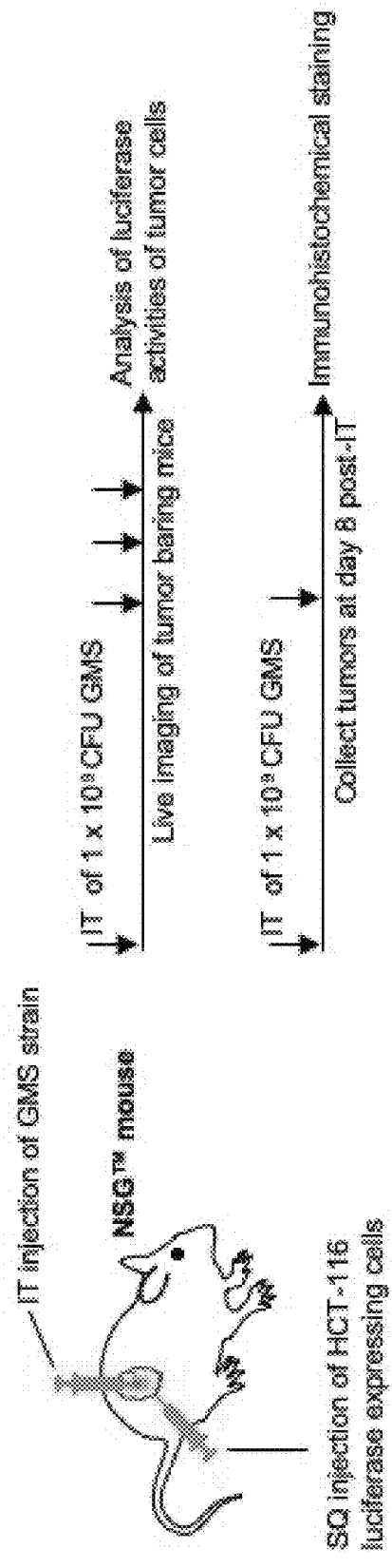
Figure 5B:
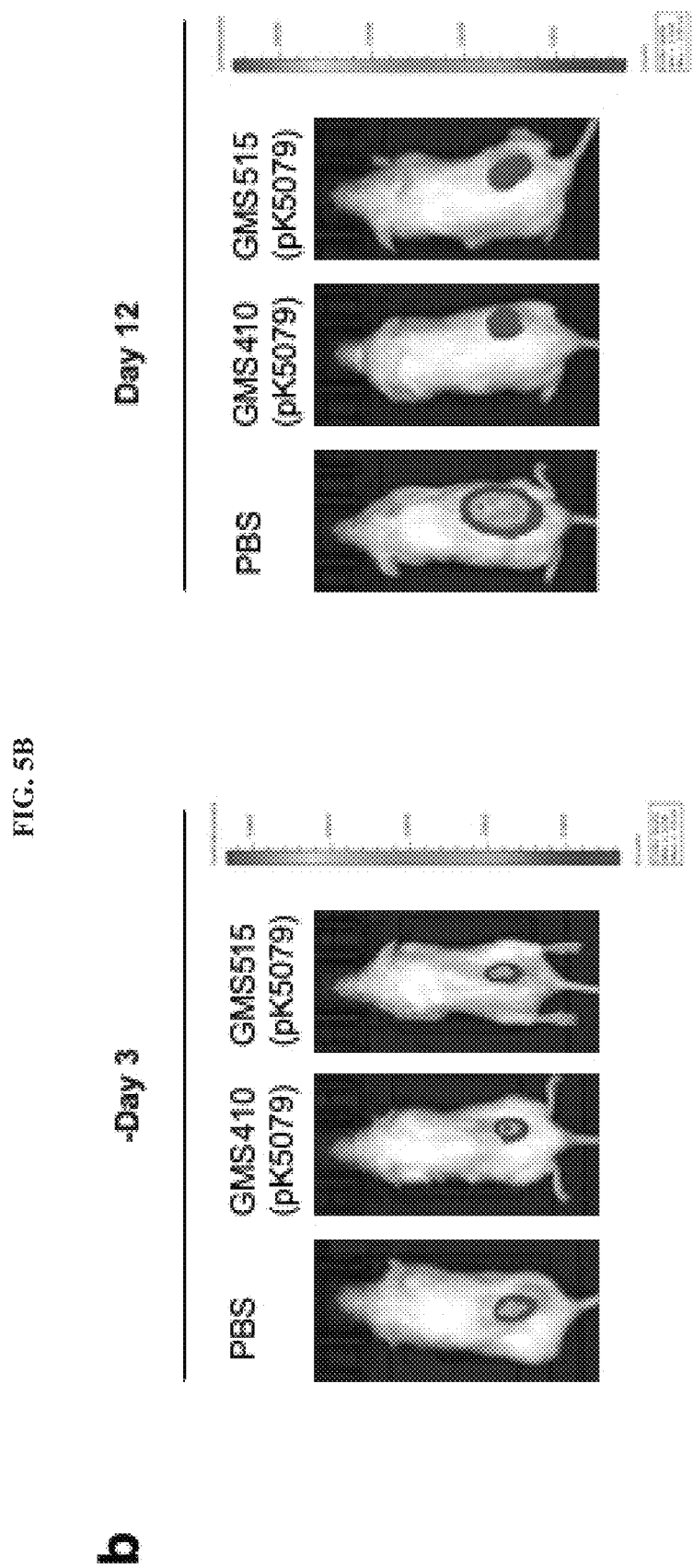
Figure 5C:
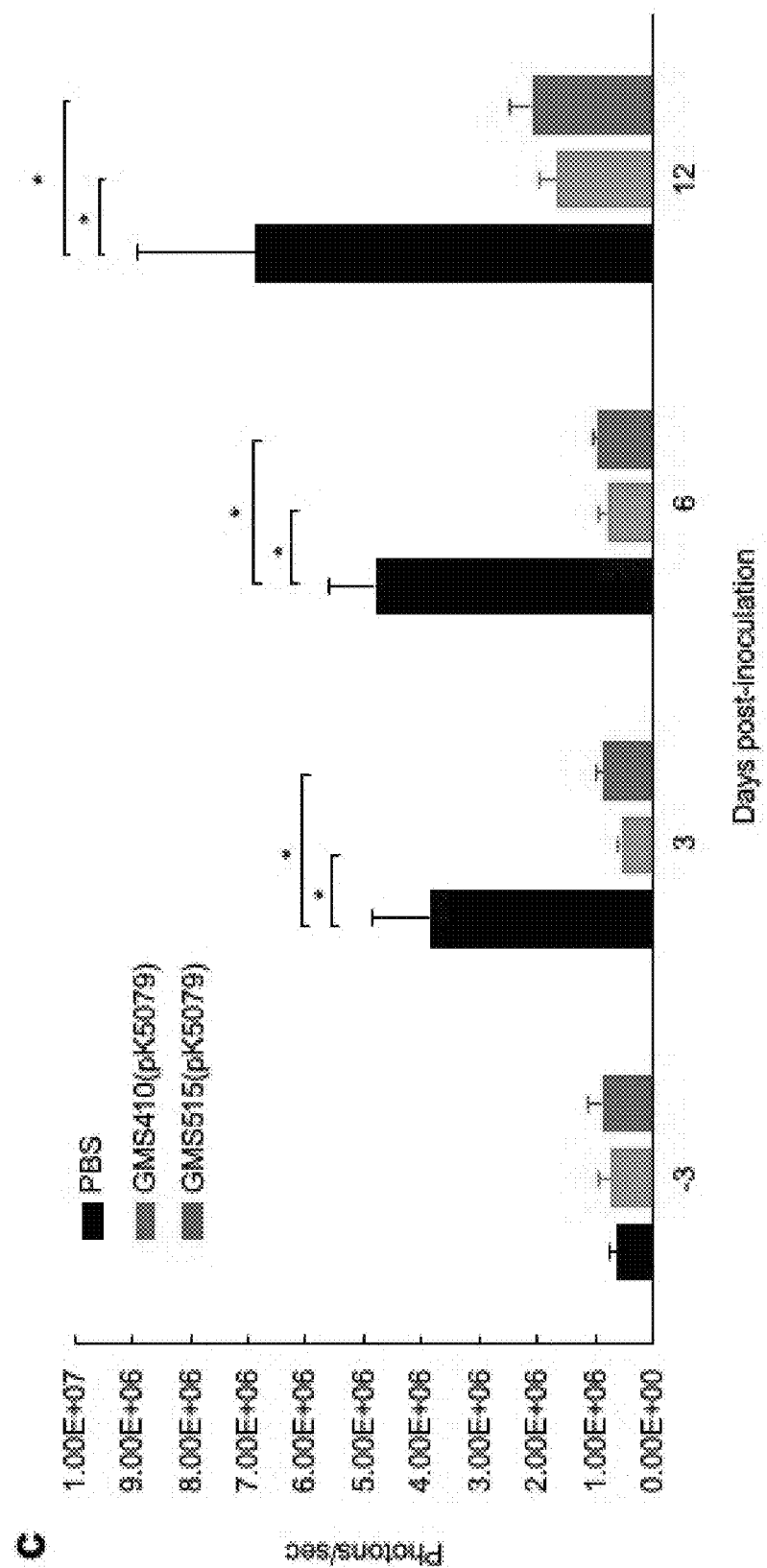

We further evaluated the efficacy of strains GMS410 (pK5079) and GMS515(pK5079) on cancer therapy in vivo using a human colon cancer HCT-116 cell xenograft mouse model (FIG. 5A). HCT-116 cells, which stably express luciferases, were subcutaneously injected into the flank area of immunocompromised NOD. Cg-Prkdcscid Il2rgtm1Wjl/SzJ (NSG™) mice. PBS, GMS410(pK5079), and GMS515 (pK5079) were IT injected into the NSG™ mice carrying tumors. The tumor growth was monitored through measuring cancer cell luciferase activity using a live imaging system following IT injection. As shown in FIG. 5B and 5C, the tumor luciferase activity of mice treated with GMS410 (pK5079) or GMS515(pK5079) is significantly lower than that in the control tumors (PBS-treated), suggesting that GMS410(pK5079) and GMS515(pK5079) inhibited HCT-116 cancer cell growth in vivo. In addition, Ki67 staining demonstrated that the proliferated cancer cells are much less in tumors treated with GMS410(pK5079) or GMS515 (pK5079) than that in the tumors treated with PBS, which confirmed that GMS410(pK5079) and GMS515(pK5079) were also able to inhibit human colon cancer cell growth in vivo (FIG. 5D). Furthermore, TUNEL assays showed more apoptotic cells in the tumor sections treated with GMS410 (pK5079) or GMS515(pK5079) than that in PBS-treated tumor sections (FIG. 5E). Taken together, these observations suggested that the reprogramming of chemotaxis system was an essential component of GMS anti-cancer effect and the self-eradicating GMS could effectively deliver TRAIL into the tumor microenvironment, and trigger Salmonella- and TRAIL-mediated tumor cell death.

Figure 6A:
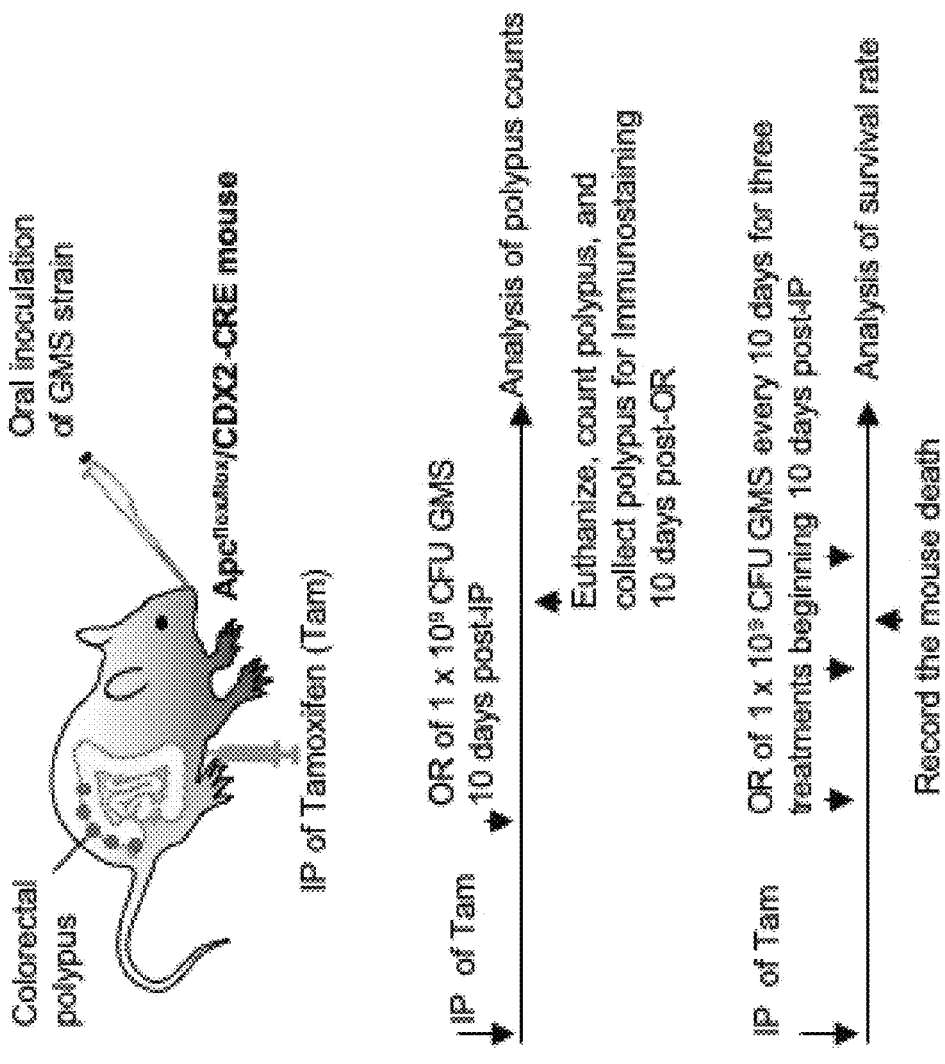
Figure 6B:
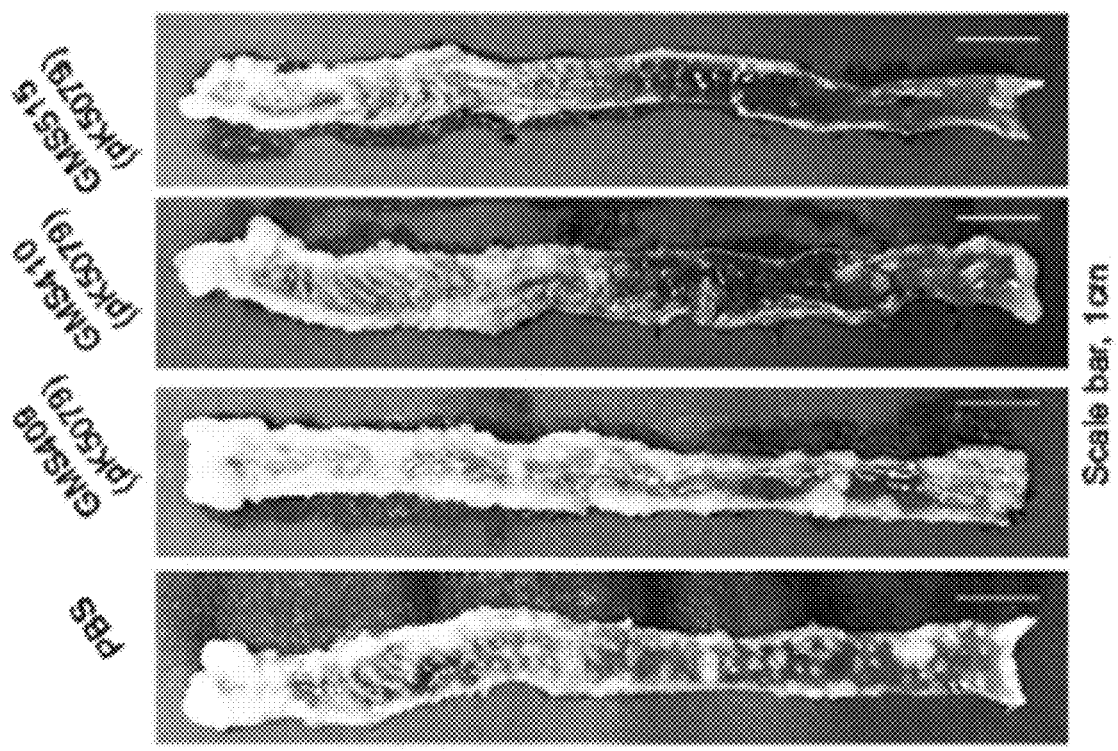
Figures 6C, 6D:
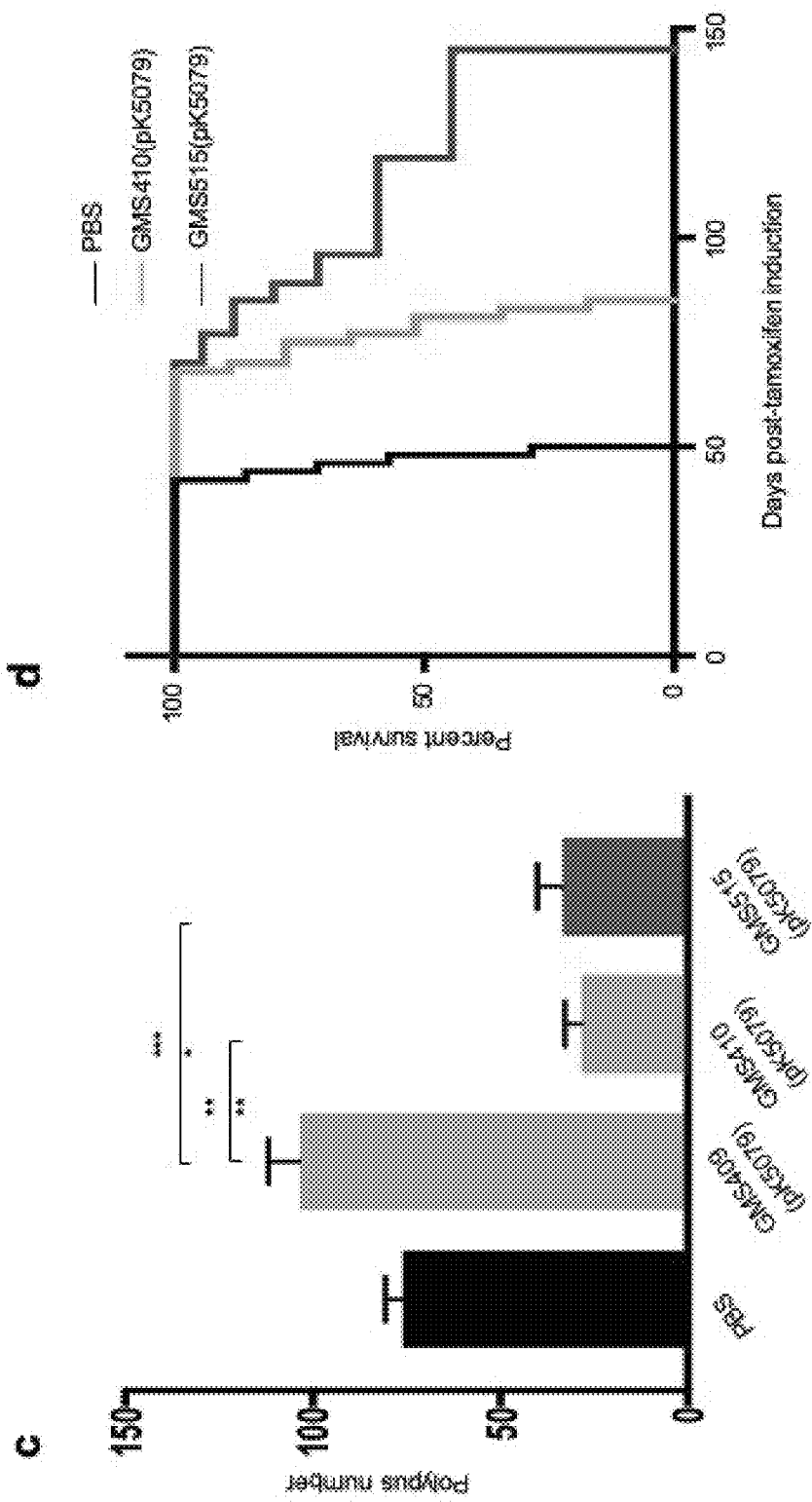

Evaluation of Reprogrammed GMS Strains Using a Transgenic Colon Tumor Mouse Model In addition to allograft and xenograft subcutaneous tumor models, GMS strains were evaluated in a transgenic $Apc^{flox/flox}$/CDX2-CRE colon tumor mouse model, which mimic human FAP associated colorectal cancer and sporadic colorectal cancer (FIG. 6A). Ten days after tamoxifen induction, mice were orally inoculated with PBS, GMS409 (pK5079), GMS410(pK5079), and GMS515(pK5079). Tumors in the colons and rectums were counted 10 days post-GMS treatment. As shown in FIGS. 6B and 6C, the number of polyps is significantly less in the mice treated with either GMS410(pK5079) or GMS515(pK5079), compared to the number of polyps in the mice treated with the PBS or GMS409(pK5079). Moreover, the survival time of the tamoxifen induced $Apc^{flox/flox}$/CDX2-CRE mice treated with GMS410(pK5079) and GMS515(pK5079) was dramatically increased when compared with the control group (FIG. 6D). In addition, more positive anti-Salmonella immunostaining was observed in the intestinal polyps treated with GMS410(pK5079) and GMS515(pK5079) strains than that in the samples treated with control strain GMS409(pK5079) (FIG. 6E). These results suggest that the reprogramming the chemotaxis system enables GMS410(pK5079) and GMS515 (pK5079) to navigate and colonize in tumor tissue following oral inoculation. Furthermore, a TUNEL assay was performed to detect apoptotic cells in the colon polypus. More apoptotic cells were discovered in polypus from the mice treated with GMS410(pK5079) and GMS515(pK5079) than that in the polypus from the mice treated with control GMS409(pK5079) (FIG. 6F). Overall, these data further demonstrate that GMS410(pK5079) 409 and GMS515

Figure 6G:
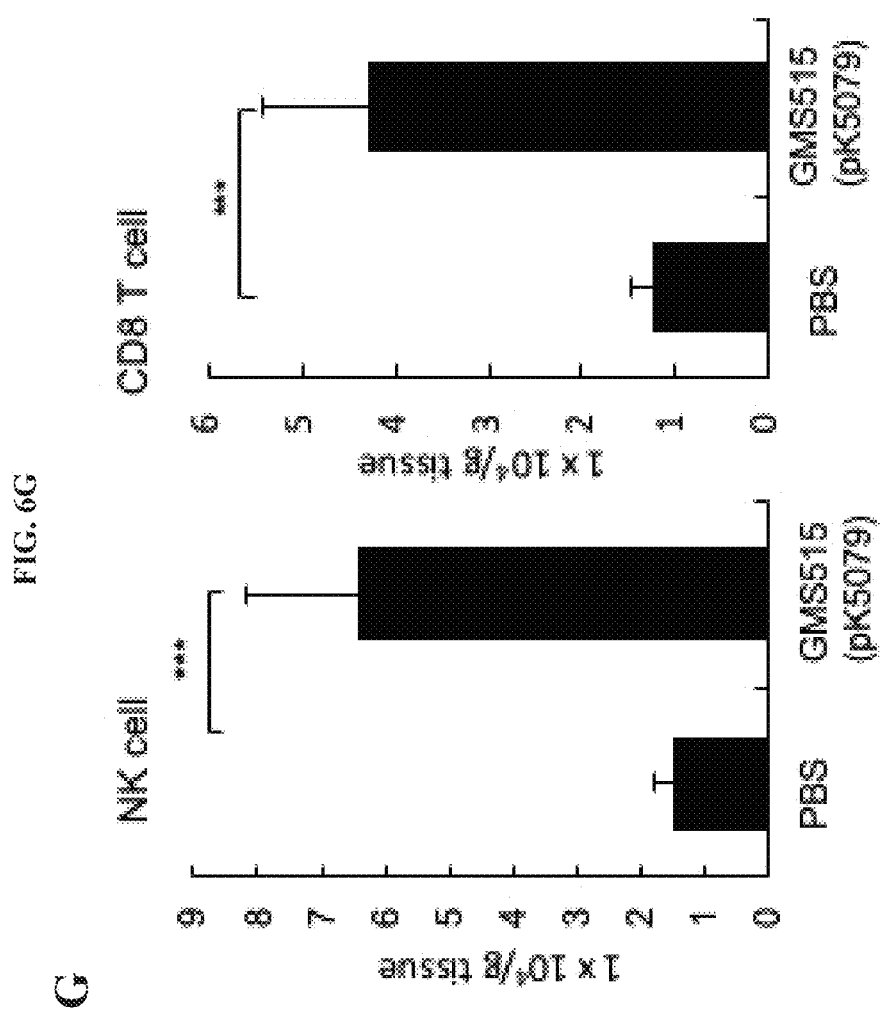

(pK5079) are able to navigate to the tumor and efficiently induce tumor cell apoptosis in vivo. Moreover, it was observed that GMS515(pK5079) significantly recruited natural killer cells (NKs) and CD8+ T-cells to the polyps, which may contribute to the observed suppression of tumor growth (FIG. 6G). Overall, these data further demonstrate that engineered *Salmonella* of strain GMS515(pK5079) navigate to the tumor, efficiently induce tumor cell apoptosis, and induce systemic tumor-specific antitumor immunity in vivo.

Figure 7A:
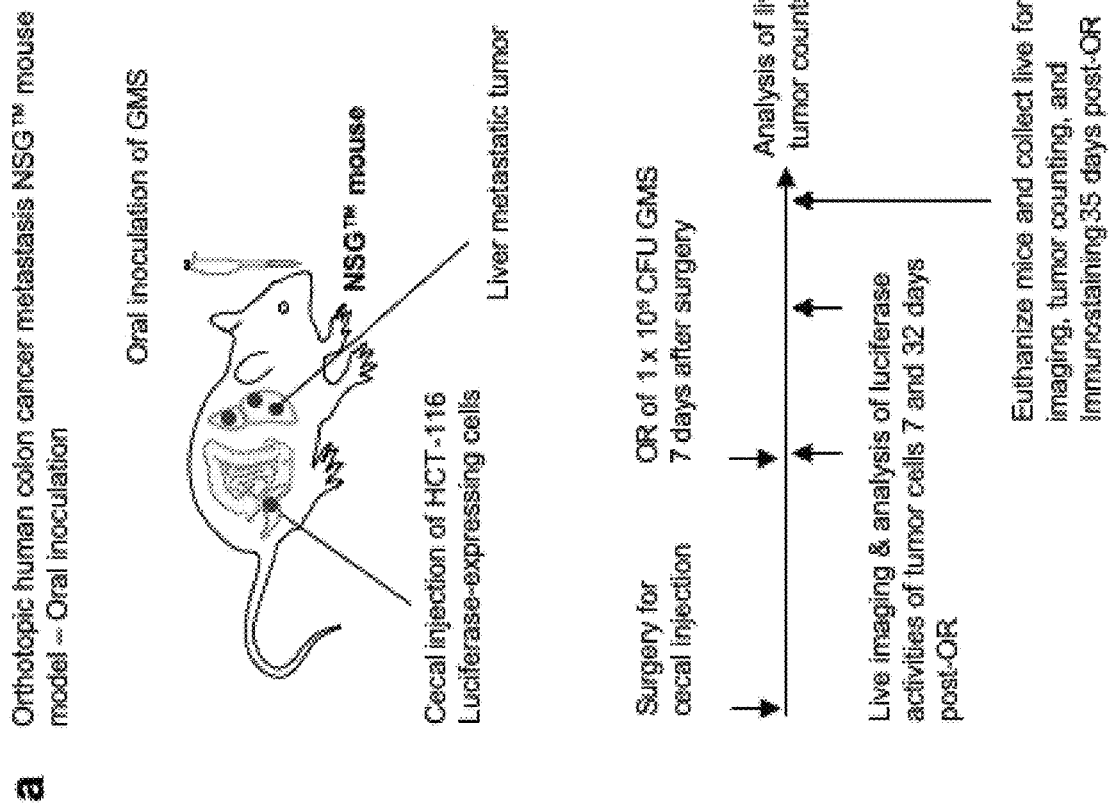
FIGS. 7a-7d demonstrate that reprogrammed GMS strains inhibit liver metastasis in a mouse model of orthotopic human colon cancer. a. Schematic route and timeline of GMS-based therapy. b. Representative live imaging of NSG™ mice, with cecally injected HCT-116 cells, orally treated with PBS or GMS strains. c. Representative imaging of liver metastasis and liver section H&E staining of the mice described in 7a. d. Numbers of liver metastatic tumors in mice (described in FIG. 7a) treated with PBS or GMS strains. The error bar indicates±SEM. (n=12,*** ρ<0.001).
Figure 7B:
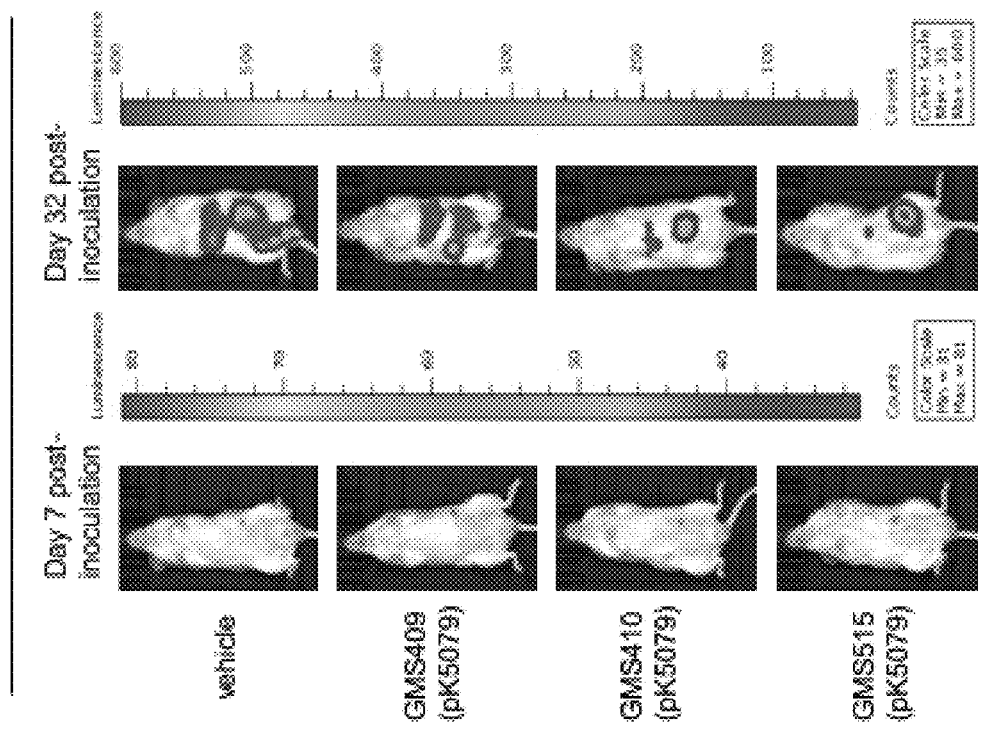
Figure 7C:
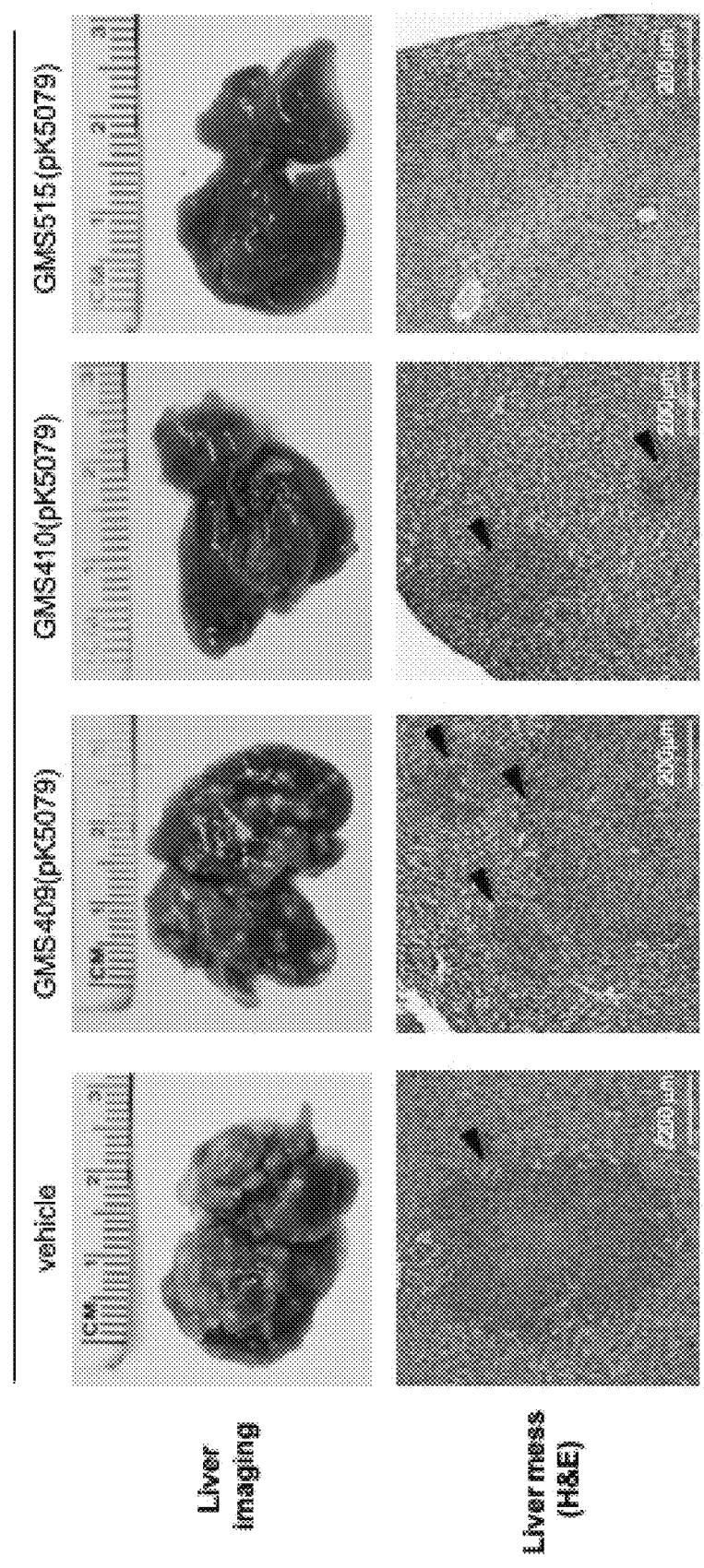
Figure 7D:
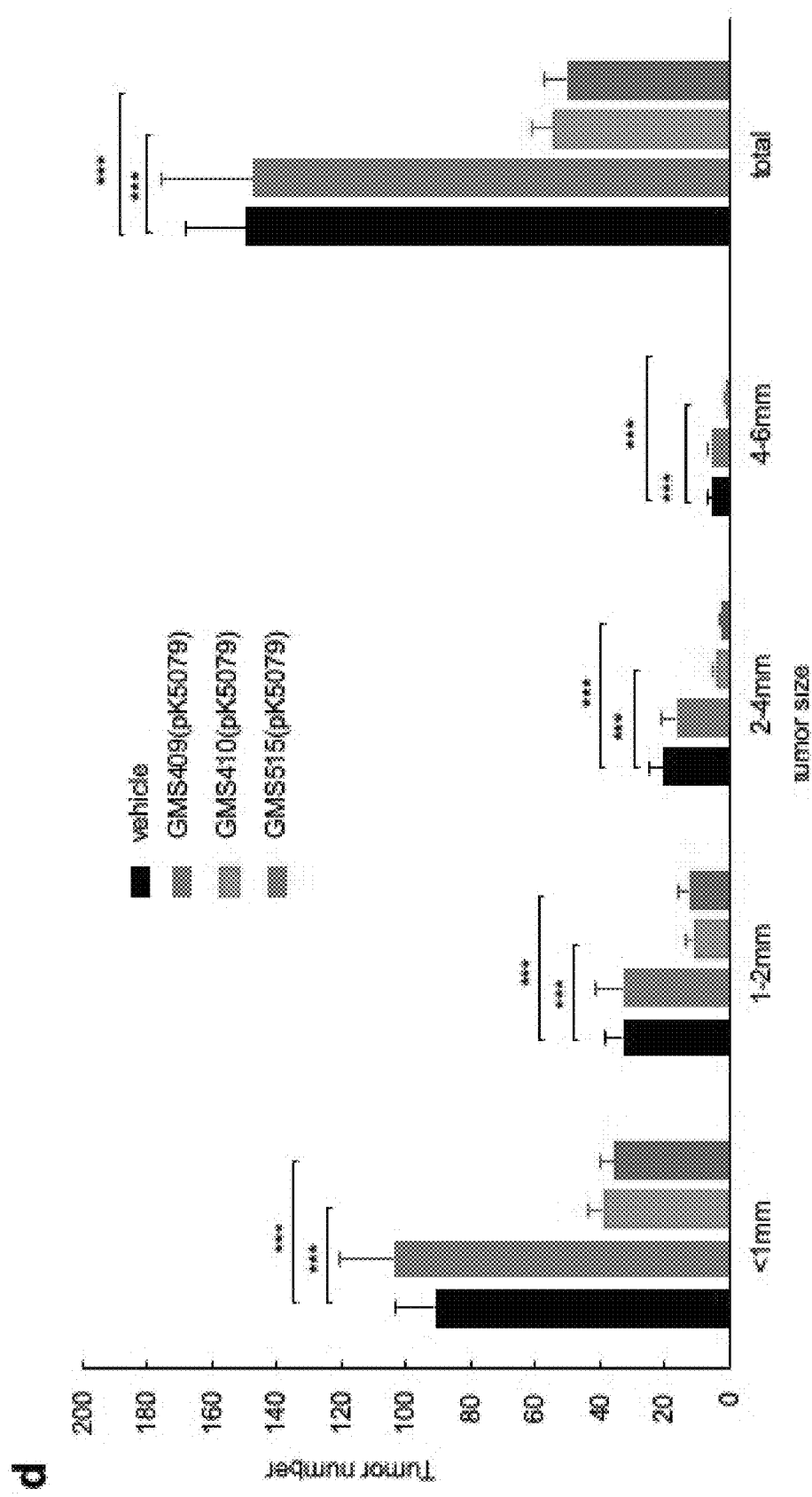

Reprogrammed GMS Strains-Based Therapy for Metastatic Cancer in an Orthotopic Xenograft Mouse Model Colorectal cancer is one of the leading causes of cancer mortality because of its metastasis. Liver is the most common organ for colon cancer metastasis. To investigate whether GMS410(pK5079) and GMS515(pK5079) are able to inhibit liver metastasis from orthotopically implanted colon cancer, the HCT-116 cells expressing luciferase were injected into the cecum wall of NSG™ mice. At day 7 post-surgery, mice were orally inoculated with PBS, GMS409(pK5079), GMS410(pK5079), or GMS515 (pK5079) once per week for 5 weeks (FIG. 7A). Tumor growth and metastasis were monitored using a live imaging system (FIG. 7B). Metastatic tumor number and size were analyzed at week 5 post-inoculation. As shown in FIGS. 7C and 7D, colon cancer cells grew from cecum and metastasized to adjacent tissue and distant organ liver in the groups treated with PBS and GMS409(pK5079). However, much less local and distance metastasis was observed in the mice treated with GMS410(pK5079) or GMS515(pK5079). These data indicate that both GMS410(pK5079) and GMS515(pK5079) are capable of reducing tumor metastasis.

Discussion

Despite many advances in conventional methods such as chemo- and radiation-therapy, cancer treatment is still far from optimal. Current cancer therapies frequently encounter challenges including nonspecific systemic distribution of antitumor agents, inadequate drug concentrations reaching the tumor site, intolerable cytotoxicity and development of multiple drug resistance. As with any cancer therapy, the key issue is to achieve the desired concentration of the therapeutic agent specifically in tumor sites, thereby destroying cancerous cells while minimizing damage to normal cells. Bacterial cancer therapies offer unique features that can overcome these obstacles. However, intrinsic bacterial toxicity and tumor-targeting efficiency are two major concerns for the bacterial approach in cancer therapy. We report here that we have now addressed the concerns by constructing GMS strains with enhanced chemotaxis systems that are attracted by tumor released small molecules to confer tumor-navigating feature. Moreover, the regulated delayed attenuation and programmed self-eradicating features designed into these *S. Typhimurium* strains to enable them to efficiently colonize in tumors and allow the release of the tumoricidal contents, TRAIL, after cell lysis. We have demonstrated that the genetically engineered tumor navigating and self-eradicating GMS410(pK5079) and GMS515 (pK5079) strains not only improve the safety of cancer treatment, but also efficiently target tumor tissue, release TRAIL into the tumor tissues, induce significant tumor regression and extend the survival rate in both allograft and xenograft colon cancer mouse models. We also validate the efficacy of anti-cancer metastasis using *Salmonella* based-cancer therapies in the orthotopic human colon cancer xenograft mouse model created through cecum wall surgical microinjection, which drives tumor foci to the most relevant metastatic sites observed in humans. Most importantly, orally administered GMS410(pK5079) and GMS515 (pK5079) successfully achieved metastasis blockage in such mouse models. In addition, we are the first to evaluate *Salmonella*-based cancer therapeutics in an inducible APC gene mutation mouse model, which can better mimic human familial adenomatous polyposis disease. The results proved that GMS410(pK5079) and GMS515(pK5079) strains effectively suppressed tumor progression. In addition, GMS515 (pK5079) successfully recruited and activated significant anti-cancer immune cells to the tumor microenvironment. As such, these GMS strains show tremendous potential, either alone or in combination with other treatments, to make an important contribution in cancer therapy.

The present disclosure has described one or more preferred embodiments, and it should be appreciated that many equivalents, alternatives, variations, and modifications, aside from those expressly stated, are possible and within the scope of the disclosure.

I claim:

1. A genetically modified *Salmonella* bacterium, wherein the bacterium comprises:
   (a) SEQ ID NO: 7, wherein SEQ ID NO: 7 includes a recombinant gene encoding human TNF-related Apoptosis-inducing Ligand (TRAIL);
   (b) the following seven modifications:
   $\Delta P_{murA}$ araC $P_{BAD}$ murA,
   $\Delta$asdA::TT araC $P_{BAD}$ c2 $\Delta$(araC $P_{BAD}$)::P22 $P_R$ araBAD,
   $\Delta$(wza-wcaM),
   $\Delta$relA::araC $P_{BAD}$ lacI TT,
   $\Delta$pagP::$P_{lpp}$lpxE, and
   $\Delta$endA; and
   (c) one or more of the following three modifications: $\Delta P_{tar}$::$P_{trc}$ $\Delta$lacO tar, $\Delta P_{tsr}$::$P_{trc}$ $\Delta$lacO tsr, and $\Delta$trg.

2. The genetically modified *Salmonella* bacterium of claim 1, wherein the bacterium is capable of self-eradication in non-tumor cells.

3. The genetically modified *Salmonella* bacterium of claim 1, wherein the bacterium comprises the following 3 modifications $\Delta P_{tar}$::$P_{trc}$ $\Delta$lacO tar, $\Delta P_{tsr}$::$P_{trc}$ $\Delta$lacO tsr, and $\Delta$trg.

4. The genetically modified *Salmonella* bacterium of claim 1, wherein the bacterium is S. *Typhimurium*.

5. The genetically modified *Salmonella* bacterium of claim 1, wherein the bacterium comprises $\Delta P_{tar}$::$P_{trc}$ $\Delta$lacO tar.

6. A method of treating cancer in a subject in need thereof comprising administering an effective amount of the genetically modified *Salmonella* bacterium of claim 1 to the subject, whereby the genetically modified *Salmonella* bacterium treats cancer in the subject.

7. The method of claim 6, wherein administering comprises oral administration or intra-tumoral injection of the genetically modified *Salmonella* bacterium.

8. A method for stimulating tumoricidal activity in a subject comprising administering an effective amount of the genetically modified *Salmonella* bacterium of claim 1 to the subject, whereby the genetically modified *Salmonella* bacterium induces tumoricidal activity in the subject.

9. The method of claim 8, wherein administering comprises oral administration or intra-tumoral injection of the genetically modified *Salmonella* bacterium.

10. The method of claim 8, wherein the subject has cancer.

11. A genetically modified *Salmonella* bacterium, wherein the bacterium comprises:
    (a) SEQ ID NO:7, wherein SEQ ID NO: 7 includes a recombinant gene encoding human TNF-related Apoptosis-inducing Ligand (TRAIL);
    (b) the following seven modifications
    $\Delta P_{murA}$ araC $P_{BAD}$ murA,
    $\Delta$asdA::TT araC $P_{BAD}$ c2 $\Delta$(araC $P_{BAD}$)::P22 $P_R$ araBAD,
    $\Delta$(wza-wcaM),
    $\Delta$pmi,
    $\Delta$relA::araC $P_{BAD}$ lacI TT, $\Delta$pagP::$P_{lpp}$ lpxE, and $\Delta$endA;
    (c) one or more of the following three modifications: $\Delta P_{tar}$::$P_{trc}$ $\Delta$lacO tar, $\Delta P_{tsr}$::$P_{trc}$ $\Delta$lacO tsr, and $\Delta$trg; and
    (d) one or more of the following mutations: $\Delta$sseL, $\Delta$spvD, and $\Delta$ssrAB.

12. The genetically modified *Salmonella* bacterium of claim 11, wherein the bacterium is capable of self-eradication in non-tumor cells.

13. The genetically modified *Salmonella* bacterium of claim 11, wherein the bacterium comprises mutations $\Delta$sseL, $\Delta$spvD, and $\Delta$ssrAB.

14. The genetically modified *Salmonella* bacterium of claim 11, wherein the bacterium is S. *Typhimurium*.

15. The genetically modified *Salmonella* bacterium of claim 11, wherein the bacterium comprises $\Delta P_{tar}$::$P_{trc}$$\Delta$lacO tar.

16. A method of treating cancer in a subject in need thereof comprising administering an effective amount of the genetically modified *Salmonella* bacterium of claim 11 to the subject, whereby the genetically modified *Salmonella* bacterium treats cancer in the subject.

17. The method of claim 16, wherein administering comprises oral administration or intra-tumoral injection of the genetically modified *Salmonella* bacterium.

18. A method for stimulating tumoricidal activity in a subject comprising administering an effective amount of the genetically modified *Salmonella* bacterium of claim 11 to the subject, whereby the genetically modified *Salmonella* bacterium induces tumoricidal activity in the subject.

19. The method of claim 18, wherein administering comprises oral administration or intra-tumoral injection of the genetically modified *Salmonella* bacterium.

20. The method of claim 18, wherein the subject has cancer.

* * * * *

UNITED STATES PATENT AND TRADEMARK OFFICE
CERTIFICATE OF CORRECTION

PATENT NO. : 11,519,007 B2  
APPLICATION NO. : 17/433222  
DATED : December 6, 2022  
INVENTOR(S) : Wei Kong Page 1 of 1

It is certified that error appears in the above-identified patent and that said Letters Patent is hereby corrected as shown below:

In the Claims

Claim 1, Column 87, Lines 11-12, "$\Delta$(wza-wcaM), $\Delta$relA::araC $P_{BAD}$ lacI TT" should be --$\Delta$(wza-wcaM), $\Delta$pmi, $\Delta$relA::araC $P_{BAD}$ lacI TT--.

Claim 1, Column 87, Line 17, "$\Delta P_{tar}::P_{trc}$ $\Delta$lacO tar," should be --$\Delta P_{tar}::P_{trc}$ $_{\Delta lacO}$ tar--.

Claim 1, Column 87, Line 17, "$\Delta P_{tsr}::P_{trc}$ $\Delta$lacO tsr," should be --$\Delta P_{tsr}::P_{trc}$ $_{\Delta lacO}$ tsr--.

Claim 3, Column 87, Line 23, "$\Delta P_{tar}::P_{trc}$ $\Delta$lacO tar," should be --$\Delta P_{tar}::P_{trc}$ $_{\Delta lacO}$ tar--.

Claim 3, Column 87, Line 23, "$\Delta P_{tsr}::P_{trc}$ $\Delta$lacO tsr," should be --$\Delta P_{tsr}::P_{trc}$ $_{\Delta lacO}$ tsr--.

Claim 5, Column 87, Line 28, "$\Delta P_{tar}::P_{trc}$ $\Delta$lacO tar" should be --$\Delta P_{tar}::P_{trc}$ $_{\Delta lacO}$ tar--.

Claim 11, Column 88, Line 16, "$\Delta P_{tar}::P_{trc}$ $\Delta$lacO tar" should be --$\Delta P_{tar}::P_{trc}$ $_{\Delta lacO}$ tar--.

Claim 11, Column 88, Line 16, "$\Delta P_{tsr}::P_{trc}$ $\Delta$lacO tsr" should be --$\Delta P_{tsr}::P_{trc}$ $_{\Delta lacO}$ tsr--.

Claim 15, Column 88, Line 27, "$\Delta P_{tar}::P_{trc}$ $\Delta$lacO tar" should be --$\Delta P_{tar}::P_{trc}$ $\Delta_{lacO}$ tar--.

Signed and Sealed this  
Sixteenth Day of April, 2024

Katherine Kelly Vidal  
*Director of the United States Patent and Trademark Office*

SEQUENCE LISTING

```
<160> NUMBER OF SEQ ID NOS: 44

<210> SEQ ID NO 1
<211> LENGTH: 94
<212> TYPE: DNA
<213> ORGANISM: Artificial Sequence
<220> FEATURE:
<223> OTHER INFORMATION: Synthetic- Promoter: Ptrc lacO deletion

<400> SEQUENCE: 1
attctgaaat gagctgttga caattaatca tccggctcgt ataatgtgta gatgcgtagg      60
cacctgttac gacgaaccac acaggaaaca gacc                                  94

<210> SEQ ID NO 2
<211> LENGTH: 1756
<212> TYPE: DNA
<213> ORGANISM: Artificial Sequence
<220> FEATURE:
<223> OTHER INFORMATION: Synthetic- tar deletion-insertion mutation
```

-continued

```
<400> SEQUENCE: 2
attctgaaat gagctgttga caattaatca tccggctcgt ataatgtgta gatgcgtagg      60
cacctgttac gacgaaccac acaggaaaca gaccatgttt aaccgtatcc gcgttgtcac     120
aatgctgatg atggtgctgg gggttttcgc actgctacag cttgtttccg gtggtttgct     180
gttttcttca ttacagcata accagcaagg ttttgttatt tctaacgaat tacgtcagca     240
acaaagcgaa ctcacgtcga catgggactt aatgctgcaa acgcgcatta acctgagccg     300
ctccgccgca cgcatgatga tggacgcttc taaccagcag agcagcgcca aaacggattt     360
actccagaat gcaaaaacga ctctcgcaca ggcggcggcg cactacgcca atttcaaaaa     420
tatgacgcca ttgccagcga tggcggaggc cagcgcgaac gtcgatgaaa aatatcagcg     480
ctatcaggcc gcattagccg aacttattca gtttctggac aatggcaata tggatgccta     540
cttcgcccag ccaacccagg gaatgcaaaa cgcgttgggc gaggcgctgg gcaattacgc     600
ccgggtgagc gaaaacctgt accgccagac atttgatcaa agtgctcatg actaccgttt     660
tgcgcaatgg caactggggg ttcttgcggt cgtgctggtg ctgattttga tggtggtttg     720
gttcggcatt cgtcatgccc tgcttaaccc attagcgcga gtgattactc atatccgtga     780
aattgccagc ggcgatctga cgaaaacgct caccgtctca ggacgtaatg aaattggcga     840
actggcggga acggttgaac atatgcaacg ctcgctgatt gacaccgtaa cgcaggttcg     900
tgaaggttcg gatgcgattt attccggcac cagtgaaatt gccgccggta ataccgacct     960
ctcttcccgt accgaacagc aggcctccgc tctggaggag acggctgcca gcatggaaca    1020
actgacggcc accgtgaagc aaaacgccga taacgcccgc caggcttcgc aactggcgca    1080
aagcgcctcc gagaccgcgc gtcatggcgg caaagtggtc gacggcgtag taaacactat    1140
gcacgaaatt gccgacagtt cgaaaaaaat cgctgacatt atcagcgtta tcgacggtat    1200
tgccttccag actaacattc tggcgctgaa cgcggcggta gaagcggcgc gcgcgggaga    1260
gcagggggcg ggttttgcgg tcgtggcagg cgaggtgcgt aatctggcca gccgcagcgc    1320
ccaggcggcg aaagaaataa aagcgttgat tgaagattcc gtctcgcgtg tcgataccgg    1380
ttctgtgctg gtggaaagcg ccggggaaac catgactgac atcgtcaatg ccgttacgcg    1440
cgtcacggat atcatgggcg aaatcgcctc cgcctcggat gagcaaagcc ggggtatcga    1500
tcaggtcgct ttggccgttt ccgaaatgga tcgcgtaacg caacgaaacg cctcgctggt    1560
tcaggaatcc gcagcggccg ccgccgcgct ggaagagcag gccagccgtc tgacccaggc    1620
ggtatcggct ttccgcctgg catcgcgacc gctggcggta aataaacctg agatgcgttt    1680
gtcagtgaac gctcagtccg gcaatacgcc gcagtcatta gccgccaggg atgatgcgaa    1740
ctgggaaacc ttctga                                                    1756

<210> SEQ ID NO 3
<211> LENGTH: 6177
<212> TYPE: DNA
<213> ORGANISM: Artificial Sequence
<220> FEATURE:
<223> OTHER INFORMATION: Synthetic- plasmid pK4946: suicide vector for
      construction of tar deletion-insertion mutation

<400> SEQUENCE: 3
gatccttttt aacccatcac atatacctgc cgttcactat tatttagtga aatgagatat      60
tatgatattt tctgaattgt gattaaaaag gcaactttat gcccatgcaa cagaaactat     120
aaaaaataca gagaatgaaa agaaacagat agattttta gttctttagg cccgtagtct     180
```

-continued

```
gcaaatcctt ttatgatttt ctatcaaaca aaagaggaaa atagaccagt tgcaatccaa    240
acgagagtct aatagaatga ggtcgaaaag taaatcgcgc gggtttgtta ctgataaagc    300
aggcaagacc taaaatgtgt aaagggcaaa gtgtatactt tggcgtcacc ccttacatat    360
tttaggtctt tttttattgt gcgtaactaa cttgccatct tcaaacagga gggctggaag    420
aagcagaccg ctaacacagt acataaaaaa ggagacatga acgatgaaca tcaaaaagtt    480
tgcaaaacaa gcaacagtat taaccttcac taccgcactg ctggcaggag cgcaactca    540 agcgtttgcg aaagaaacga accaaaagcc atataaggaa acatacggca tttcccatat    600
tacacgccat gatatgctgc aaatccctga acagcaaaaa atgaaaaat atcaagttcc    660 tgagttcgat tcgtccacaa ttaaaaatat ctcttctgca aaaggcctgg acgtttggga    720
cagctggcca ttacaaaacg ctgacggcac tgtcgcaaac tatcacgcct accacatcgt    780
ctttgcatta gccggagatc ctaaaaatgc ggatgacaca tcgatttaca tgttctatca    840
aaaagtcggc gaaacttcta ttgacagctg gaaaaacgct ggccgcgtct ttaaagacag    900
cgacaaattc gatgcaaatg attctatcct aaaagaccaa acacaagaat ggtcaggttc    960
agccacattt acatctgacg gaaaaatccg tttattctac actgatttct ccggtaaaca   1020
ttacggcaaa caaacactga caactgcaca agttaacgta tcagcatcag acagctcttt   1080
gaacatcaac ggtgtagagg attataaatc aatctttgac ggtgacggaa aaacgtatca   1140
aaatgtacag cagttcatcg atgaaggcaa ctacagctca ggcgacaacc atacgctgag   1200
agatcctcac tacgtagaag ataaaggcca caatactta gtatttgaag caaacactgg   1260
aactgaagat ggctaccaag cgaagaatc tttatttaac aaagcatact atggcaaaag   1320
cacatcattc ttccgtcaag aaagtcaaaa acttctgcaa agcgataaaa acgcacggc   1380 tgagttagca acggcgctc tcggtatgat tgagctaaac gatgattaca cactgaaaaa   1440
agtgatgaaa ccgctgattg catctaacac agtaacagat gaaattgaac gcgcgaacgt   1500
cttaaaaatg aacggcaaat ggtatctgtt cactgactcc cgcggatcaa aaatgacgat   1560
tgacggcatt acgtctaacg atatttacat gcttggttat gtttctaatt ctttaactgg   1620
cccatacaag ccgctgaaca aaactggcct tgtgttaaaa atggatcttg atcctaacga   1680
tgtaaccttt acttactcac acttcgctgt acctcaagcg aaaggaaaca atgtcgtgat   1740
tacaagctat atgacaaaca gaggattcta cgcagacaaa caatcaacgt ttgcgcccag   1800
cttcctgctg aacatcaaag gcaagaaaac atctgttgtc aaagacagca tccttgaaca   1860
aggacaatta acagttaaca aataaaaacg caaaagaaaa tgccgatatc ctattggcat   1920 tttctttat ttcttatcaa cataaaggtg aatcccatat gaactatata aaagcaggca   1980
aatggctaac cgtattccta acctttttgaa ttcgatcgct agtttgtttt gactccatcc   2040
attagggctt ctaaaacgcc ttctaaggcc atgtcagccg ttaagtgttc ctgtgtcact   2100
gaaaattgct ttgagaggct ctaagggctt ctcagtgcgt acatccctg gcttgttgtc   2160 cacaaccgtt aaaccttaaa agctttaaaa gccttatata ttcttttttt tcttataaaa   2220
cttaaaacct tagaggctat ttaagttgct gatttatatt aattttattg ttcaaacatg   2280
agagcttagt acgtgaaaca tgagagctta gtacgttagc catgagagct tagtacgtta   2340
gccatgaggg tttagttcgt taaacatgag agcttagtac gttaaacatg agagcttagt   2400
acgtgaaaca tgagagctta gtacgtacta tcaacaggtt gaactgctgg atcgatcctt   2460
tttgtccggt gttgggttga aggtgaagcc ggtcggggcc gcagcggggg ccggcttttc   2520
agccttgccc ccctgcttcg gccgccgtgg ctccggcgtc ttgggtgccg gcgcgggttc   2580
```

```
cgcagccttg gcctgcggtg cgggcacatc ggcgggcttg ccttgatgt gccgcctggc    2640 gtgcgagcgg aacgtctcgt aggagaactt gaccttcccc gtttcccgca tgtgctccca    2700
aatggtgacg agcgcatagc cggacgctaa cgccgcctcg acatccgccc tcaccgccag    2760
gaacgcaacc gcagcctcat cacgccggcg cttcttggcc gcgcgggatt caacccactc    2820
ggccagctcg tcggtgtagc tctttggcat cgtctctcgc ctgtcccctc agttcagtaa    2880
tttcctgcat ttgcctgttt ccagtcggta gatattccac aaaacagcag ggaagcagcg    2940
cttttccgct gcataaccct gcttcggggt cattatagcg attttttcgg tatatccatc    3000 cttttttcgca cgatatacag gattttgcca aagggttcgt gtagactttc cttggtgtat    3060
ccaacggcgt cagccgggca ggataggtga agtaggccca cccgcgagcg ggtgttcctt    3120
cttcactgtc ccttattcgc acctggcggt gctcaacggg aatcctgctc tgcgaggctg    3180
gccggctacc gccggcgtaa cagatgaggg caagcggatg gctgatgaaa ccaagccaac    3240
caggaagggc agcccaccta tcaaggtgta ctgccttcca gacgaacgaa gagcgattga    3300
ggaaaaggcg gcggcggccg gcatgagcct gtcggcctac ctgctggccg tcggccaggg    3360
ctacaaaatc acgggcgtcg tggactatga gcacgtccgc gagctggccc gcatcaatgg    3420
cgacctgggc cgcctgggcg gcctgctgaa actctggctc accgacgacc cgcgcacggc    3480
gcggttcggt gatgccacga tcctcgccct gctggcgaag atcgaagaga agcaggacga    3540
gcttggcaag gtcatgatgg gcgtggtccg cccgagggca gagccatgac ttttttagcc    3600 gctaaacgg ccgggggggtg cgcgtgattg ccaagcacgt ccccatgcgc tccatcaaga    3660
agagcgactt cgcggagctg gtgaagtaca tcaccgacga gcaaggcaag accgagcgcc    3720
tgggtcacgt gcgcgtcacg aactgcgagg caaacaccct gccgctgtc atggccgagg    3780 tgatggcgac ccagcacggc aacacccgtt ccgaggccga caagacctat cacctgctgg    3840
ttagcttccg cgcgggagag aagcccgacg cggagacgtt gcgcgcgatt gaggaccgca    3900
tctgcgctgg gcttggcttc gccgagcatc agcgcgtcag tgccgtgcat cacgacaccg    3960
acaacctgca catccatatc gccatcaaca agattcaccc gacccgaaac accatccatg    4020
agccgtatcg ggcctaccgc gccctcgctg acctctgcgc gacgctcgaa cgggactacg    4080
ggcttgagcg tgacaatcac gaaacgcggc agcgcgtttc cgagaaccgc gcgaacgaca    4140
tggagcggca cgcgggcgtg gaaagcctgg tcggctggat cgggcctaa atacctgtga    4200 cggaagatca cttcgcagaa taaataaatc ctggtgtccc tgttgatacc gggaagccct    4260
gggccaactt ttggcgaaaa tgagacgttg atcggcacgt aagaggttcc aactttcacc    4320
ataatgaaat aagatcacta ccgggcgtat ttttgagtt atcgagattt tcaggagcta    4380
aggaagctaa aatggagaaa aaatcactg gatataccac cgttgatata tcccaatggc    4440
atcgtaaaga acattttgag gcatttcagt cagttgctca atgtacctat aaccagaccg    4500
ttcagctgga tattacggcc ttttttaaaga ccgtaaagaa aaataagcac aagttttatc    4560
cggcctttat tcacattctt gcccgcctga tgaatgctca tccggaattc cgtatggcaa    4620
tgaaagacgg tgagctggtg atatgggata tgttcaccc ttgttacacc gttttccatg    4680
agcaaactga aacgttttca tcgctctgga gtgaatacca cgacgatttc cggcagtttc    4740
tacacatata ttcgcaagat gtggcgtgtt acggtgaaaa cctggcctat ttccctaaag    4800 ggttattga gaatatgttt ttcgtctcag ccaatccctg ggtgagtttc accagttttg    4860
atttaaacgt ggccaatatg gacaacttct tcgccccgt tttcaccatg gcaaatatt    4920
```

-continued

```
atacgcaagg cgacaaggtg ctgatgccgc tggcgattca ggttcatcat gccgtctgtg    4980
atggcttcca tgtcggcaga atgcttaatg aattacaaca gtactgcgat gagtggcagg    5040
gcggggcgta atttttttaa ggcagttatt ggtgcccttg aacgcctggt gctacgcctg    5100
aataagtgat agggcccgat cccaagcttc ttctagaggt accgacttca tcgccaatac    5160
accggccttt ataaaagggg tgactaacct gcgcggcgtg attgtcccca ttgtcgatct    5220
gcgcgtgaaa ttctgcgaag cgacgttga gtacgatgac aatacggtag tgatcgtact    5280
gaatctgggg caacgcgtcg tcgggatagt ggtagacggc gtgtctgacg tactgtcgtt    5340
aacggcggaa cagatccgtc cggcgccaga atttgccgtg accttgtcaa cagaatattt    5400
gacgggattg ggcgcgctcg gcgagcgtat gctgattctg gtgaatatcg aaaaactgct    5460
taacagcgaa gagatggcgc tgctggatat cgcagcatca cacgtcgcgt aataacgttg    5520
ccggatggcg tcgcgccatc cggcaatatt caccgttatg cttccgccag cggtgagagt    5580
gcctcttcat cgcccgcgat tctgaaatga gctgttgaca attaatcatc cggctcgtat    5640
aatgtgtaga tgcgtaggca cctgttacga cgaaccacac aggaaacaga ccatgtttaa    5700
ccgtatccgc gttgtcacaa tgctgatgat ggtgctgggg gttttcgcac tgctacagct    5760
tgtttccggt ggtttgctgt tttcttcatt acagcataac cagcaaggtt ttgttatttc    5820
taacgaatta cgtcagcaac aaagcgaact cacgtcgaca tgggacttaa tgctgcaaac    5880
gcgcattaac ctgagccgct ccgccgcacg catgatgatg gacgcttcta accagcagag    5940
cagcgccaaa acggatttac tccagaatgc aaaaacgact ctcgcacagg cggcggcgca    6000
ctacgccaat ttcaaaaata tgacgccatt gccagcgatg gcggaggcca gcgcgaacgt    6060
cgatgaaaaa tatcagcgct atcaggccgc attagccgaa cttattcagt ttctggacaa    6120
tggcaatatg gatgcctact tcttgtcgca tgcgatatcg agctctcccg ggaattc     6177
```

<210> SEQ ID NO 4
<211> LENGTH: 1756
<212> TYPE: DNA
<213> ORGANISM: Artificial Sequence
<220> FEATURE:
<223> OTHER INFORMATION: Synthetic- tsr deletion-insertion mutation

<400> SEQUENCE: 4

```
attctgaaat gagctgttga caattaatca tccggctcgt ataatgtgta gatgcgtagg      60
cacctgttac gacgaaccac acaggaaaca gaccatgtta aagcgaatta aaattgttac    120
cagcttactg ctggtattgg cgctatttgg ccttttacaa ctgacatccg gcgggctgtt    180
cttcaactcg ctgaagaatg acaaagaaaa cttcaccgta ttgcaaacta ttcgtcagca    240
gcagtctgcc ctgaatgcaa cctgggtgga gctgttgcaa acgcgtaata ccctgaatcg    300
cgcgggtatc cgctggatga tggaccagag caatattggc agcggcgcaa ctgtcgctga    360
actgatgcag ggggcgacca atacgctgaa gctgaccgaa aaaaactggg agcagtatga    420
ggcgttaccg cgcgatccac gtcagagtga agcggctttc cttgagatca acgaaccta    480
tgatatctac cacggcgcgt tggcggagct tattcagctt cttggcgcgg gtaagattaa    540
cgagtttttt gatcaaccga ctcaaagcta tcaggacgct tttgagaagc agtcatggc    600
ctatatgcag caaaacgatc gtctgtacga tattgctgtt gaggataaca acagttccta    660
caaccaggcg atgtgggtac tggtcagtgt gctgattgcc gttctggtgg tcattatcgc    720
cgtctggttc ggcatcaaac tgtcgcttat cgccccgatg aatcgtctga ttgaaagcat    780
tcgtcatatc gccagcggcg atctggtgaa gcgtatcgac gtggaaggct ccaacgaaat    840
```

```
ggggcagttg gctgaaaacc tgcgtcatat gcaaagtgaa ctgatgcgta ccgtgggcga      900
tgtacgtaac ggcgcgaatg cgatctatag cggcgccagc gagattgcga tgggcaacaa      960
cgatctctct tcccgtactg agcagcaggc agcgtctctg aagagaccg ccgccagtat      1020
ggaacaactg accgccaccg tgaaacagaa cgccgaaaac gcccgtcagg ccagtcacct      1080
ggcgctgagt gcgtcagaga cagcgcaaaa aggcggcaaa gtggtggata acgtcgtaca      1140
aacaatgcgc gatatcgcct ccagttcgca gaaaatcgcc gatattatca gcgtaatcga      1200
cggtattgct ttccagacca atattctggc gctgaatgcg gcggtagaag cggcgcgcgc      1260
aggcgagcag ggacgcgggt tcgcagtggt ggccggtgaa gtccgtaatc tggcccagcg      1320
tagcgcgcag gcggcacggg agatcaagag tctgattgag gattccgtga gccgtgttga      1380
tgtaggttcg acgctggtcg aaagcgccgg tgaaaccatg gatgagatcg tcaatgcagt      1440
gacccgcgtg accgatatca tgggcgagat tgcctcggcg tctgacgagc aaagccgtgg      1500
tatcgaccag gtgggcctgg cggtagcgga gatggatcgc gtaacgcagc agaacgcctc      1560
gctggtggaa gagtccgccg ccgcggctgc ggcgctggaa gagcaagcca gccgtctgac      1620
ccaggccgtc gcggtgttcc gtattccacca gcaacagcag cgtgcgcgtg aagtggctgc      1680
ggtaaaaacc ccggcagccg tgtcgtcacc aaaggccgca gtggccgacg gcagcgataa      1740
ttgggaaaca tttaa                                                       1756
```

<210> SEQ ID NO 5
<211> LENGTH: 6177
<212> TYPE: DNA
<213> ORGANISM: Artificial Sequence
<220> FEATURE:
<223> OTHER INFORMATION: Synthetic- plasmid pK4947: suicide vector for
      construction of tsr deletion-insertion mutation

<400> SEQUENCE: 5

```
gatcctttt aacccatcac atatacctgc cgttcactat tatttagtga aatgagatat       60
tatgatattt tctgaattgt gattaaaaag gcaactttat gcccatgcaa cagaaactat      120
aaaaaataca gagaatgaaa agaaacagat agatttttta gttctttagg cccgtagtct      180
gcaaatcctt ttatgatttt ctatcaaaca aaagaggaaa atagaccagt tgcaatccaa      240
acgagagtct aatagaatga ggtcgaaaag taaatcgcgc gggtttgtta ctgataaagc      300
aggcaagacc taaaatgtgt aaagggcaaa gtgtatactt tggcgtcacc ccttacatat      360
tttaggtctt tttttattgt gcgtaactaa cttgccatct tcaaacagga gggctggaag      420
aagcagaccg ctaacacagt acataaaaaa ggagacatga acgatgaaca tcaaaaagtt      480
tgcaaaacaa gcaacagtat taacctttac taccgcactg ctggcaggag cgcaactcaa      540
agcgtttgcg aaagaaacga accaaaagcc atataaggaa acatacggca tttcccatat      600
tacacgccat gatatgctgc aaatccctga acagcaaaaa aatgaaaaat atcaagttcc      660
tgagttcgat tcgtccacaa ttaaaaatat ctcttctgca aaaggcctgg acgtttggga      720
cagctggcca ttacaaaacg ctgacggcac tgtcgcaaac tatcacggct accacatcgt      780
ctttgcatta gccggagatc ctaaaaatgc ggatgacaca tcgatttaca tgttctatca      840
aaaagtcggc gaaacttcta ttgacagctg aaaaacgct ggccgcgtct ttaaagacag      900
cgacaaattc gatgcaaatg attctatcct aaaagaccaa acacaagaat ggtcaggttc      960
agccacattt acatctgacg gaaaaatccg tttattctac actgatttct ccggtaaaca      1020
ttacggcaaa caaacactga caactgcaca agttaacgta tcagcatcag acagctcttt      1080
```

-continued

```
gaacatcaac ggtgtagagg attataaatc aatctttgac ggtgacggaa aaacgtatca    1140
aaatgtacag cagttcatcg atgaaggcaa ctacagctca ggcgacaacc atacgctgag    1200
agatcctcac tacgtagaag ataaaggcca caaatactta gtatttgaag caaacactgg    1260
aactgaagat ggctaccaag gcgaagaatc tttatttaac aaagcatact atggcaaaag    1320
cacatcattc ttccgtcaag aaagtcaaaa acttctgcaa agcgataaaa acgcacggc    1380 tgagttagca acggcgctc tcggtatgat tgagctaaac gatgattaca cactgaaaaa    1440
agtgatgaaa ccgctgattg catctaacac agtaacagat gaaattgaac gcgcgaacgt    1500
ctttaaaatg aacggcaaat ggtatctgtt cactgactcc cgcggatcaa aaatgacgat    1560
tgacggcatt acgtctaacg atatttacat gcttggttat gtttctaatt ctttaactgg    1620
cccatacaag ccgctgaaca aaactggcct tgtgttaaaa atggatcttg atcctaacga    1680
tgtaaccttt acttactcac acttcgctgt acctcaagcg aaaggaaaca atgtcgtgat    1740
tacaagctat atgacaaaca gaggattcta cgcagacaaa caatcaacgt ttgcgcccag    1800
cttcctgctg aacatcaaag gcaagaaaac atctgttgtc aaagacagca tccttgaaca    1860
aggacaatta acagttaaca aataaaaacg caaaagaaaa tgccgatatc ctattggcat    1920 tttctttat ttcttatcaa cataaaggtg aatcccatat gaactatata aaagcaggca    1980
aatggctaac cgtattccta accttttgaa ttcgatcgct agtttgtttt gactccatcc    2040
attagggctt ctaaaacgcc ttctaaggcc atgtcagccg ttaagtgttc ctgtgtcact    2100
gaaaattgct ttgagaggct ctaagggctt ctcagtgcgt tacatccctg gcttgttgtc    2160
cacaaccgtt aaaccttaaa agctttaaaa gccttatata ttcttttttt tcttataaaa    2220
cttaaaacct tagaggctat ttaagttgct gatttatatt aattttattg ttcaaacatg    2280
agagcttagt acgtgaaaca tgagagctta gtacgttagc catgagagct tagtacgtta    2340
gccatgaggg tttagttcgt taaacatgag agcttagtac gttaaacatg agagcttagt    2400
acgtgaaaca tgagagctta gtacgtacta tcaacaggtt gaactgctgg atcgatcctt    2460
tttgtccggt gttgggttga aggtgaagcc ggtcggggcc gcagcggggg ccggcttttc    2520
agccttgccc ccctgcttcg gccgccgtgg ctccggcgtc ttgggtgccg gcgcgggttc    2580
cgcagccttg gcctgcggtg cgggcacatc ggcgggcttg gccttgatgt gccgcctggc    2640
gtgcgagcgg aacgtctcgt aggagaactt gaccttcccc gtttcccgca tgtgctccca    2700
aatggtgacg agcgcatagc cggacgctaa cgccgcctcg acatccgccc tcaccgccag    2760
gaacgcaacc gcagcctcat cacgccggcg cttcttggcc gcgcgggatt caacccactc    2820
ggccagctcg tcggtgtagc tctttggcat cgtctctcgc ctgtcccctc agttcagtaa    2880
tttcctgcat ttgcctgttt ccagtcgtca gatattccac aaaacagcag ggaagcagcg    2940
cttttccgct gcataaccct gcttcggggt cattatagcg attttttcgg tatatccatc    3000 cttttcgca cgatatacag gattttgcca aagggttcgt gtagactttc cttggtgtat    3060
ccaacggcgt cagccgggca ggataggtga agtaggccca cccgcgagcg ggtgttcctt    3120
cttcactgtc ccttattcgc acctggcggt gctcaacggg aatcctgctc tgcgaggctg    3180
gccggctacc gccggcgtaa cagatgaggg caagcggatg gctgatgaaa ccaagccaac    3240
caggaagggc agcccaccta tcaaggtgta ctgccttcca gacgaacgaa gagcgattga    3300
ggaaaaggcg gcggcggccg gcatgagcct gtcggcctac ctgctggccg tcggccaggg    3360
ctacaaaatc acgggcgtcg tggactatga gcacgtccgc gagctggccc gcatcaatgg    3420
```

```
cgacctgggc cgcctgggcg gcctgctgaa actctggctc accgacgacc cgcgcacggc    3480
gcggttcggt gatgccacga tcctcgccct gctggcgaag atcgaagaga agcaggacga    3540
gcttggcaag gtcatgatgg gcgtggtccg cccgagggca gagccatgac tttttttagcc   3600
gctaaaacgg ccgggggtg cgcgtgattg ccaagcacgt ccccatgcgc tccatcaaga     3660
agagcgactt cgcggagctg gtgaagtaca tcaccgacga gcaaggcaag accgagcgcc    3720
tgggtcacgt gcgcgtcacg aactgcgagg caaacaccct gccgctgtc atggccgagg     3780
tgatggcgac ccagcacggc aacacccgtt ccgaggccga caagacctat cacctgctgg    3840
ttagcttccg cgcgggagag aagcccgacg cggagacgtt gcgcgcgatt gaggaccgca    3900
tctgcgctgg gcttggcttc gccgagcatc agcgcgtcag tgccgtgcat cacgacaccg    3960
acaacctgca catccatatc gccatcaaca agattcaccc gacccgaaac accatccatg    4020
agccgtatcg ggcctaccgc gccctcgctg acctctgcgc gacgctcgaa cgggactacg    4080
ggcttgagcg tgacaatcac gaaacgcggc agcgcgtttc cgagaaccgc gcgaacgaca    4140
tggagcggca cgcgggcgtg aaaagcctgg tcggctggat cgggccctaa atacctgtga    4200
cggaagatca cttcgcagaa taaataaatc ctggtgtccc tgttgatacc gggaagccct    4260
gggccaactt ttggcgaaaa tgagacgttg atcggcacgt aagaggttcc aactttcacc    4320
ataatgaaat aagatcacta ccgggcgtat ttttgagtt atcgagattt tcaggagcta    4380
aggaagctaa aatggagaaa aaatcactg gatataccac cgttgatata tcccaatggc    4440
atcgtaaaga acattttgag gcatttcagt cagttgctca atgtacctat aaccagaccg    4500
ttcagctgga tattacggcc ttttaaaga ccgtaaagaa aaataagcac aagttttatc     4560
cggcctttat tcacattctt gcccgcctga tgaatgctca tccggaattc cgtatggcaa    4620
tgaaagacgt tgagctggtg atatgggata gtgttcaccc ttgttacacc gttttccatg    4680
agcaaactga aacgttttca tcgctctgga gtgaatacca cgacgatttc cggcagtttc    4740
tacacatata ttcgcaagat gtggcgtgtt acggtgaaaa cctggcctat ttccctaaag    4800
ggtttattga gaatatgttt ttcgtctcag ccaatccctg ggtgagtttc accagttttg    4860
atttaaacgt ggccaatatg gacaacttct tcgcccccgt tttcaccatg gcaaatatt     4920
atacgcaagg cgacaaggtg ctgatgccgc tggcgattca ggttcatcat gccgtctgtg    4980
atggcttcca tgtcggcaga atgcttaatg aattacaaca gtactgcgat gagtggcagg    5040
gcggggcgta atttttttaa ggcagttatt ggtgccctta aacgcctggt gctacgcctg    5100
aataagtgat agggcccgat cccaagcttc ttctagaggt accgacttgt cgttattgat    5160
aaccgccggc gtcgcgcgcg tcgggtcgag tttcatgacc ttctgggcga tgtacaggct    5220
gtagtagcgg taagccacca gatagacgga aacggaagcg accacgatcc acagggcgct    5280
cacgtgttca ccccgacgta gggcaacgac cgagaggcag aaagcaccga tgattccgag    5340
aatcacccag ggtatgtgct tgaatatctt tttcgtatcc atagtaaaac ctggttgtaa    5400
gtttaattat cagccgaagc tgggtggaca ttgagttcgt gtttgaggag gtagattgac    5460
tgctatgctg agaggatctt gccagatcat cgcgcgcgta aagttaggta aatcagtgag    5520
tggttgtatg gcggtttaag cggtcggacg taccggtaag cggtttcgcg gaggagggcg    5580
tgggctattt tatgtgatat tctgaaatga gctgttgaca attaatcatc cggctcgtat    5640
aatgtgtaga tgcgtaggca cctgttacga cgaaccacac aggaaacaga ccatgttaaa    5700
gcgaattaaa attgttacca gcttactgct ggtattggcg ctatttggcc ttttacaact    5760
gacatccggc gggctgttct tcaactcgct gaagaatgac aaagaaaact tcaccgtatt    5820
```

```
gcaaactatt cgtcagcagc agtctgccct gaatgcaacc tgggtggagc tgttgcaaac    5880
gcgtaatacc ctgaatcgcg cgggtatccg ctggatgatg accagagca atattggcag    5940 cggcgcaact gtcgctgaac tgatgcaggg ggcgaccaat acgctgaagc tgaccgaaaa    6000
aaactgggag cagtatgagg cgttaccgcg cgatccacgt cagagtgaag cggctttcct    6060
tgagatcaaa cgaacctatg atatctacca cggcgcgttg gcggagctta ttcagcttct    6120
tggcgcgggt aagattaacg agttgtcgca tgcgatatcg agctctcccg ggaattc      6177
```

<210> SEQ ID NO 6
<211> LENGTH: 6176
<212> TYPE: DNA
<213> ORGANISM: Artificial Sequence
<220> FEATURE:
<223> OTHER INFORMATION: Synthetic- plasmid pK4948: suicide vector for construction of trg deletion mutation

<400> SEQUENCE: 6

```
gatcctttt aacccatcac atatacctgc cgttcactat tatttagtga atgagatat      60 tatgatattt tctgaattgt gattaaaaag gcaactttat gcccatgcaa cagaaactat    120
aaaaaataca gagaatgaaa agaaacagat agatttttta gttctttagg cccgtagtct    180
gcaaatcctt ttatgatttt ctatcaaaca aagaggaaa atagaccagt tgcaatccaa     240
acgagagtct aatagaatga ggtcgaaaag taaatcgcgc gggtttgtta ctgataaagc    300
aggcaagacc taaaatgtgt aaagggcaaa gtgtatactt tggcgtcacc ccttacatat    360
tttaggtctt tttttattgt gcgtaactaa cttgccatct tcaaacagga gggctggaag    420
aagcagaccg ctaacacagt acataaaaaa ggagacatga acgatgaaca tcaaaaagtt    480
tgcaaaacaa gcaacagtat taaccttac taccgcactg ctggcaggag gcgcaactca     540
agcgtttgcg aaagaaacga accaaaagcc atataaggaa acatacggca tttcccatat    600
tacacgccat gatatgctgc aaatccctga acagcaaaaa aatgaaaaat atcaagttcc    660
tgagttcgat tcgtccacaa ttaaaaatat ctcttctgca aaaggcctgg acgtttggga    720
cagctggcca ttacaaaacg ctgacggcac tgtcgcaaac tatcacggct accacatcgt    780
ctttgcatta gccggagatc ctaaaaatgc ggatgacaca tcgatttaca tgttctatca    840
aaaagtcggc gaaacttcta ttgacagctg gaaaaacgct ggccgcgtct ttaaagacag    900
cgacaaattc gatgcaaatg attctatcct aaaagaccaa acacaagaat ggtcaggttc    960
agccacattt acatctgacg gaaaaatccg tttattctac actgatttct ccggtaaaca    1020
ttacggcaaa caaacactga caactgcaca gttaacgta tcagcatcag acagctcttt     1080
gaacatcaac ggtgtagagg attataaatc aatctttgac ggtgacggaa aaacgtatca    1140
aaatgtacag cagttcatcg atgaaggcaa ctacagctca ggcgacaacc atacgctgag    1200
agatcctcac tacgtagaag ataaaggcca caaatactta gtatttgaag caaacactgg    1260
aactgaagat ggctaccaag gcgaagaatc tttattaac aaagcatact atggcaaaag     1320
cacatcattc ttccgtcaag aaagtcaaaa acttctgcaa agcgataaaa aacgcacggc    1380
tgagttagca acggcgctc tcggtatgat tgagctaaac gatgattaca cactgaaaaa     1440
agtgatgaaa ccgctgattg catctaacac agtaacagat gaaattgaac gcgcgaacgt    1500
ctttaaaatg aacggcaaat ggtatctgtt cactgactcc gcggatcaa aaatgacgat      1560 tgacggcatt acgtctaacg atatttcat gcttggttat gttctaatt ctttaactgg       1620 cccatacaag ccgctgaaca aaactggcct tgtgttaaaa atggatcttg atcctaacga    1680
```

```
tgtaaccttt acttactcac acttcgctgt acctcaagcg aaaggaaaca atgtcgtgat    1740
tacaagctat atgacaaaca gaggattcta cgcagacaaa caatcaacgt ttgcgcccag    1800
cttcctgctg aacatcaaag gcaagaaaac atctgttgtc aaagacagca tccttgaaca    1860
aggacaatta acagttaaca aataaaaacg caaaagaaaa tgccgatatc ctattggcat    1920
tttcttttat ttcttatcaa cataaaggtg aatcccatat gaactatata aaagcaggca    1980
aatggctaac cgtattccta accttttgaa ttcgatcgct agtttgtttt gactccatcc    2040
attagggctt ctaaaacgcc ttctaaggcc atgtcagccg ttaagtgttc ctgtgtcact    2100
gaaaattgct ttgagaggct ctaagggctt ctcagtgcgt tacatccctg gcttgttgtc    2160
cacaaccgtt aaaccttaaa agctttaaaa gccttatata ttcttttttt tcttataaaa    2220
cttaaaacct tagaggctat ttaagttgct gatttatatt aattttattg ttcaaacatg    2280
agagcttagt acgtgaaaca tgagagctta gtacgttagc catgagagct tagtacgtta    2340
gccatgaggg tttagttcgt taaacatgag agcttagtac gttaaacatg agagcttagt    2400
acgtgaaaca tgagagctta gtacgtacta tcaacaggtt gaactgctgg atcgatcctt    2460
tttgtccggt gttgggttga aggtgaagcc ggtcggggcc gcagcggggg ccggcttttc    2520
agccttgccc ccctgcttcg gccgccgtgg ctccggcgtc ttgggtgccg gcgcgggttc    2580
cgcagccttg gcctgcggtg cgggcacatc ggcgggcttg gccttgatgt gccgcctggc    2640
gtgcgagcgg aacgtctcgt aggagaactt gaccttcccc gtttcccgca tgtgctccca    2700
aatggtgacg agcgcatagc cggacgctaa cgccgcctcg acatccgccc tcaccgccag    2760
gaacgcaacc gcagcctcat cacgccggcg cttcttggcc gcgcgggatt caacccactc    2820
ggccagctcg tcggtgtagc tctttggcat cgtctctcgc ctgtcccctc agttcagtaa    2880
tttcctgcat ttgcctgttt ccagtcggta gatattccac aaaacagcag ggaagcagcg    2940
cttttccgct gcataaccct gcttcggggt cattatagcg attttttcgg tatatccatc    3000 cttttttcgca cgatatacag gattttgcca aagggttcgt gtagactttc cttggtgtat    3060
ccaacggcgt cagccgggca ggataggtga agtaggccca cccgcgagcg ggtgttcctt    3120
cttcactgtc ccttattcgc acctggcggt gctcaacggg aatcctgctc tgcgaggctg    3180
gccggctacc gccggcgtaa cagatgaggg caagcggatg gctgatgaaa ccaagccaac    3240
caggaagggc agcccaccta tcaaggtgta ctgccttcca gacgaacgaa gagcgattga    3300
ggaaaaggcg gcggcggccg gcatgagcct gtcggcctac ctgctggccg tcggccaggg    3360
ctacaaaatc acgggcgtcg tggactatga gcacgtccgc gagctggccc gcatcaatgg    3420
cgacctgggc cgcctgggcg gcctgctgaa actctggctc accgacgacc gcgcacggc    3480 gcggttcggt gatgccacga tcctcgccct gctggcgaag atcgaagaga agcaggacga    3540
gcttggcaag gtcatgatgg gcgtggtccg cccgagggca gagccatgac ttttttagcc    3600
gctaaaacgg ccgggggtg cgcgtgattg ccaagcacgt ccccatgcgc tccatcaaga    3660
agagcgactt cgcggagctg gtgaagtaca tcaccgacga gcaaggcaag accgagcgcc    3720
tgggtcacgt gcgcgtcacg aactgcgagg caaacaccct gcccgctgtc atggccgagg    3780
tgatggcgac ccagcacggc aacacccgtt ccgaggccga caagacctat cacctgctgg    3840
ttagcttccg cgcgggagag aagcccgacg cggagacgtt gcgcgcgatt gaggaccgca    3900
tctgcgctgg gcttggcttc gccgagcatc agcgcgtcag tgccgtgcat cacgacaccg    3960
acaacctgca catccatatc gccatcaaca agattcaccc gacccgaaac accatccatg    4020
```

```
agccgtatcg ggcctaccgc gccctcgctg acctctgcgc gacgctcgaa cgggactacg    4080
ggcttgagcg tgacaatcac gaaacgcggc agcgcgtttc cgagaaccgc gcgaacgaca    4140
tggagcggca cgcgggcgtg gaaagcctgg tcggctggat cgggccctaa atacctgtga    4200
cggaagatca cttcgcagaa taaataaatc ctggtgtccc tgttgatacc gggaagccct    4260
gggccaactt ttggcgaaaa tgagacgttg atcggcacgt aagaggttcc aactttcacc    4320
ataatgaaat aagatcacta ccgggcgtat ttttgagtt atcgagattt tcaggagcta    4380
aggaagctaa aatggagaaa aaaatcactg gatataccac cgttgatata tcccaatggc    4440
atcgtaaaga acattttgag gcatttcagt cagttgctca atgtacctat aaccagaccg    4500
ttcagctgga tattacggcc tttttaaaga ccgtaaagaa aaataagcac aagttttatc    4560
cggcctttat tcacattctt gcccgcctga tgaatgctca tccggaattc cgtatggcaa    4620
tgaaagacgg tgagctggtg atatgggata gtgttcaccc ttgttacacc gttttccatg    4680
agcaaactga aacgttttca tcgctctgga gtgaatacca cgacgatttc cggcagtttc    4740
tacacatata ttcgcaagat gtggcgtgtt acggtgaaaa cctggcctat ttccctaaag    4800
ggtttattga gaatatgttt ttcgtctcag ccaatccctg ggtgagtttc accagttttg    4860
atttaaacgt ggccaatatg gacaacttct tcgcccccgt tttcaccatg gcaaatatt    4920
atacgcaagg cgacaaggtg ctgatgccgc tggcgattca ggttcatcat gccgtctgtg    4980
atggcttcca tgtcggcaga atgcttaatg aattacaaca gtactgcgat gagtggcagg    5040
gcggggcgta atttttttaa ggcagttatt ggtgccctta aacgcctggt gctacgcctg    5100
aataagtgat agggcccgat cccaagcttc ttctagaggt accgacttga cgttattgtt    5160
gagcttactg atggcggcgt agatttcagt tttgaatgta tcggcaacgt taacgtgatg    5220
cgagcagcgc tggaatgttg tcataaaggc tggggcgaaa gcattattat tggcgtagcg    5280
ggggcagggc aggaaatcaa aacccgtccc ttccagctag tgaccggtcg cgtctggcgt    5340
ggctccgcct ttggcggcgt gaaagggcgc acgcagctgc cagggatggt cgaagatgcg    5400
atgaacggta aaatccgttt agatcctttt attactcacc gcctgccgct ggagcagatt    5460
aacgatgcct ttgaactgat gcatcagggt aaatccatcc gtactgttat ccactttggc    5520
gataactgat tcatccgcca gcggattttc cgctggcgct tttctgaatt ttctggaatg    5580
aatgttgtga aaatgtgatt ctgaaatgag ctgttgacaa ttaatcatcc ggctcgtata    5640
atgtgtagat gcgtaggcac ctgttacgac gaaccacaca ggaaacagac ctaagcgtcg    5700
cgccagcggg ctatttttagc cgcgggcgcg tttattctcc gacagccgct atcacagcgg    5760
catcgattta cggatcgccg caatcagcat ttgcgccccg gttgagagcg ggatatcaac    5820
tcgcgtaaga atacctatcg gctcgcccgc gctctgggtc ggcacgggta atgagaccag    5880
cgtcgcctgg cgaagatctt ctttaaccgc gccagagggg acgaaccaga cgtaatcgta    5940
atctacggtc agttgtcgtg ataacgatgc ggatagcgtt tcgatacatc cggcaggcat    6000
tttacacccc tggctttgca acagggcttc cgcattctgg cgcggtaccg tgccttttgg    6060
cgagacgact accggccatt ccataacccg gctgagcgtg atcgtctcct gtaacagggg    6120
atgaccgggg cgtaccacta attgtcgcat gcgatatcga gctctcccgg gaattc        6176
```

<210> SEQ ID NO 7
<211> LENGTH: 6648
<212> TYPE: DNA
<213> ORGANISM: Artificial Sequence
<220> FEATURE:
<223> OTHER INFORMATION: Synthetic- plasmid pK5079: lysis vector expressing human TRAIL

<400> SEQUENCE: 7

```
agatctagcc cgcctaatga gcgggctttt ttttaattcg caattccccg atgcataatg      60
tgcctgtcaa atggacgaag cagggattct gcaaaccta tgctactccg tcaagccgtc     120
aattgtctga ttcgttacca attatgacaa cttgacggct acatcattca cttttcttc     180
acaaccggca cggaactcgc tcgggctggc cccggtgcat tttttaaata cccgcgagaa     240
atagagttga tcgtcaaaac caacattgcg accgacggtg gcgataggca tccgggtggt     300
gctcaaaagc agcttcgcct ggctgatacg ttggtcctcg cgccagctta agacgctaat     360
ccctaactgc tggcggaaaa gatgtgacag acgcgacggc gacaagcaaa catgctgtgc     420
gacgctggcg atatcaaaat tgctgtctgc caggtgatcg ctgatgtact gacaagcctc     480
gcgtacccga ttatccatcg gtggatggag cgactcgtta atcgcttcca tgcgccgcag     540
taacaattgc tcaagcagat ttatcgccag cagctccgaa tagcgccctt ccccttgccc     600
ggcgttaatg atttgcccaa acaggtcgct gaaatgcggc tggtgcgctt catccgggcg     660
aaagaacccc gtattggcaa atattgacgg ccagttaagc cattcatgcc agtaggcgcg     720
cggacgaaag taaacccact ggtgatacca ttcgcgagcc tccggatgac gaccgtagtg     780
atgaatctct cctggcggga acagcaaaat atcacccggt cggcaaacaa attctcgtcc     840
ctgattttc accacccct gaccgcgaat ggtgagattg agaatataac ctttcattcc     900
cagcggtcgg tcgataaaaa aatcgagata accgttggcc tcaatcggcg ttaaacccgc     960
caccagatgg gcattaaacg agtatcccgg cagcagggga tcattttgcg cttcagccat    1020
actttcata ctcccgccat tcagagaaga aaccaattgt ccatattgca tcagacattg    1080
ccgtcactgc gtcttttact ggctcttctc gctaaccaaa ccgtaaccc cgcttattaa    1140
aagcattctg taacaaagcg ggaccaaagc catgacaaaa acgcgtaaca aaagtgtcta    1200
taatcacggc agaaaagtcc acattgatta tttgcacggc gtcacacttt gctatgccat    1260
agcatttta tccataagat tagcggatcc tacctgacgc ttttatcgc aactctctac    1320
tgtttctcca tacccgtttt tttgggctag cgaattctga gaacaaacta atgggataaa    1380
tttcgtgttc agggggccaac gaagctccag ggcgaagtca caattttccgg cgctaaaaat    1440
gctgctctgc ctatcctttt tgccgcacta ctggcggaag aaccggtaga gatccagaac    1500
gtcccgaaac tgaaagacgt cgatacatca atgaagctgc taagccagct gggtgcgaaa    1560
gtagaacgta atggttctgt gcatattgat gcccgcgacg ttaatgtatt ctgcgcacct    1620
tacgatctgg ttaaaaccat gcgtgcttct atctgggcgc tggggccgct ggtagcgcgc    1680
tttggtcagg gcaagtttc actacctggc ggttgtacga tcggtgcgcg tccggttgat    1740
ctacacattt ctggcctcga acaattaggc gcgaccatca aactggaaga aggttacgtt    1800
aaagcttccg tcgatggtcg tttgaaaggt gcacatatcg tgatggataa agtcagcgtt    1860
ggcgcaacgg tgaccatcat gtgtgctgca accctggcgg aaggcaccac gattattgaa    1920
aacgcagcgc gtgaaccgga atcgtcgat accgcgaact tcctgattac gctgggtgcg    1980
aaaattagcg gtcagggcac cgatcgtatc gtcatcgaag gtgtggaacg tttaggcggc    2040
ggtgtctatc gcgttctgcc ggatcgtatc gaaaccggta ctttcctggt ggcggcggcg    2100
attctctcgcg gcaaaattat ctgccgtaac gcgcagccag atactctcga cgccgtgctg    2160
gcgaaactgc gtgacgctgg agcggacatc gaagtcggcg aagactggat tagcctggat    2220
atgcatggca aacgtccgaa ggctgttaac gtacgtaccg cgccgcatcc ggcattcccg    2280
```

```
accgatatgc aggcccagtt cacgctgttg aacctggtgg cagaagggac cgggtttatc   2340
accgaaacgg tctttgaaaa ccgctttatg catgtgccag agctgagccg tatgggcgcg   2400
cacgccgaaa tcgaaagcaa taccgttatt tgtcacggtg ttgaaaaact ttctggcgca   2460
caggttatgg caaccgatct gcgtgcatca gcaagcctgg tgctggctgg ctgtattgcg   2520
gaagggacga cggtggttga tcgtatttat cacatcgatc gtggctacga acgcattgaa   2580
gacaaactgc gcgctttagg tgcaaatatt gagcgtgtga aaggcgaata agaattcagg   2640
aaaaaaacgc tgtgaaaaat gttggttttta tcggctggcg cggaatggtc ggctctgttc   2700
tcatgcaacg catggtagag gagcgcgatt tcgacgctat tcgccctgtt ttcttttcta   2760
cctcccagtt tggacaggcg gcgcccacct tcggcgacac ctccaccggc acgctacagg   2820
acgcttttga tctggatgcg ctaaaagcgc tcgatatcat cgtgacctgc cagggcggcg   2880
attataccaa cgaaatttat ccaaagctgc gcgaaagcgg atggcagggt tactggattg   2940
atgcggcttc tacgctgcgc atgaaagatg atgccattat tattctcgac ccggtcaacc   3000
aggacgtgat taccgacggc ctgaacaatg gcgtgaagac cttttgtgggc ggtaactgta   3060 ccgttagcct gatgttgatg tcgctgggcg gtctcttttgc ccataatctc gttgactggg   3120
tatccgtcgc gacctatcag gccgcctccg gcggcggcgc gcgccatatg cgcgagctgt   3180
taacccagat gggtcagttg tatggccatg tcgccgatga actggcgacg ccgtcttccg   3240
caattcttga tattgaacgc aaagttacgg cattgacccg cagcggcgag ctgccggttg   3300
ataactttgg cgtaccgctg gcgggaagcc tgatcccctg gatcgacaaa cagctcgata   3360
acggccagag ccgcgaagag tggaaaggcc aggcggaaac caacaagatt ctcaatactg   3420
cctctgtgat tccggttgat ggtttgtgtg tgcgcgtcgg cgcgctgcgc tgtcacagcc   3480
aggcgttcac catcaagctg aaaaaagagg tatccattcc gacggtggaa gaactgctgg   3540
cggcacataa tccgtgggcg aaagtggtgc cgaacgatcg tgatatcact atgcgcgaat   3600 taacccccggc ggcggtgacc ggcacgttga ctacgccggt tggtcgtctg cgtaagctga   3660
acatggggcc agagttcttg tcggcgttta ccgtaggcga ccagttgtta tgggcgccg   3720 ccgagccgct gcgtcgaatg ctgcgccagt tggcgtagtc tagctgcacg ataccgtcga   3780
cttgtacata gactcgctcc gaaattaaag aacacttaaa ttatctacta aaggaatctt   3840
tagtcaagtt tatttaagat gacttaacta tgaatacaca attgatgggt gagcgtagga   3900
gcatgcttat gcgaaaggcc atcctgacgg atggccttttt tggatcttcc ggaagacctt   3960
ccattctgaa atgagctgtt gacaattaat catccggctc gtataatgtg tggaattgtg   4020
agcggataac aatttcacac aggaaacaga ccatggctat gatggaggtc cagggggggac   4080 ccagcctggg acagacctgc gtgctgatcg tgatcttcac agtgctcctg cagtctctct   4140
gtgtggctgt aacttacgtg tactttacca acgagctgaa gcagatgcag acaagtact   4200 ccaaaagtgg cattgcttgt ttcttaaaag aagatgacag ttattgggac cccaatgacg   4260
aagagagtat gaacagcccc tgctggcaag tcaagtggca actccgtcag ctcgttagaa   4320
agatgatttt gagaacctct gaggaaacca tttctacagt tcaagaaaag caacaaaata   4380 tttctccccct agtgagagaa agaggtcctc agagagtagc agctcacata actgggacca   4440
gaggaagaag caacacattg tcttctccaa actccaagaa tgaaaaggct ctgggccgca   4500
aaataaactc ctgggaatca tcaaggagtg ggcattcatt cctgagcaac ttgcacttga   4560
ggaatggtga actggtcatc catgaaaaag ggtttttacta catctattcc caaacatact   4620
```

-continued

```
ttcgatttca ggaggaaata aaagaaaaca caaagaacga caaacaaatg gtccaatata      4680
tttacaaata cacaagttat cctgacccta tattgttgat gaaaagtgct agaaatagtt      4740
gttggtctaa agatgcagaa tatggactct attccatcta tcaaggggga atatttgagc      4800
ttaaggaaaa tgacagaatt tttgtttctg taacaaatga gcacttgata gacatggacc      4860
atgaagccag ttttttcggg gccttttag ttggctgacc cggggatccg tcgacctgca      4920
gccaagctcc caagcttggc tgttttggcg gatgagagaa gattttcagc ctgatacaga      4980
ttaaatcaga acgcagaagc ggtctgataa aacagaattt gcctggcggc agtagcgcgg      5040
tggtcccacc tgaccccatg ccgaactcag aagtgaaacg ccgtagcgcc gatggtagtg      5100
tggggtctcc ccatgcgaga gtagggaact gccaggcatc aaataaaacg aaaggctcag      5160
tcgaaagact gggcctttcg ttttatctgt tgtttgtcgg tgaacgctct cctgagtagg      5220
acaaatccgc cgggagcgga tttgaacgtt gcgaagcaac ggcccggagg gtggcgggca      5280
ggacgcccgc cataaactgc caggcatcaa attaagcaga aggccatcct gacggatggc      5340 cttttttgcgt ttctacaaac tcttttgttt attttttctaa atacattcaa atatgtatcc      5400
gctcatgaga caataaccct gataaatgct tcaataatgg aagatcttcc aacatcacag      5460
gtaaacagaa acgtcgggtc gatcgggaaa ttctttcccg gacggcgcgg ggttgggcaa      5520
gccgcaggcg cgtcagtgct tttagcgggt gtcggggcgc agccatgacc cagtcacgta      5580
gcgatagcgg agtgtatact ggcttaacta tgcggcatca gagcagattg tactgagagt      5640
gcaccatatg cggtgtgaaa taccgcacag atgcgtaagg agaaaatacc gcatcaggcg      5700
ctcttccgct tcctcgctca ctgactcgct gcgctcggtc gttcggctgc ggcgagcggt      5760
atcagctcac tcaaaggcgg taatacggtt atccacagaa tcagggata acgcaggaaa      5820 gaacatgtga gcaaaaggcc agcaaaaggc caggaaccgt aaaaaggccg cgttgctggc      5880 gttttttccat aggctccgcc cccctgacga gcatcacaaa aatcgacgct caagtcagag      5940
gtggcgaaac ccgacaggac tataaagata ccaggcgttt ccccctggaa gctccctcgt      6000
gcgctctcct gttccgaccc tgccgcttac cggatacctg tccgcctttc tcccttcggg      6060
aagcgtggcg ctttctcata gctcacgctg taggtatctc agttcggtgt aggtcgttcg      6120
ctccaagctg ggctgtgtgc acgaaccccc cgttcagccc gaccgctgcg ccttatccgg      6180
taactatcgt cttgagtcca acccggtaag acacgactta tcgccactgg cagcagccac      6240
tggtaacagg attagcagag cgaggtatgt aggcggtgct acagagttct tgaagtggtg      6300
gcctaactac ggctacacta aggacagt atttggtatc tgcgctctgc tgaagccagt       6360
taccttcgga aaagagttg gtagctcttg atccggcaaa caaaccaccg ctggtagcgg       6420
tggttttttt gtttgcaagc agcagattac gcgcagaaaa aaggatctc aagaagatcc       6480 tttgatcttt tctacggggt ctgacgctca gtggaacgaa aactcacgtt aagggatttt      6540
ggtcatgaga ttatcaaaaa ggatcttcac ctagatcctt ttaaattaaa aatgaagttt      6600
taaatcaatc taaagtatat atgagtaaac ttggtctgac agtctaga                  6648
```

<210> SEQ ID NO 8
<211> LENGTH: 32
<212> TYPE: DNA
<213> ORGANISM: Artificial Sequence
<220> FEATURE:
<223> OTHER INFORMATION: Synthetic- C-Nco I TRAIL 3681 5' primer for construction of pK5079 plasmid

<400> SEQUENCE: 8

```
gacgtcccat ggctatgatg gaggtccagg gg                                32
```

<210> SEQ ID NO 9
<211> LENGTH: 33
<212> TYPE: DNA
<213> ORGANISM: Artificial Sequence
<220> FEATURE:
<223> OTHER INFORMATION: Synthetic- C-Xma I TRAIL 3681 3' primer for
      construction of pK5079 plasmid

<400> SEQUENCE: 9

```
ctgcagcccg ggctagccaa ctaaaaaggc ccc                               33
```

<210> SEQ ID NO 10
<211> LENGTH: 27
<212> TYPE: DNA
<213> ORGANISM: Artificial Sequence
<220> FEATURE:
<223> OTHER INFORMATION: Synthetic- tar/cheM Primer 1 for construction
      of pK4946 plasmid

<400> SEQUENCE: 10

```
catcgccaat acaccggcct ttataaa                                      27
```

<210> SEQ ID NO 11
<211> LENGTH: 75
<212> TYPE: DNA
<213> ORGANISM: Artificial Sequence
<220> FEATURE:
<223> OTHER INFORMATION: Synthetic- tar/cheM Primer 2 for construction
      of pK4946 plasmid

<400> SEQUENCE: 11

```
ctacacatta tacgagccgg atgattaatt gtcaacagct catttcagaa tcgcgggcga   60
tgaagaggca ctctc                                                   75
```

<210> SEQ ID NO 12
<211> LENGTH: 87
<212> TYPE: DNA
<213> ORGANISM: Artificial Sequence
<220> FEATURE:
<223> OTHER INFORMATION: Synthetic- tar/cheM Primer 3 for construction
      of pK4946 plasmid

<400> SEQUENCE: 12

```
ggctcgtata atgtgtagat gcgtaggcac ctgttacgac gaaccacaca ggaaacagac   60
catgtttaac cgtatccgcg ttgtcac                                      87
```

<210> SEQ ID NO 13
<211> LENGTH: 27
<212> TYPE: DNA
<213> ORGANISM: Artificial Sequence
<220> FEATURE:
<223> OTHER INFORMATION: Synthetic- tar/cheM Primer 4 for construction
      of pK4946 plasmid

<400> SEQUENCE: 13

```
gaagtaggca tccatattgc cattgtc                                      27
```

<210> SEQ ID NO 14
<211> LENGTH: 27
<212> TYPE: DNA
<213> ORGANISM: Artificial Sequence
<220> FEATURE:
<223> OTHER INFORMATION: Synthetic- tsr Primer 1 for construction of
      pK4947 plasmid -continued

<400> SEQUENCE: 14
gtcgttattg ataaccgccg gcgtcgc                                                27

<210> SEQ ID NO 15
<211> LENGTH: 77
<212> TYPE: DNA
<213> ORGANISM: Artificial Sequence
<220> FEATURE:
<223> OTHER INFORMATION: Synthetic- tsr Primer 2 for construction of
      pK4947 plasmid

<400> SEQUENCE: 15
ctacacatta tacgagccgg atgattaatt gtcaacagct catttcagaa tatcacataa           60
aatagcccac gccctcc                                                          77

<210> SEQ ID NO 16
<211> LENGTH: 88
<212> TYPE: DNA
<213> ORGANISM: Artificial Sequence
<220> FEATURE:
<223> OTHER INFORMATION: Synthetic- tsr Primer 3 for construction of
      pK4947 plasmid

<400> SEQUENCE: 16
ggctcgtata atgtgtagat gcgtaggcac ctgttacgac gaaccacaca ggaaacagac           60
catgttaaag cgaattaaaa ttgttacc                                              88

<210> SEQ ID NO 17
<211> LENGTH: 27
<212> TYPE: DNA
<213> ORGANISM: Artificial Sequence
<220> FEATURE:
<223> OTHER INFORMATION: Synthetic- tsr Primer 4 for construction of
      pK4947 plasmid

<400> SEQUENCE: 17
ctcgttaatc ttacccgcgc caagaag                                               27

<210> SEQ ID NO 18
<211> LENGTH: 27
<212> TYPE: DNA
<213> ORGANISM: Artificial Sequence
<220> FEATURE:
<223> OTHER INFORMATION: Synthetic- D-Trg Up 5' primer for construction
      of pK4948 plasmid

<400> SEQUENCE: 18
gacgttattg ttgagcttac tgatggc                                               27

<210> SEQ ID NO 19
<211> LENGTH: 38
<212> TYPE: DNA
<213> ORGANISM: Artificial Sequence
<220> FEATURE:
<223> OTHER INFORMATION: Synthetic- D-Trg Up 3' primer for construction
      of pK4948 plasmid

<400> SEQUENCE: 19
gctggcgcga cgcttacaca ttttcacaac attcattc                                   38

<210> SEQ ID NO 20
<211> LENGTH: 27
<212> TYPE: DNA
<213> ORGANISM: Artificial Sequence

```
<220> FEATURE:
<223> OTHER INFORMATION: Synthetic- D-Trg Down 5' primer for
      construction of pK4948 plasmid

<400> SEQUENCE: 20
taagcgtcgc gccagcgggc tatttta                                        27

<210> SEQ ID NO 21
<211> LENGTH: 27
<212> TYPE: DNA
<213> ORGANISM: Artificial Sequence
<220> FEATURE:
<223> OTHER INFORMATION: Synthetic- D-Trg Down 3' primer for
      construction of pK4948 plasmid

<400> SEQUENCE: 21
ttagtggtac gccccggtca tcccctg                                        27

<210> SEQ ID NO 22
<211> LENGTH: 22
<212> TYPE: DNA
<213> ORGANISM: Artificial Sequence
<220> FEATURE:
<223> OTHER INFORMATION: Synthetic- Tar plus Flag Primer 1 for
      construction of pK4949 plasmid

<400> SEQUENCE: 22
cgggagagca ggggcgcggt tt                                             22

<210> SEQ ID NO 23
<211> LENGTH: 42
<212> TYPE: DNA
<213> ORGANISM: Artificial Sequence
<220> FEATURE:
<223> OTHER INFORMATION: Synthetic- Tar plus Flag Primer 2 for
      construction of pK4949 plasmid

<400> SEQUENCE: 23
tcgtcatcgt ctttataatc gaaggtttcc cagttcgcat ca                       42

<210> SEQ ID NO 24
<211> LENGTH: 47
<212> TYPE: DNA
<213> ORGANISM: Artificial Sequence
<220> FEATURE:
<223> OTHER INFORMATION: Synthetic- Tar plus Flag Primer 3 for
      construction of pK4949 plasmid

<400> SEQUENCE: 24
gattataaag acgatgacga taagtgatcg acgtgcgctg tcggtta                  47

<210> SEQ ID NO 25
<211> LENGTH: 23
<212> TYPE: DNA
<213> ORGANISM: Artificial Sequence
<220> FEATURE:
<223> OTHER INFORMATION: Synthetic- Tsr plus c-Myc Primer 1 for
      construction of pK4950 plasmid

<400> SEQUENCE: 25
cgcgcgcagg cgagcaggga cgc                                            23

<210> SEQ ID NO 26
<211> LENGTH: 42
<212> TYPE: DNA
<213> ORGANISM: Artificial Sequence
<220> FEATURE:
```

<223> OTHER INFORMATION: Synthetic- Tsr plus c-Myc Primer 2 for
    construction of pK4950 plasmid

<400> SEQUENCE: 26
cttcggagat cagtttctgt tcaaatgttt cccaattatc gc         42

<210> SEQ ID NO 27
<211> LENGTH: 52
<212> TYPE: DNA
<213> ORGANISM: Artificial Sequence
<220> FEATURE:
<223> OTHER INFORMATION: Synthetic- Tsr plus c-Myc Primer 3 for
    construction of pK4950 plasmid

<400> SEQUENCE: 27
gaacagaaac tgatctccga agaggatctg taagggcgta gtggtgaaca gt         52

<210> SEQ ID NO 28
<211> LENGTH: 23
<212> TYPE: DNA
<213> ORGANISM: Artificial Sequence
<220> FEATURE:
<223> OTHER INFORMATION: Synthetic- Tsr plus c-Myc Primer 4 for
    construction of pK4950 plasmid

<400> SEQUENCE: 28
gattttgcag agcacgccct gcg         23

<210> SEQ ID NO 29
<211> LENGTH: 39
<212> TYPE: DNA
<213> ORGANISM: Artificial Sequence
<220> FEATURE:
<223> OTHER INFORMATION: Synthetic- sseL Primer 1 for construction of
    pK4951 plasmid

<400> SEQUENCE: 29
cccaagcttg ctgcggcatt gccggtacgt atggattta         39

<210> SEQ ID NO 30
<211> LENGTH: 49
<212> TYPE: DNA
<213> ORGANISM: Artificial Sequence
<220> FEATURE:
<223> OTHER INFORMATION: Synthetic- sseL Primer 2 for construction of
    pK4951 plasmid

<400> SEQUENCE: 30
gggataggct ctaagtactc accactcttc tgtatataag ctgtgaaat         49

<210> SEQ ID NO 31
<211> LENGTH: 48
<212> TYPE: DNA
<213> ORGANISM: Artificial Sequence
<220> FEATURE:
<223> OTHER INFORMATION: Synthetic- sseL Primer 3 for construction of
    pK4951 plasmid

<400> SEQUENCE: 31
tttcacagct tatatacaga agagtggtga gtacttagag cctatccc         48

<210> SEQ ID NO 32
<211> LENGTH: 33
<212> TYPE: DNA
<213> ORGANISM: Artificial Sequence
<220> FEATURE:
<223> OTHER INFORMATION: Synthetic- sseL Primer 4 for construction of pK4951 plasmid

<400> SEQUENCE: 32
cgggaattcg gggagaatcg acaactatat ggc                               33

<210> SEQ ID NO 33
<211> LENGTH: 33
<212> TYPE: DNA
<213> ORGANISM: Artificial Sequence
<220> FEATURE:
<223> OTHER INFORMATION: Synthetic- spvD Primer 1 for construction of
      pK4952 plasmid

<400> SEQUENCE: 33
cccaagcttc tcagggcaaa tttgccggtg aca                               33

<210> SEQ ID NO 34
<211> LENGTH: 48
<212> TYPE: DNA
<213> ORGANISM: Artificial Sequence
<220> FEATURE:
<223> OTHER INFORMATION: Synthetic- spvD Primer 2 for construction of
      pK4952 plasmid

<400> SEQUENCE: 34
taaaatgaat atttaaaaaa gttaagttac actacctcaa taaaatgc               48

<210> SEQ ID NO 35
<211> LENGTH: 48
<212> TYPE: DNA
<213> ORGANISM: Artificial Sequence
<220> FEATURE:
<223> OTHER INFORMATION: Synthetic- spvD Primer 3 for construction of
      pK4952 plasmid

<400> SEQUENCE: 35 gcatttatt gaggtagtgt aacttaactt ttttaaatat tcatttta                48

<210> SEQ ID NO 36
<211> LENGTH: 33
<212> TYPE: DNA
<213> ORGANISM: Artificial Sequence
<220> FEATURE:
<223> OTHER INFORMATION: Synthetic- spvD Primer 4 for construction of
      pK4952 plasmid

<400> SEQUENCE: 36
cccaagcttg ctgtacacaa aacggactgc acc                               33

<210> SEQ ID NO 37
<211> LENGTH: 33
<212> TYPE: DNA
<213> ORGANISM: Artificial Sequence
<220> FEATURE:
<223> OTHER INFORMATION: Synthetic- ssrAB Primer 1 for construction of
      pK4953 plasmid

<400> SEQUENCE: 37
cgggaattcg ctactacttg tggtataata acc                               33

<210> SEQ ID NO 38
<211> LENGTH: 48
<212> TYPE: DNA
<213> ORGANISM: Artificial Sequence
<220> FEATURE:
<223> OTHER INFORMATION: Synthetic- ssrAB Primer 2 for construction of
      pK4953 plasmid

```
<400> SEQUENCE: 38
cttaatacca tcggacgccc ctggaatgct tccctccagt tgcctgtt          48

<210> SEQ ID NO 39
<211> LENGTH: 48
<212> TYPE: DNA
<213> ORGANISM: Artificial Sequence
<220> FEATURE:
<223> OTHER INFORMATION: Synthetic- ssrAB Primer 3 for construction of
      pK4953 plasmid

<400> SEQUENCE: 39
aacaggcaac tggagggaag cattccaggg gcgtccgatg gtattaag          48

<210> SEQ ID NO 40
<211> LENGTH: 33
<212> TYPE: DNA
<213> ORGANISM: Artificial Sequence
<220> FEATURE:
<223> OTHER INFORMATION: Synthetic- ssrAB Primer 4 for construction of
      pK4953 plasmid

<400> SEQUENCE: 40
cgggaattct gatccgagag attccatccg cta                          33

<210> SEQ ID NO 41
<211> LENGTH: 6645
<212> TYPE: DNA
<213> ORGANISM: Artificial Sequence
<220> FEATURE:
<223> OTHER INFORMATION: Synthetic- plasmid pK4951: suicide vector for
      construction of sseL deletion mutation

<400> SEQUENCE: 41
cgcgtttccg agaaccgcgc gaacgacatg gagcggcacg cgggcgtgga aagcctggtc    60
ggctggatcg gcacgatgcg tccggcgtag aggatctgaa gatccagcag ttcaacctgt   120
tgatagtacg tactaagctc tcatgtttca cgtactaagc tctcatgttt aacgtactaa   180
gctctcatgt ttaacgaact aaaccctcat ggctaacgta ctaagctctc atggctaacg   240
tactaagctc tcatgtttca cgtactaagc tctcatgttt gaacaataaa attaatataa   300
atcagcaact aaatagcct ctaaggtttt aagttttata agaaaaaaaa gaatatataa    360
ggcttttaaa gcttttaagg tttaacggtt gtggacaaca agccagggat gtaacgcact   420
gagaagccct tagagcctct caaagcaatt ttcagtgaca caggaacact taacggctga   480
catgggaatt ctgatccttt ttaacccatc acatatacct gccgttcact attatttagt   540
gaaatgagat attatgatat tttctgaatt gtgattaaaa aggcaacttt atgcccatgc   600
aacagaaact ataaaaaata cagagaatga aagaaacag atagatttt tagttcttta    660 ggcccgtagt ctgcaaatcc ttttatgatt ttctatcaaa caaaagagga aaatagacca   720
gttgcaatcc aaacgagagt ctaatagaat gaggtcgaaa agtaaatcgc gcgggtttgt   780
tactgataaa gcaggcaaga cctaaaatgt gtaaagggca agtgtatac tttggcgtca    840 ccccttacat attttaggtc ttttttttatt gtgcgtaact aacttgccat cttcaaacag   900
gagggctgga agaagcagac cgctaacaca gtacataaaa aaggagacat gaacgatgaa   960
catcaaaaag tttgcaaaac aagcaacagt attaaccttt actaccgcac tgctggcagg  1020
aggcgcaact caagcgtttg cgaaagaaac gaaccaaaag ccatataagg aaacatacgg  1080
catttcccat attacacgcc atgatatgct gcaaatccct gaacagcaaa aaaatgaaaa  1140
```

```
atatcaagtt cctgagttcg attcgtccac aattaaaaat atctcttctg caaaaggcct    1200
ggacgtttgg gacagctggc cattacaaaa cgctgacggc actgtcgcaa actatcacgg    1260
ctaccacatc gtctttgcat tagccggaga tcctaaaaat gcggatgaca catcgattta    1320
catgttctat caaaaagtcg gcgaaacttc tattgacagc tggaaaaacg ctggccgcgt    1380
ctttaaagac agcgacaaat tcgatgcaaa tgattctatc ctaaaagacc aaacacaaga    1440
atggtcaggt tcagccacat ttacatctga cggaaaaatc cgtttattct acactgattt    1500
ctccggtaaa cattacggca aacaaacact gacaactgca caagttaacg tatcagcatc    1560
agacagctct ttgaacatca acggtgtaga ggattataaa tcaatctttg acggtgacgg    1620
aaaaacgtat caaaatgtac agcagttcat cgatgaaggc aactacagct caggcgacaa    1680
ccatacgctg agagatcctc actacgtaga agataaaggc cacaaatact tagtatttga    1740
agcaaacact ggaactgaag atggctacca aggcgaagaa tctttatttta caaaagcata    1800 ctatggcaaa agcacatcat tcttccgtca agaaagtcaa aaacttctgc aaagcgataa    1860
aaaacgcacg gctgagttag caaacggcgc tctcggtatg attgagctaa acgatgatta    1920
cacactgaaa aaagtgatga aaccgctgat tgcatctaac acagtaacag atgaaattga    1980
acgcgcgaac gtctttaaaa tgaacggcaa atggtatctg ttcactgact cccgcggatc    2040
aaaaatgacg attgacggca ttcgtctaa cgatatttac atgcttggtt atgtttctaa    2100
ttctttaact ggcccataca agccgctgaa caaaactggc cttgtgttaa aaatggatct    2160
tgatcctaac gatgtaacct ttacttactc acacttcgct gtacctcaag cgaaaggaaa    2220
caatgtcgtg attacaagct atatgacaaa cagaggattc tacgcagaca aacaatcaac    2280
gtttgcgccc agcttcctgc tgaacatcaa aggcaagaaa acatctgttg tcaaagacag    2340
catccttgaa caaggacaat taacagttaa caaataaaaa cgcaaaagaa aatgccgata    2400
tcctattggc attttctttt atttcttatc aacataaagg tgaatcccat atgaactata    2460
taaaagcagg caaatggcta accgtattcc taacctttg gtaatgactc caattattga    2520 tagtgttta tgttcagata atgcccgatg actttgtcat gcagctccac cgattttgag    2580
aacgacagcg acttccgtcc cagccgtgcc aggtgctgcc tcagattcag gttatgccgc    2640
tcaattcgct gcgtatatcg cttgctgatt acgtgcagct ttcccttcag gcgggattca    2700
tacagcggcc agccatccgt catccatatc accacgtcaa agggtgacag caggctcata    2760
agacgcccca gcgtcgccat agtgcgttca ccgaatacgt gcgcaacaac cgtcttccgg    2820
agactgtcat acgcgtaaaa cagccagcgc tggcgcgatt tagccccgac atagccccac    2880
tgttcgtcca tttccgcgca gacgatgacg tcactgcccg gctgtatgcg cgaggttacc    2940
gactgcggcc tgagtttttt aagtgacgta aatcgtgtt gaggccaacg cccataatgc    3000
gggctgttgc ccggcatcca acgccattca tggccatatc aatgattttc tggtgcgtac    3060
cgggttgaga agcggtgtaa gtgaactgca tgaattcccg ggagagctcg atatcgcatg    3120
cggtacctct agaagaagct tgctgcggca ttgccggtac gtatggattt aaaaaggaaa    3180
actatccgac atcacagtcc atcggcgcgc cgctgttccg ccagattgaa gagagcggcg    3240
ccgacattgt cgtcaccgat tgtgaaacct gtaagtggca aattgagatg tctacaagca    3300
aacgctgcga acaccccatt acgctactgg cccaggcgct cggctaagta aaaagcgccg    3360
gagcccctcc ggcgccatta ccctactcac caggacgcat tttccatcag acatataccc    3420
ttcatacttc aagttgctta tgtgttggct acggattatt ttgggtataa acgcggatgt    3480
```

```
ctctttgcaa taacctgccc tatttggtta accatgaccg ctaacccacg gtggcatgac    3540
agataacgac gttactgttt atagagcaat atctcttgta tcgacgcgtt accagccacc    3600
tttaaagagg gggataactg aatatcccca ataataattg agtgttatgt gaataataag    3660
aaaatcaggt ctatgcctga tttaatatat cccccgctaa taataatatt tttacaaata    3720
attatacatt acatcatatt cgctactttc acttaccagg aaacagagca aaatgaatat    3780
atgtgtaaat tcactttacc gattgagcat accgcaattt cacagcttat atacagaaga    3840
gtggtgagta cttagagcct atcccattag gctcttatcc tgaaatgatg ctctgcgaag    3900
aatttataag tatataaggg tgggaaggcc aggccttccc actaaaagtt ctatgccgtc    3960
aatgattcaa ccacgtctat ccagccatgc tcgctggtaa tgtcctcgcc attaagccaa    4020
cggcgcagca tatttagcgc catcaccgca caaacctcct gacgtattgc cagactatac    4080
cgataggcgc taaaacgcat gcgtaaggca tacgtgccat ccggcatttt tctcaataac    4140
tacgttttgc cgtgcttact gactgaacag atttaaacat cgccaacctg ctgtccagcg    4200
cctcggtgta gagcatcgta tctacccga ccgcgacaaa attcgcgccc cacgccagac    4260
atttctgcgc cattgccgga tcgaccgcca aaaacccgc cgcttttccg gcggcgcgaa    4320
tacgataaat acacgcttca atgattcgct gcacttccgg gtgtccggca ttatcggggt    4380
aacccaatga agcagagaga tctgccggac cgataaagac gccatcaatg ccttcaacct    4440
ccagaatcgc gtcaaggttt tccagcgcca ctttgctttc aacctgcacc aacaggcaga    4500
gcgactcatt ggcctgtgcc atatagttgt cgattctccc cgaattccgg atgagcattc    4560
atcaggcggg caagaatgtg aataaaggcc ggataaaact tgtgcttatt tttctttacg    4620
gtctttaaaa aggccgtaat atccagctga acggtctggt tataggtaca ttgagcaact    4680
gactgaaatg cctcaaaatg ttcttttacga tgccattggg atatatcaac ggtggtatat    4740
ccagtgattt ttttctccat tttagcttcc ttagctcctg aaaatctcga taactcaaaa    4800
aatacgcccg gtagtgatct tatttcatta tggtgaaagt tggaacctct tacgtgccga    4860
tcaacgtctc attttcgcca aaagttggcc cagggcttcc cggtatcaac agggacacca    4920
ggatttattt attctgcgaa gtgatcttcc gtcacaggta ttagggcccg atccttttg    4980 tccggtgttg ggttgaaggt gaagccggtc ggggccgcag cggggccgg ctttcagcc    5040 ttgcccccct gcttcggccg ccgtggctcc ggcgtcttgg gtgccggcgc gggttccgca    5100
gccttggcct gcggtgcggg cacatcggcg ggcttggcct tgatgtgccg cctggcgtgc    5160
gagcggaacg tctcgtagga gaacttgacc ttccccgttt cccgcatgtg ctcccaaatg    5220
gtgacgagcg catagccgga cgctaacgcc gcctcgacat ccgccctcac cgccaggaac    5280
gcaaccgcag cctcatcacg ccggcgcttc ttggccgcgc gggattcaac ccactcggcc    5340
agctcgtcgg tgtagctctt tggcatcgtc tctcgcctgt cccctcagtt cagtaatttc    5400
ctgcatttgc ctgttccag tcggtagata ttccacaaaa cagcagggaa gcagcgcttt    5460
tccgctgcat aaccctgctt cggggtcatt atagcgattt tttcggtata tccatccttt    5520
ttcgcacgat atacaggatt ttgccaaagg gttcgtgtag actttccttg gtgtatccaa    5580
cggcgtcagc cgggcaggat aggtgaagta ggcccaccg cgagcgggtg ttccttcttc    5640
actgtccctt attcgcacct ggcggtgctc aacgggaatc ctgctctgcg aggctggccg    5700
gctaccgccg gcgtaacaga tgagggcaag cggatggctg atgaaaccaa gccaaccagg    5760
aagggcagcc cacctatcaa ggtgtactgc cttccagacg aacgaagagc gattgaggaa    5820
aaggcggcgg cggccggcat gagcctgtcg gcctacctgc tggccgtcgg ccagggctac    5880
```

```
aaaatcacgg gcgtcgtgga ctatgagcac gtccgcgagc tggcccgcat caatggcgac      5940
ctgggccgcc tgggcggcct gctgaaactc tggctcaccg acgacccgcg cacggcgcgg      6000
ttcggtgatg ccacgatcct cgccctgctg gcgaagatcg aagagaagca ggacgagctt      6060
ggcaaggtca tgatgggcgt ggtccgcccg agggcagagc catgactttt ttagccgcta      6120
aaacggccgg ggggtgcgcg tgattgccaa gcacgtcccc atgcgctcca tcaagaagag      6180
cgacttcgcg gagctggtga agtacatcac cgacgagcaa ggcaagaccg agcgcctggg      6240
tcacgtgcgc gtcacgaact gcgaggcaaa caccctgccc gctgtcatgg ccgaggtgat      6300
ggcgacccag cacggcaaca cccgttccga ggccgacaag acctatcacc tgctggttag      6360
cttccgcgcg ggagagaagc ccgacgcgga cgttgcgc gcgattgagg accgcatctg       6420
cgctgggctt ggcttcgccg agcatcagcc cgtcagtgcc gtgcatcacg acaccgacaa      6480
cctgcacatc catatcgcca tcaacaagat tcacccgacc cgaaacacca tccatgagcc      6540
gtatcgggcc taccgcgccc tcgctgacct ctgcgcgacg ctcgaacggg actacgggct      6600
tgagcgtgac aatcacgaaa cgcggcagcg cgtttccgag aaccg                     6645
```

<210> SEQ ID NO 42
<211> LENGTH: 7165
<212> TYPE: DNA
<213> ORGANISM: Artificial Sequence
<220> FEATURE:
<223> OTHER INFORMATION: Synthetic- plasmid pK4952: suicide vector for
      construction of spvD deletion mutation <400> SEQUENCE: 42

```
cgcgtttccg agaaccgcgc gaacgacatg gagcggcacg cgggcgtgga aagcctggtc       60
ggctggatcg gcacgatgcg tccggcgtag aggatctgaa gatccagcag ttcaacctgt      120
tgatagtacg tactaagctc tcatgtttca cgtactaagc tctcatgttt aacgtactaa      180
gctctcatgt ttaacgaact aaaccctcat ggctaacgta ctaagctctc atggctaacg      240
tactaagctc tcatgtttca cgtactaagc tctcatgttt gaacaataaa attaatataa      300
atcagcaact aaatagcct ctaaggtttt aagttttata agaaaaaaaa gaatatataa       360
ggcttttaaa gcttttaagg tttaacggtt gtggacaaca agccagggat gtaacgcact      420
gagaagccct tagagcctct caaagcaatt ttcagtgaca caggaacact taacggctga      480
catgggaatt ctgatccttt ttaacccatc acatatacct gccgttcact attatttagt      540
gaaatgagat attatgatat tttctgaatt gtgattaaaa aggcaacttt atgcccatgc      600
aacagaaact ataaaaaata cagagaatga aaagaaacag atagattttt tagttctta       660 ggccccgtagt ctgcaaatcc tttttatgatt ttctatcaaa caaaagagga aaatagacca     720
gttgcaatcc aaacgagagt ctaatagaat gaggtcgaaa agtaaatcgc gcgggtttgt      780
tactgataaa gcaggcaaga cctaaaatgt gtaaagggca aagtgtatac tttggcgtca      840
ccccttacat attttaggtc ttttttttatt gtgcgtaact aacttgccat cttcaaacag      900
gagggctgga agaagcagac cgctaacaca gtacataaaa aaggagacat gaacgatgaa      960
catcaaaaag tttgcaaaac aagcaacagt attaaccttt actaccgcac tgctggcagg     1020
aggcgcaact caagcgtttg cgaaagaaac gaaccaaaag ccatataagg aaacatacgg     1080
catttcccat attacacgcc atgatatgct gcaaatccct gaacagcaaa aaatgaaaa      1140 atatcaagtt cctgagttcg attcgtccac aattaaaaat atctcttctg caaaaggcct     1200
ggacgtttgg gacagctggc cattacaaaa cgctgacggc actgtcgcaa actatcacgg     1260
```

```
ctaccacatc gtctttgcat tagccggaga tcctaaaaat gcggatgaca catcgattta    1320
catgttctat caaaaagtcg gcgaaacttc tattgacagc tggaaaaacg ctggccgcgt    1380
ctttaaagac agcgacaaat tcgatgcaaa tgattctatc ctaaaagacc aaacacaaga    1440
atggtcaggt tcagccacat ttacatctga cggaaaaatc cgtttattct acactgattt    1500
ctccggtaaa cattacggca aacaaacact gacaactgca caagttaacg tatcagcatc    1560
agacagctct ttgaacatca acggtgtaga ggattataaa tcaatctttg acggtgacgg    1620
aaaaacgtat caaaatgtac agcagttcat cgatgaaggc aactacagct caggcgacaa    1680
ccatacgctg agagatcctc actacgtaga agataaaggc cacaaatact tagtatttga    1740
agcaaacact ggaactgaag atggctacca aggcgaagaa tctttattta caaagcata    1800 ctatggcaaa agcacatcat tcttccgtca agaaagtcaa aaacttctgc aaagcgataa    1860
aaaacgcacg gctgagttag caaacggcgc tctcggtatg attgagctaa cgatgatta    1920 cacactgaaa aaagtgatga aaccgctgat tgcatctaac acagtaacag atgaaattga    1980
acgcgcgaac gtctttaaaa tgaacggcaa atggtatctg ttcactgact cccgcggatc    2040
aaaaatgacg attgacggca ttcgtctaa cgatatttac atgcttggtt atgtttctaa    2100
ttctttaact ggcccataca agccgctgaa caaaactggc cttgtgttaa aaatggatct    2160
tgatcctaac gatgtaacct ttacttactc acacttcgct gtacctcaag cgaaaggaaa    2220
caatgtcgtg attacaagct atatgacaaa cagaggattc tacgcagaca aacaatcaac    2280
gtttgcgccc agcttcctgc tgaacatcaa aggcaagaaa acatctgttg tcaaagacag    2340
catccttgaa caaggacaat taacagttaa caaataaaaa cgcaaaagaa aatgccgata    2400
tcctattggc atttttcttt atttcttatc aacataaagg tgaatcccat atgaactata    2460
taaaagcagg caaatggcta accgtattcc taaccttttg gtaatgactc caattattga    2520
tagtgtttta tgttcagata atgcccgatg actttgtcat gcagctccac cgattttgag    2580
aacgacagcg acttccgtcc cagccgtgcc aggtgctgcc tcagattcag gttatgccgc    2640
tcaattcgct gcgtatatcg cttgctgatt acgtgcagct ttcccttcag gcgggattca    2700
tacagcggcc agccatccgt catccatatc accacgtcaa agggtgacag caggctcata    2760
agacgcccca gcgtcgccat agtgcgttca ccgaatacgt gcgcaacaac cgtcttccgg    2820
agactgtcat acgcgtaaaa cagccagcgc tggcgcgatt tagccccgac atagccccac    2880
tgttcgtcca tttccgcgca gacgatgacg tcactgcccg gctgtatgcg cgaggttacc    2940
gactgcggcc tgagtttttt aagtgacgta aatcgtgtt gaggccaacg cccataatgc    3000
gggctgttgc ccggcatcca acgccattca tggccatatc aatgattttc tggtgcgtac    3060
cgggttgaga agcggtgtaa gtgaactgca tgaattccg ggagagctcg atatcgcatg    3120
cggtacctct agaagaagct tctcagggca atttgccgg tgacaagttc cacatcagtg    3180
tgctcaggga tatggtgcca caagcatttc aagcgctgtc cggattgctg ttttcagagg    3240
acagtccggt agataagtgg aaagtgaccg atatggagaa ggtcgttcaa caagcccgtg    3300
ttagcctggg cgctcagttc acgttgtata taaaaccaga ccaggaaaat tcgcagtaca    3360
gtgcgtcgtt tctccacaag acacggcaat ttatagagtc tctggaatcc agactatccg    3420
aaaatggggt tatttcagga cagtgtcctg agtcagacgt tcatcctgaa aattggaaat    3480
atctcagtta tcgtaatgaa ctacgaagtg ggcgtgatgg tggcgaaatg cagagacagg    3540
ctttacgtga ggaaccgttt tatcgtttga tgacagagta agtatgggtt tggggagcaa    3600
```

```
cggaacagta aacgccgtta aacagctatt ttaaatgctc attaatttat taatcaataa    3660
attacaaatt ttcattgaag gctccccct tactgacgaa ttccggcacc gtaaaggaat     3720
aacgctcatg catattgata tgtccgcact gtaatggtga aaattacata agcaagagcg    3780
tttttttgaaa aatattatat ttaatgtttt gtaatatgca ttttattgag gtagtgtaac   3840
ttaactttt taaatattca ttttatgaat ggtaagttaa tagagagcct tagcaagatc     3900
cgctgtaaac cctcgcccaa tgcgggcggg gatataaggc gaaaagcccg aagggcttta    3960
ggcaggcta ctccggcgta ttctgtctga gcacgtatgc tttaagcgtt tctatcgtgg     4020
caccaccggc gctacaggca aagtaagaac gagaccacag cagcccggtt ttgctctgca    4080
tccgcaagtg ggtattctgc tgacggagaa gccgcgacga taccgacttt aaattattta    4140
ccatcacgct gaccccccagt tttagcggat acgctatcag cagatggacg tgatcttgtt   4200
caccatccat ctcgataatt tcgcactcca actttgccgc agccgaacca aaagcatcac    4260
gtaactgagc gataatctgc ccgtcaaaca gcttgcagcg gtattttgtc gtaaagatta    4320
atgcacaacc agcttactta cactatgccg tttacgaaga aagccttcca gtgattcgtg    4380
gtgattactc aattgaattt ttcacttaac atgttaaaat aaatacaata tattaatgag    4440
cgctgaatat gttaagagcc acgaaagtat gcatatatcc gacaccggaa caggcggagc    4500
accttaacgc ccagttcggt gcagtccgtt ttgtgtacag caagcttggg atcgggccct    4560
atcacttatt caggcgtagc aaccaggcgt ttaagggcac caataactgc cttaaaaaaa    4620
ttacgccccg ccctgccact catcgcagta ctgttgtaat tcattaagca ttctgccgac    4680
atggaagcca tcagacggg catgatgaac ctgaatcgcc agcggcatca gcaccttgtc     4740
gccttgcgta taatatttgc ccatggtgaa acgggggcg aagaagttgt ccatattggc     4800
cacgtttaaa tcaaaactgg tgaaactcac ccagggattg gctgagacga aaacatatt     4860
ctcaataaac cctttaggga ataggccag gttttcaccg taacacgcca catcttgcga     4920
atatatgtgt agaaactgcc ggaaatcgtc gtggtattca ctccagagcg atgaaaacgt    4980
ttcagtttgc tcatggaaaa cggtgtaaca agggtgaaca ctatcccata tcaccagctc    5040
accgtctttc attgccatac ggaattccgg atgagcattc atcaggcggg caagaatgtg    5100
aataaaggcc ggataaaact tgtgcttatt tttctttacg gtctttaaaa aggccgtaat    5160
atccagctga acgtctggt tataggtaca ttgagcaact gactgaaatg cctcaaaatg     5220
ttctttacga tgccattggg atatatcaac ggtggtatat ccagtgattt ttttctccat    5280
tttagcttcc ttagctcctg aaaatctcga taactcaaaa aatacgcccg gtagtgatct    5340
tatttcatta tggtgaaagt tggaaacctct tacgtgccga tcaacgtctc attttcgcca   5400
aaagttggcc cagggcttcc cggtatcaac agggacacca ggatttattt attctgcgaa    5460
gtgatcttcc gtcacaggta ttagggcccg atccttttg tccggtgttg ggttgaaggt     5520
gaagccggtc ggggccgcag cggggccgg cttttcagcc ttgcccccct gcttcggccg     5580
ccgtggctcc ggcgtcttgg gtgccggcgc gggttccgca gccttggcct gcggtgcggg    5640
cacatcggcg ggcttggcct tgatgtgccg cctggcgtgc gagcggaacg tctcgtagga    5700
gaacttgacc ttccccgttt ccccgcatgtg ctcccaaatg gtgacgagcg catagccgga   5760
cgctaacgcc gcctcgacat ccgccctcac cgccaggaac gcaaccgcag cctcatcacg    5820
ccggcgcttc ttggccgcgc gggattcaac ccactcggcc agctcgtcgg tgtagctctt    5880
tggcatcgtc tctcgcctgt cccctcagtt cagtaatttc ctgcatttgc ctgtttccag    5940
tcggtagata ttccacaaaa cagcagggaa gcagcgcttt tccgctgcat aaccctgctt    6000
```

```
cggggtcatt atagcgattt tttcggtata tccatccttt ttcgcacgat atacaggatt    6060
ttgccaaagg gttcgtgtag actttccttg gtgtatccaa cggcgtcagc cgggcaggat    6120
aggtgaagta ggcccacccg cgagcgggtg ttccttcttc actgtccctt attcgcacct    6180
ggcggtgctc aacgggaatc ctgctctgcg aggctggccg gctaccgccg gcgtaacaga    6240
tgagggcaag cggatggctg atgaaaccaa gccaaccagg aagggcagcc cacctatcaa    6300
ggtgtactgc cttccagacg aacgaagagc gattgaggaa aaggcggcgg cggccggcat    6360
gagcctgtcg gcctacctgc tggccgtcgg ccagggctac aaaatcacgg gcgtcgtgga    6420
ctatgagcac gtccgcgagc tggcccgcat caatggcgac ctgggccgcc tgggcggcct    6480
gctgaaactc tggctcaccg acgacccgcg cacggcgcgg ttcggtgatg ccacgatcct    6540
cgccctgctg gcgaagatcg aagagaagca ggacgagctt ggcaaggtca tgatgggcgt    6600
ggtccgcccg agggcagagc catgactttt ttagccgcta aaacggccgg ggggtgcgcg    6660
tgattgccaa gcacgtcccc atgcgctcca tcaagaagag cgacttcgcg gagctggtga    6720
agtacatcac cgacgagcaa ggcaagaccg agcgcctggg tcacgtgcgc gtcacgaact    6780
gcgaggcaaa caccctgccc gctgtcatgg ccgaggtgat ggcgacccag cacggcaaca    6840
cccgttccga ggccgacaag acctatcacc tgctggttag cttccgcgcg ggagagaagc    6900
ccgacgcgga gacgttgcgc gcgattgagg accgcatctg cgctgggctt ggcttcgccg    6960
agcatcagcg cgtcagtgcc gtgcatcacg acaccgacaa cctgcacatc catatcgcca    7020
tcaacaagat tcacccgacc cgaaacacca tccatgagcc gtatcgggcc taccgcgccc    7080
tcgctgacct ctgcgcgacg ctcgaacggg actacgggct tgagcgtgac aatcacgaaa    7140
cgcggcagcg cgtttccgag aaccg                                          7165

<210> SEQ ID NO 43
<211> LENGTH: 7165
<212> TYPE: DNA
<213> ORGANISM: Artificial Sequence
<220> FEATURE:
<223> OTHER INFORMATION: Synthetic- plasmid pK4953: suicide vector for
      construction of ssrAB deletion mutation

<400> SEQUENCE: 43
cgcgtttccg agaaccgcgc gaacgacatg gagcggcacg cgggcgtgga aagcctggtc      60
ggctggatcg gcacgatgcg tccggcgtag aggatctgaa gatccagcag ttcaacctgt     120
tgatagtacg tactaagctc tcatgtttca cgtactaagc tctcatgttt aacgtactaa     180
gctctcatgt ttaacgaact aaaccctcat ggctaacgta ctaagctctc atggctaacg     240
tactaagctc tcatgtttca cgtactaagc tctcatgttt gaacaataaa attaatataa     300
atcagcaact aaatagcct ctaaggtttt aagttttata agaaaaaaaa gaatatataa      360
ggcttttaaa gcttttaagg tttaacggtt gtggacaaca agccagggat gtaacgcact    420
gagaagccct tagagcctct caaagcaatt ttcagtgaca caggaacact taacggctga    480
catgggaatt ctgatccttt ttaacccatc acatatacct gccgttcact attatttagt    540
gaaatgagat attatgatat tttctgaatt gtgattaaaa aggcaacttt atgcccatgc    600
aacagaaact ataaaaaata cagagaatga aagaaacag atagatttt tagttcttta     660 ggcccgtagt ctgcaaatcc ttttatgatt ttctatcaaa caaaagagga aaatagacca   720
gttgcaatcc aaacgagagt ctaatagaat gaggtcgaaa agtaaatcgc gcgggtttgt    780
tactgataaa gcaggcaaga cctaaaatgt gtaaagggca aagtgtatac tttggcgtca    840
```

-continued

```
ccccttacat attttaggtc ttttttatt gtgcgtaact aacttgccat cttcaaacag      900
gagggctgga agaagcagac cgctaacaca gtacataaaa aaggagacat gaacgatgaa      960
catcaaaaag tttgcaaaac aagcaacagt attaacctt actaccgcac tgctggcagg     1020
aggcgcaact caagcgtttg cgaaagaaac gaaccaaaag ccatataagg aaacatacgg     1080
catttcccat attacacgcc atgatatgct gcaaatccct gaacagcaaa aaatgaaaa      1140 atatcaagtt cctgagttcg attcgtccac aattaaaaat atctcttctg caaaaggcct     1200
ggacgtttgg gacagctggc cattacaaaa cgctgacggc actgtcgcaa actatcacgg     1260
ctaccacatc gtctttgcat tagccggaga tcctaaaaat gcggatgaca catcgattta     1320
catgttctat caaaaagtcg gcgaaacttc tattgacagc tggaaaaacg ctggccgcgt     1380
ctttaaagac agcgacaaat tcgatgcaaa tgattctatc ctaaaagacc aaacacaaga     1440
atggtcaggt tcagccacat ttacatctga cggaaaaatc cgtttattct acactgattt     1500
ctccggtaaa cattacggca aacaaacact gacaactgca caagttaacg tatcagcatc     1560
agacagctct ttgaacatca acggtgtaga ggattataaa tcaatctttg acggtgacgg     1620
aaaaacgtat caaaatgtac agcagttcat cgatgaaggc aactcagct caggcgacaa     1680 ccatacgctg agagatcctc actacgtaga agataaaggc cacaaatact tagtatttga     1740
agcaaacact ggaactgaag atggctacca aggcgaagaa tctttattta acaaagcata     1800
ctatggcaaa agcacatcat tcttccgtca agaaagtcaa aaacttctgc aaagcgataa     1860
aaaacgcacg gctgagttag caaacggcgc tctcggtatg attgagctaa cgatgattta     1920
cacactgaaa aaagtgatga accgctgat tgcatctaac acagtaacag atgaaattga     1980
acgcgcgaac gtctttaaaa tgaacggcaa atggtatctg ttcactgact cccgcggatc     2040
aaaaatgacg attgacggca ttacgtctaa cgatatttac atgcttggtt atgtttctaa     2100 ttcttaact ggcccataca agccgctgaa caaaactggc cttgtgttaa aaatggatct     2160
tgatcctaac gatgtaacct ttacttactc acacttcgct gtacctcaag cgaaaggaaa     2220
caatgtcgtg attacaagct atatgacaaa cagaggattc tacgcagaca acaatcaac     2280 gtttgcgccc agcttcctgc tgaacatcaa aggcaagaaa acatctgttg tcaaagacag     2340
catccttgaa caaggacaat taacagttaa caaataaaa cgcaaaagaa atgccgata     2400 tcctattggc attttctttt atttcttatc aacataaagg tgaatcccat atgaactata     2460
taaaagcagg caaatggcta accgtattcc taaccttttg gtaatgactc caattattga     2520
tagtgtttta tgttcagata atgcccgatg actttgtcat gcagctccac cgattttgag     2580
aacgacagcg acttccgtcc cagccgtgcc aggtgctgcc tcagattcag gttatgccgc     2640
tcaattcgct gcgtatatcg cttgctgatt acgtgcagct ttcccttcag gcgggattca     2700
tacagcggcc agccatccgt catccatatc accacgtcaa agggtgacag caggctcata     2760
agacgcccca gcgtcgccat agtgcgttca ccgaatacgt gcgcaacaac cgtcttccgg     2820
agactgtcat acgcgtaaaa cagccagcgc tggcgcgatt tagccccgac atagccccac     2880
tgttcgtcca tttccgcgca gacgatgacg tcactgcccg gctgtatgcg cgaggttacc     2940
gactgcggcc tgagttttt aagtgacgta aatcgtgtt gaggccaacg cccataatgc     3000
gggctgttgc ccggcatcca acgccattca tggccatatc aatgattttc tggtgcgtac     3060
cgggttgaga agcggtgtaa gtgaactgca tgaattccg ggagagctcg atatcgcatg     3120
cggtacctct agaagaagct tgggatcggg ccctatcact tattcaggcg tagcaaccag     3180
```

```
gcgtttaagg gcaccaataa ctgccttaaa aaaattacgc cccgccctgc cactcatcgc    3240
agtactgttg taattcatta agcattctgc cgacatggaa gccatcacag acggcatgat    3300
gaacctgaat cgccagcggc atcagcacct tgtcgccttg cgtataatat ttgcccatgg    3360
tgaaaacggg ggcgaagaag ttgtccatat tggccacgtt taaatcaaaa ctggtgaaac    3420
tcacccaggg attggctgag acgaaaaaca tattctcaat aaacccttta gggaaatagg    3480
ccaggttttc accgtaacac gccacatctt gcgaatatat gtgtagaaac tgccggaaat    3540
cgtcgtggta ttcactccag agcgatgaaa acgtttcagt ttgctcatgg aaaacggtgt    3600
aacaagggtg aacactatcc catatccacca gctcaccgtc tttcattgcc atacggaatt    3660
cgctactact tgtggtataa taccgtttta accatccccc atccgctgtg agctgtatag    3720
cataatcatg gacgtccggg tgtgctgcaa gcagtagtgt cacataggca agacaaggct    3780
taggtaagct ttccaggtca tttaagaaca agaaatagaa aaatgcttct gagaaaattt    3840
ctcctctggc aggatgccca tcaatagtca ttatccagga tcggctatta ccttcggccc    3900
tgatatcctg aattaatgga atgccttta aaactgccag catgaatccc tcctcagaca    3960
taaatgggag tttctatcaa attcgctcac aaccacatcc gtaaaaagcc tgattcacat    4020
ttatttcgac tatactcttc ttgtacaata tcaggatgct gtctacatat accttgtcac    4080
aggcgattct atcattcgga ttttccgata aattcacaat tacattttca gcattgacat    4140
aaaaacttac aatttgaaaa attatttatt aaataaactg ttacgatgtt tttacatcgc    4200
catcttatta aaaagtaatt gtagtcatcg actgggttat atatgaagaa atttatcttc    4260
ctaatgataa caccatcgat taatcttctg atgaaactat atgtactgcg atagtgatca    4320
agtgccaaag attttgcaac aggcaactgg agggaagcat tccagggggcg tccgatggta    4380 ttaagcattg gtcatatttt gatgagcctt acgccacgca gtattgctca tcatcgacaa    4440
aatccatacg gatgccctgg tatgccgcac catttatcac taccttagtc ttcatttgat    4500
catgatatag tagaatcccc ttatttaacg ggctttacca tgtcgtattc tatcggcgaa    4560
tttgccagac tatgcggtat caatgccgcc acgctaaggg catggcagcg acgctatggt    4620
ttattgaaac cgcagcgtac tgatggcgga catcgcttat acagcgatga cgatattcga    4680
caagcgctta gcattctcga ctgggtgaga aaaggcgtac cgataagcca ggtcaaaccc    4740
ttactgtcgc gtccggttat tcgcctgggc gataactgga taacgatcca ggagacgatg    4800
cttcaacatc tccacgaagg gcgaattgac gcgctgcggc agttgattta tgactgtggc    4860
cgggaatatc cccgcgcaga actggtgacc catttattgc gtccgttgcg cagcaaagtg    4920
tccgcgcatc ttcccgccgt gatgacgctg cgcgaaatac tggatggcat cattattgcc    4980
tacacctctt tttgccttga aggcgacaga aaagcgcctg gcaacaatgc ctttattagc    5040
ggatggaatc tctcggatca cgaattccgg atgagcattc atcaggcggg caagaatgtg    5100
aataaaggcc ggataaaact tgtgcttatt tttctttacg gtctttaaaa aggccgtaat    5160
atccagctga acggtctggt tataggtaca ttgagcaact gactgaaatg cctcaaaatg    5220
ttctttacga tgccattggg atatatcaac ggtggtatat ccagtgattt ttttctccat    5280
tttagcttcc ttagctcctg aaaatctcga taactcaaaa aatacgcccg gtagtgatct    5340
tatttcatta tggtgaaagt tggaacctct tacgtgccga tcaacgtctc attttcgcca    5400
aaagttggcc cagggcttcc cggtatcaac agggacacca ggatttatt attctgcgaa    5460 gtgatcttcc gtcacaggta ttagggcccg atccttttg tccggtgttg ggttgaaggt    5520
gaagccggtc ggggccgcag cgggggccgg cttttcagcc ttgcccccct gcttcggccg    5580
```

```
ccgtggctcc ggcgtcttgg gtgccggcgc gggttccgca gccttggcct gcggtgcggg    5640
cacatcggcg ggcttggcct tgatgtgccg cctggcgtgc gagcggaacg tctcgtagga    5700
gaacttgacc ttccccgttt cccgcatgtg ctcccaaatg gtgacgagcg catagccgga    5760
cgctaacgcc gcctcgacat ccgccctcac cgccaggaac gcaaccgcag cctcatcacg    5820
ccggcgcttc ttggccgcgc gggattcaac ccactcggcc agctcgtcgg tgtagctctt    5880
tggcatcgtc tctcgcctgt cccctcagtt cagtaatttc ctgcatttgc ctgtttccag    5940
tcggtagata ttccacaaaa cagcagggaa gcagcgcttt ccgctgcat  aaccctgctt    6000 cggggtcatt atagcgattt tttcggtata tccatccttt ttcgcacgat atacaggatt    6060
ttgccaaagg gttcgtgtag actttccttg gtgtatccaa cggcgtcagc cgggcaggat    6120
aggtgaagta ggcccacccg cgagcgggtg ttccttcttc actgtccctt attcgcacct    6180
ggcggtgctc aacgggaatc ctgctctgcg aggctggccg gctaccgccg gcgtaacaga    6240
tgagggcaag cggatggctg atgaaaccaa gccaaccagg aagggcagcc cacctatcaa    6300
ggtgtactgc cttccagacg aacgaagagc gattgaggaa aaggcggcgg cggccggcat    6360
gagcctgtcg gcctacctgc tggccgtcgg ccagggctac aaaatcacgg gcgtcgtgga    6420
ctatgagcac gtccgcgagc tggcccgcat caatggcgac ctgggccgcc tgggcggcct    6480
gctgaaactc tggctcaccg acgacccgcg cacggcgcgg ttcggtgatg ccacgatcct    6540
cgccctgctg gcgaagatcg aagagaagca ggacgagctt ggcaaggtca tgatgggcgt    6600
ggtccgcccg agggcagagc catgactttt ttagccgcta aaacggccgg ggggtgcgcg    6660
tgattgccaa gcacgtcccc atgcgctcca tcaagaagag cgacttcgcg gagctggtga    6720
agtacatcac cgacgagcaa ggcaagaccg agcgcctggg tcacgtgcgc gtcacgaact    6780
gcgaggcaaa caccctgccc gctgtcatgg ccgaggtgat ggcgacccag cacggcaaca    6840
cccgttccga ggccgacaag acctatcacc tgctggttag cttccgcgcg ggagagaagc    6900
ccgacgcgga gacgttgcgc gcgattgagg accgcatctg cgctgggctt ggcttcgccg    6960
agcatcagcg cgtcagtgcc gtgcatcacg acaccgacaa cctgcacatc catatcgcca    7020
tcaacaagat tcacccgacc cgaaacacca tccatgagcc gtatcgggcc taccgcgccc    7080
tcgctgacct ctgcgcgacg ctcgaacggg actacgggct tgagcgtgac aatcacgaaa    7140
cgcggcagcg cgtttccgag aaccg                                         7165
```

<210> SEQ ID NO 44
<211> LENGTH: 23
<212> TYPE: DNA
<213> ORGANISM: Artificial Sequence
<220> FEATURE:
<223> OTHER INFORMATION: Synthetic- Tar plus Flag Primer 4 for
      construction of pK4949 plasmid

<400> SEQUENCE: 44
ccgtggcggc gacgcgcatg ttc                                             23